United States Patent
Coburn et al.

(10) Patent No.: US 8,211,904 B2
(45) Date of Patent: Jul. 3, 2012

(54) SPIROPIPERIDINE BETA-SECRETASE INHIBITORS FOR THE TREATMENT OF ALZHEIMER'S DISEASE

(75) Inventors: Craig A. Coburn, Royersford, PA (US); Melissa S. Egbertson, Ambler, PA (US); Samuel L. Graham, Schwenskville, PA (US); Georgia B. McGaughey, Harleysville, PA (US); Shaun R. Stauffer, Schwenksville, PA (US); Hemaka A. Rajapakse, Wyncote, PA (US); Philippe G. Nantermet, Lansdale, PA (US); Shawn J. Stachel, Perkasie, PA (US); Wenjin Yang, Foster City, CA (US); Wanli Lu, Burlingame, CA (US); Bruce Fahr, Foster City, CA (US)

(73) Assignees: Merck, Sharp & Dohme Corp., Rahway, NJ (US); Sunesis Pharmaceuticals, Inc., South San Francisco, CA (US)

( * ) Notice: Subject to any disclaimer, the term of this patent is extended or adjusted under 35 U.S.C. 154(b) by 1136 days.

(21) Appl. No.: 11/487,229

(22) Filed: Jul. 14, 2006

(65) Prior Publication Data
US 2007/0021454 A1 Jan. 25, 2007

Related U.S. Application Data

(60) Provisional application No. 60/700,090, filed on Jul. 18, 2005.

(51) Int. Cl.
*A61K 31/438* (2006.01)
*C07D 401/04* (2006.01)
*C07D 403/04* (2006.01)

(52) U.S. Cl. .......................... 514/278; 546/18
(58) Field of Classification Search .................... 546/18; 514/278
See application file for complete search history.

(56) References Cited

U.S. PATENT DOCUMENTS

| | | | |
|---|---|---|---|
| 4,710,504 A | 12/1987 | Baldwin et al. | |
| 5,221,675 A | 6/1993 | Chung et al. | |
| 5,512,681 A | 4/1996 | Boswell et al. | |
| 5,534,520 A | 7/1996 | Fisher et al. | |
| 5,646,172 A | 7/1997 | Claussner et al. | |
| 2004/0067950 A1 | 4/2004 | Tulshian et al. | |
| 2004/0152707 A1 | 8/2004 | Tulshian et al. | |
| 2006/0052406 A1 | 3/2006 | Fisher et al. | |
| 2007/0197571 A1* | 8/2007 | Barrow et al. ................. | 514/278 |

FOREIGN PATENT DOCUMENTS

| | | |
|---|---|---|
| JP | 46039103 | 11/1971 |
| WO | WO 95/03303 | 2/1995 |
| WO | WO 99/65494 | 12/1999 |
| WO | WO 01/07050 | 2/2001 |
| WO | WO 03/057698 | 7/2003 |
| WO | WO 03/092580 | 11/2003 |
| WO | WO 03/106405 | 12/2003 |
| WO | WO 2004/037800 | 5/2004 |
| WO | WO 2004/050039 | 6/2004 |
| WO | WO 2005/005374 | 1/2005 |
| WO | WO 2005/035535 | 4/2005 |
| WO | WO 2006/044497 | 4/2006 |

OTHER PUBLICATIONS

Dorwald F. A. Side Reactions in Organic Synthesis, 2005, Wiley: VCH, Weinheim p. IX of Preface. Also see pp. 8 and 9.*
AJ Larner, "Secretases as therapeutic targets in Alzheimer's disease: Patents 2000-2004", Expert Opinion Ther. Patents, vol. 14, No. 10, pp. 1403-1420 (2004).
M. Van Parys et al., "The Synthesis of 1,8-Diazaspiro[4,5]-decanes," Bull. Soc. Chim. Belg., vol. 90/n, pp. 749-755, Jul. 1981.
Mehrotra, et al., "Discovery of Novel 2,8-Diazaspiro[4.5]decanes as Orally Active Glycoprotein IIb-IIIa Antagonists" J. Med. Chem. 2004, 47, 2037-2061.
Nieto, et al., "Solution-Phase Parallel Synthesis of Spirohydantoins", J. Comb. Chem. 2005, 7, 258-263.
Menendez, et al., "Synthesis of 1'-Substituted and 1'-3'-Disubstituted (±)2R*,11bS*-9,10-Dimethoxy-1,3,4,6,7,11b-Hexahydrospiro-[benzo[a]quinolizin-2,5'-imidazolidine]-2',4'-diones", J. Heterocyclic Chem., 28, 923-931 (1991).
Carrera, et al., "Synthesis of Novel Substituted Spirohydantoins", J. Heterocyclic Chem., 29, 847-850 (1992).
Hough, "Synthesis of Imidazolin-2-ones by Rearrangement of N-Carbamoyliminium Salts derived from 4-Hydroxyimidazolidin-2-ones", J. Heterocyclic Chem, 26, 1523-1525 (1989).

* cited by examiner

*Primary Examiner* — Rita Desai
(74) *Attorney, Agent, or Firm* — Keith D. MacMillan; Gerard M. Devlin

(57) ABSTRACT

The present invention is directed to spiropiperidine compounds of formula (I)

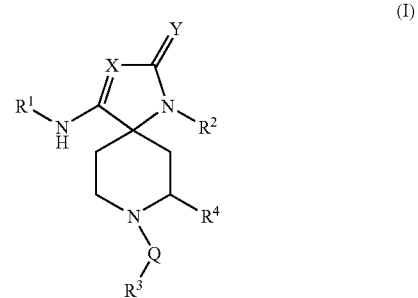

and tautomers thereof, which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

17 Claims, No Drawings

SPIROPIPERIDINE BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. Provisional Application Ser. No. 60/700,090, filed Jul. 18, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to spiropiperidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein ($\beta$A4, also referred to as A$\beta$,$\beta$-protein and $\beta$AP) which is a proteolytic product of a precursor protein of much larger size. The amyloid precursor protein (APP or A$\beta$PP) has a receptor-like structure with a large ectodomain, a membrane spanning region and a short cytoplasmic tail. The A$\beta$ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most APP, is released by a putative $\alpha$-secretase which cleaves within the A$\beta$ protein to release $\alpha$-$APP_s$ and precludes the release of intact A$\beta$. A minor portion of $APP_s$ is released by a $\beta$-secretase ("$\beta$-secretase"), which cleaves near the $NH_2$-terminus of APP and produces COOH-terminal fragments (CTFs) which contain the whole A$\beta$ domain.

Thus, the activity of $\beta$-secretase or $\beta$-site amyloid precursor protein-cleaving enzyme ("BACE") leads to the cleavage of APP, production of A$\beta$, and accumulation of $\beta$ amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit $\beta$-secretase or BACE may be useful for the treatment of Alzheimer's disease.

The compounds of the present invention are useful for treating Alzheimer's disease by inhibiting the activity of $\beta$-secretase or BACE, thus preventing the formation of insoluble A$\beta$ and arresting the production of A$\beta$.

SUMMARY OF THE INVENTION

The present invention is directed to spiropiperidine compounds represented by general formula (I)

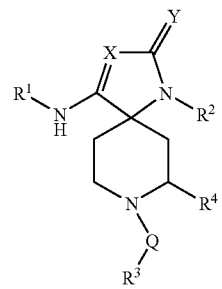

or its tautomer (I')

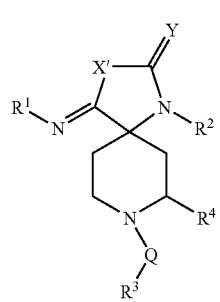

and individual enantiomers and diastereomers thereof, and pharmaceutically acceptable salts thereof, which are useful as inhibitors of the $\beta$-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the $\beta$-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to spiropiperidine compounds represented by general formula (I)

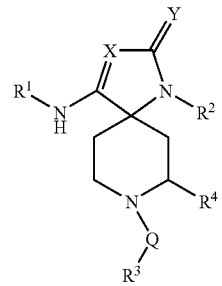

or its tautomer (I')

$$\text{(I')}$$

wherein

X is selected from the group consisting of
  (1) N; and
  (2) $CR^5$, wherein $R^5$ is selected from the group consisting of
    (a) hydrogen,
    (b) —$C_{1-6}$ alkyl,
    (c) —$C_{3-7}$ cycloalkyl,
    (d) —$C_{1-6}$ alkyl,
    (e) —$C_{0-6}$ alkyl-aryl,
    (f) —$C_{0-6}$ alkyl-heteroaryl,
    (g) halo, and
    (h) a heterocyclic group having 4 to 8 ring atoms, wherein one ring atom is a heteroatom selected from the group consisting of nitrogen and oxygen,
      wherein said alkyl, cycloalkyl, aryl or heteroaryl $R^5$ moiety is optionally substituted with one or more
        (I) halo,
        (II) —$C_{1-6}$ alkyl,
        (III) —O—$C_{1-6}$ alkyl, and
        (IV) —$NO_2$;
X' is selected from the group consisting of
  (1) $NR^5$; and
  (2) $CR^5R^{5'}$, wherein $R^{5'}$ is selected from the same group as $R^5$;
Y is selected from the group consisting of
  (1) O, and
  (2) S;
$R^1$ is selected from the group consisting of
  (1) hydrogen,
  (2) —$C_{1-10}$ alkyl,
  (3) —$C_{2-10}$ alkenyl,
  (4) —$C_{2-10}$ alkynyl,
  (5) —$C_{3-12}$ cycloalkyl, wherein one or two of the ring carbon atoms is optionally replaced by a —$Si(C_{1-6}$ alkyl$)_2$— group,
  (6) —$C_{3-12}$ cycloalkenyl,
  (7) a heterocyclic group having 4 to 8 ring atoms, wherein one ring atom is a heteroatom selected from the group consisting of nitrogen, sulfur or oxygen,
  (8) aryl, and
  (9) heteroaryl,
    wherein said alkyl, cycloalkyl, heterocyclic, alkenyl, alkynyl, aryl or heteroaryl $R^1$ moiety is optionally substituted with one or more
      (a) halo,
      (b) —OH,
      (c) —CN,
      (d) —$C_{1-10}$ alkyl
      (e) —$C_{3-12}$ cycloalkyl,
      (f) —O—$C_{1-10}$ alkyl,
      (g) —O—$CH_2$-aryl,
      (h) aryl,
      (i) heteroaryl,
      (j) —$NR^5R^{5'}$
      (k) —NC(=O)$R^5$,
      (l) a heterocyclic group having 4 to 8 ring atoms, wherein one ring atom is a heteroatom selected from the group consisting of nitrogen, sulfur and oxygen,
      (m) —$SO_2C_{1-3}$ alkyl,
      (n) —$SO_2NR^5R^{5'}$,
      (o) —$NR^5SO_2C_{1-3}$ alkyl,
      (p) —$CO_2R^5$,
      (q) —$CONR^5R^{5'}$,
      (r) —$COR^5$, and
      (s) —$Si(C_{1-6}$ alkyl$)_3$
        wherein said aryl or heteroaryl moiety is optionally substituted with one or more
          (I) halo,
          (II) —$C_{1-6}$ alkyl, wherein said alkyl is optionally substituted with one or more halogen,
          (III) —O—$C_{1-6}$ alkyl, and
          (IV) —$NO_2$;
$R^2$ is selected from the group consisting of
  (1) hydrogen,
  (2) —$C_{1-10}$ alkyl,
  (3) —$C_{2-10}$ alkenyl,
  (4) —$C_{2-10}$ alkynyl,
  (5) —$C_{3-12}$ cycloalkyl, wherein one or two of the ring carbon atoms is optionally replaced by a —$Si(C_{1-6}$ alkyl$)_2$— group,
  (6) a heterocyclic group having 4 to 8 ring atoms, wherein one ring atom is a heteroatom selected from the group consisting of nitrogen and oxygen,
  (7) aryl, and
  (8) heteroaryl,
    wherein said alkyl, cycloalkyl, heterocyclic group, alkenyl, alkynyl, aryl or heteroaryl $R^2$ moiety is optionally substituted with one or more
      (a) halo,
      (b) —OH,
      (c) —CN,
      (d) —$C_{1-10}$ alkyl
      (e) —$C_{3-12}$ cycloalkyl,
      (f) —O—$C_{10}$ alkyl,
      (g) —$C_{0-6}$ alkyl-aryl, wherein said aryl is optionally substituted with one or more
        (i) halo,
        (ii) —OH,
        (iii) —N,
        (iv) —$C_{1-6}$ alkyl,
        (v) —$C_{2-6}$ alkenyl,
        (vi) —$OC_{1-6}$ alkyl,
        (vii) —$C_{1-6}$ haloalkyl,
        (viii) —$SO_2C_{1-3}$ alkyl,
        (ix) —$SO_2NR^5R^{5'}$, or
        (x) —$CONR^5R^5$;
      (h) —$C_{0-6}$ alkyl-heteroaryl,
      (i) —NC(=O)—$NR^5R^{5'}$,
      (j) —NC(=$OC_{1-3}$ alkyl-$NR^5R^{5'}$,
      (k) —NC(=O)$R^5$,
      (l) —$NR^5R^{5'}$,
      (m) a heterocyclic group having 4 to 8 ring atoms, wherein one ring atom is a heteroatom selected from the group consisting of nitrogen and oxygen, and (n) —Si(C$_{1-6}$ alkyl)$_3$ and said alkyl, cycloalkyl, aryl, heteroaryl and heterocyclic moiety is optionally substituted with one or more
  (i) halo,
  (ii) —OH,
  (iii) —CN,
  (iv) —C$_{1-10}$ alkyl,
  (v) —OC$_{1-10}$ alkyl,
  (vi) —SO$_2$C$_{1-3}$ alkyl,
  (vii) —SO$_2$NR$^5$R$^{5'}$,
  (viii) —NR$^5$SO$_2$C$_{1-3}$alkyl,
  (ix) —CO$_2$R$^5$, and
  (x) —CONR$^5$R$^5$;

Q is —C$_{1-6}$ alkylene, wherein said alkylene is optionally substituted with one or more
  (a) halo,
  (b) —OH,
  (c) —CN,
  (d) —C$_{1-10}$ alkyl
  (e) —C$_{3-12}$ cycloalkyl,
  (f) —O—C$_{1-10}$ alkyl,
  (g) aryl, and
  (h) heteroaryl;

R$^3$ is selected from the group consisting of
  (1) hydrogen,
  (2) —C$_{1-10}$ alkyl,
  (3) —C$_{2-10}$ alkenyl,
  (4) —C$_{2-10}$ alkynyl,
  (5) —C$_{3-12}$ cycloalkyl, wherein one or two of the ring carbon atoms is optionally replaced by a —Si(C$_{1-6}$ alkyl)$_2$— group,
  (6) —C$_{3-12}$ cycloalkenyl,
  (7) aryl, and
  (8) heteroaryl,
  wherein said alkyl, cycloalkyl, cycloalkenyl, alkenyl, alkynyl, aryl or heteroaryl R$^3$ moiety is optionally substituted with one or more
    (a) halo,
    (b) —OH,
    (c) —CN,
    (d) —C$_{10}$ alkyl,
    (e) —C$_{2-10}$ alkenyl,
    (f) —C$_{3-12}$ cycloalkyl,
    (g) —O—C$_{3-12}$ cycloalkyl,
    (h) —O—C$_{1-10}$ alkyl,
    (i) —O—C$_{3-12}$ heterocyclic, wherein said heterocyclic group has from 4 to 8 ring atoms,
    wherein one ring atom is a heteroatom selected from the group consisting of nitrogen, sulfur and oxygen,
    (j) aryl,
    (k) heteroaryl,
    (l) —NR$^5$R$^{5'}$, and
    (m) —Si(C$_{1-6}$ alkyl)$_3$;
    and said alkyl, cycloalkyl, aryl and heteroaryl moiety is optionally substituted with one or more
      (i) halo,
      (ii) —OH,
      (iii) —CN,
      (iv) —C$_{3-12}$ cycloalkyl,
      (v) —C$_{10}$ alkyl,
      (vi) —OC$_{1-10}$ alkyl,
      (vii) —NR$^5$R$^{5'}$
      (viii) —C$_{2-6}$ alkenyl,
      (ix) —C$_{1-6}$ haloalkyl,
      (x) —SO$_2$C$_{1-3}$ alkyl,
      (xi) —SO$_2$NR$^5$R$^{5'}$, or
      (xii) —CONR$^5$R$^5$;

R$^4$ is —C$_{1-10}$ alkyl or —C$_{2-4}$ alkenyl, wherein said alkyl or alkenyl R$^4$ group is optionally substituted with one or more
  (a) halo,
  (b) —OH
  (c) —C$_{1-6}$ alkyl,
  (d) —CN,
  (e) —C$_{1-10}$ alkyl,
  (f) —NR$^8$R$^9$, wherein R$^8$ and R$^9$ are selected from the group consisting of
    (i) hydrogen, and
    (ii) —C$_{1-6}$alkyl,
  (g) —S(O)$_n$—C$_{1-6}$ alkyl, wherein n is 0, 1 or 2, and
  (h) —C(═O)R$^7$, wherein R$^7$ is selected from the group consisting of
    (i) hydrogen,
    (ii) —OH,
    (iii) —C$_{1-6}$ alkyl, and
    (iv) —OC$_{1-6}$ alkyl, and
    (v) aryl;
and pharmaceutically acceptable salts thereof, and individual enantiomers and diastereomers thereof.

In preferred embodiments of the compounds of formula (I), Y is O. In preferred embodiments of the compounds of formula (I), X is N.

In preferred embodiments of the compounds of formula (I'), X' is NH.

In preferred embodiments of the compounds of formula (I) and (I'), R$^1$ is selected from the group consisting of optionally substituted C$_{1-10}$ alkyl, preferably optionally substituted C$_{1-6}$ alkyl, or optionally substituted C$_{3-12}$ cycloalkyl, preferably optionally substituted C$_{3-6}$ cycloalkyl.

In preferred embodiments of the compounds of formula (I) and (I'), R$^2$ is phenyl, wherein the phenyl is optionally substituted with one or more
  (i) halo,
  (ii) —OH,
  (iii) —CN,
  (iv) —C$_{1-10}$ alkyl, and
  (v) phenyl optionally substituted with
    (A) halo,
    (B) —OH,
    (C) —CN,
    (D) —C$_{10}$ alkyl,
    (E) —OC$_{1-10}$ alkyl,
    (F) —SO$_2$C$_{1-3}$ alkyl,
    (G) —SO$_2$NR$^5$R$^{5'}$,
    (H) —NR$^5$SO$_2$C$_{1-3}$alkyl,
    (I) —CO$_2$R$^5$, and
    (J) —CONR$^5$R$^{5'}$.

In preferred embodiments of the compounds of formula (I) and (I'), Q is C$_{1-3}$ alkylene, most preferably —CH$_2$—, and R$^3$ is phenyl, wherein the phenyl is optionally substituted with one or more
  (A) halo,
  (B) —OH,
  (C) —CN,
  (D) —C$_{1-10}$ alkyl,
  (E) —OC$_{10}$ alkyl, and
  (F) phenyl, optionally substituted with
    (i) —C$_{1-6}$ alkyl,
    (ii) —OC$_{1-6}$ alkyl,
    (iii) NR$^5$R$^{5'}$.

In preferred embodiments of the compounds of formula (I) and (I'), $R^4$ is $C_{1-6}$ alkyl, most preferably methyl or ethyl.

In another embodiment, $R^4$ is -2-4 alkenyl.

Within the genus of compounds of formula (I) and (I'), there is a sub-genus of compounds of formula (II)

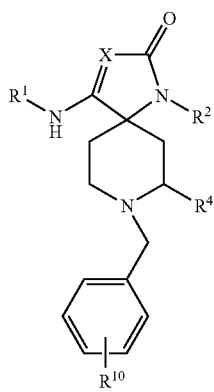

(II)

or its tautomer (II')

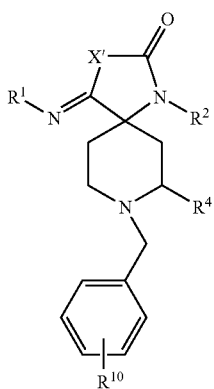

(II')

wherein X, X', $R^1$, $R^2$, and $R^4$ are as defined above, and $R^{10}$ is selected from the group consisting of
(1) halo,
(2) —OH,
(3) —CN,
(4) —$C_{1-10}$ alkyl, wherein said alkyl is optionally substituted with one or more halogen,
(5) —$C_{3-6}$ cycloalkyl, wherein said cycloalkyl is optionally substituted with one or more halogen,
(6) —$C_{2-10}$ alkenyl, and
(7) —$OC_{1-10}$ alkyl,
and pharmaceutically acceptable salts thereof, and individual enantiomers and diastereomers thereof.

In preferred embodiments of the compounds of formula (II), X is N.

In preferred embodiment of the compounds of formula (II'), X' is NH.

In preferred embodiments of the compounds of formula (II) and (II'), $R^2$ is phenyl, wherein the phenyl is optionally substituted with one or more
(i) halo,
(ii) —OH,
(iii) —CN,
(iv) —$C_{1-10}$ alkyl, or
(v) phenyl, optionally substituted with
(A) halo,
(B) —OH,
(C) —CN,
(D) —$C_{1-10}$ alkyl,
(E) —$OC_{1-10}$ alkyl,
(F) —$SO_2C_{1-3}$ alkyl,
(G) —$SO_2NR^5R^{5'}$,
(H) —$NR^5SO_2C_{1-3}$alkyl,
(I) —$CO_2R^5$, and
(J) —$CONR^5R^{5'}$.

In preferred embodiments of the compounds of formula (II) and (II'), $R^4$ is $C_{1-6}$ alkyl, most preferably methyl or ethyl.

In one embodiment of the compounds of formula (II) and (II'), $R^{10}$ is phenyl, which is optionally substituted with one or more $R^{13}$ groups selected from
(A) halo,
(B) —OH,
(C) —CN,
(D) —$C_{1-6}$ alkyl,
(E) —$C_{2-6}$ alkenyl,
(F) —$OC_{1-6}$ alkyl,
(G) —$C_{1-6}$ haloalkyl,
(H) —$SO_2C_{1-3}$ alkyl,
(I) —$SO_2NR^5R^{5'}$, or
(J) —$CONR^5R^5$.

Within the genus of compounds of formula (I), there is a sub-genus of compounds of formula (III)

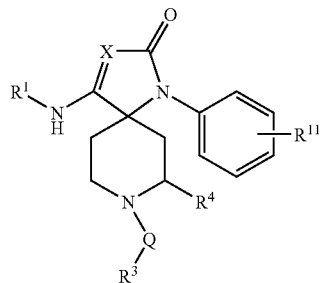

(III)

or its tautomer (III')

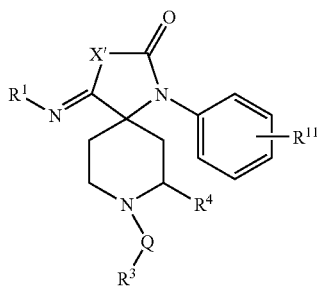

(III')

wherein X, X', Q, $R^1$, $R^3$, and $R^4$ are as defined above, and $R^{11}$ is selected from the group consisting of
(1) halo,
(2) —OH,
(3) —CN, (4) —$C_{1-10}$ alkyl, and (5) optionally substituted phenyl, and pharmaceutically acceptable salts thereof, and individual enantiomers and diastereomers thereof.

In preferred embodiments of the compounds of formula (III), X is N.

In preferred embodiment of the compounds of formula (III'), X' is NH.

In preferred embodiments of the compounds of formula (I) and (III'), Q is $C_{1-3}$ alkylene, most preferably —$CH_2$—, and $R^3$ is phenyl, wherein the phenyl is optionally substituted with one or more (A) halo, (B) —OH, (C) —CN, (D) —$C_{10}$ alkyl, (E) —$OC_{1-10}$ alkyl, or (F) phenyl, optionally substituted with (i) —$C_{1-6}$ alkyl, (ii) —$OC_{1-6}$ alkyl, (iii) $NR^5R^{5'}$.

In preferred embodiments of the compounds of formula (III) and (III'), $R^4$ is $C_{1-6}$ alkyl, most preferably methyl or ethyl.

In one embodiment of the compounds of formula (III) and (III'), $R^{11}$ is phenyl, which is optionally substituted with one or more $R^{12}$ groups selected from (A) halo, (B) —OH, (C) —CN, (D) —$C_{1-6}$ alkyl, (E) —$OC_{1-6}$ alkyl, (F) —$C_{2-6}$ alkenyl, (G) —$C_{1-6}$ haloalkyl, (H) —$SO_2C_{1-3}$ alkyl, (I) —$SO_2NR^5R^{5'}$, or (J) —$CONR^5R^5$.

In still another embodiment, the invention is directed to spiropiperidine compounds represented by general formula (I)

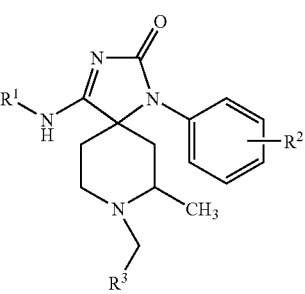

(IV)

or its tautomer (IV')

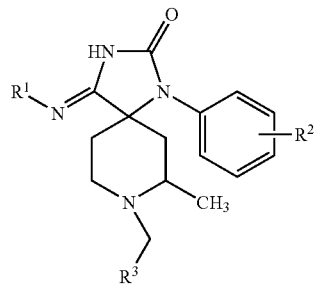

(IV')

wherein
$R^1$ is selected from the group consisting of
(1) hydrogen,
(2) —$C_{1-10}$ alkyl,
(3) —$C_{3-12}$ cycloalkyl,
(4) a heterocyclic group having 4 to 8 ring atoms, wherein one ring atom is a heteroatom selected from the group consisting of nitrogen, sulfur or oxygen, and
(5) phenyl,
wherein said alkyl, cycloalkyl, heterocyclic or phenyl $R^1$ moiety is optionally substituted with one or more
(a) hydrogen,
(b) halo,
(c) —H,
(d) —CN,
(e) —$C_{1-10}$ alkyl
(f) —$C_{3-12}$ cycloalkyl,
(g) —O—$C_{10}$ alkyl, or
(h) phenyl;
$R^2$ is optionally present at one or more of the ring carbon atoms, and is selected from the group consisting of
(1) halo,
(2) —OH,
(3) —CN, and
(4) —$C_{1-10}$ alkyl;
$R^3$ is selected from the group consisting of
(1) hydrogen,
(2) —$C_{1-10}$ alkyl,
(3) —$C_{3-12}$ cycloalkyl,
(4) phenyl, and
(5) heteroaryl,
wherein said alkyl, cycloalkyl, phenyl or heteroaryl $R^3$ moiety is optionally substituted with one or more
(a) halo,
(b) —OH,
(c) —CN,
(d) —1-10 alkyl,
(e) —$C_{3-12}$ cycloalkyl,
(f) —O—$C_{3-12}$ cycloalkyl,
(g) —O—$C_{1-10}$ alkyl,
and said alkyl, cycloalkyl and phenyl moiety is optionally substituted with one or more
(i) halo,
(ii) —OH,
(iii) —CN,
(iv) —$C_{3-12}$ cycloalkyl,
(v) —$C_{1-10}$alkyl, or
(vi) —$C_{1-10}$ alkyl;
and pharmaceutically acceptable salts thereof, and individual enantiomers and diastereomers thereof.

In preferred embodiments, the invention is directed to compounds of the invention of Examples 1-10, as follows:

Racemic 5(R,S)7(R,S)-8-benzyl-4-(cyclohexylamino)-1-(3-fluorophenyl)-7-methyl-1,3,8-triazaspiro[4.5]dec-3-en-2-one diastereomer A;

Racemic 5(R,S)7(S,R)-8-benzyl-4-(cyclohexylamino)-1-(3-fluorophenyl)-7-methyl-1,3,8-triazaspiro[4.5]dec-3-en-2-one Diastereomer B;

Racemic 5(R,S)7(R,S)-4-(cyclohexylamino)-1-(3-fluorophenyl)-8-(3-isopropoxybenzyl)-7-methyl-1,3,8-triazaspiro[4.5]dec-3-en-2-one Diastereomer A;

Racemic 5(R,S)7(S,R)-4-(cyclohexylamino)-1-(3-fluorophenyl)-8-(3-isopropoxybenzyl)-7-methyl-1,3,8-triazaspiro[4.5]dec-3-en-2-one Diastereomer B;

Racemic 5(R,S)7(R,S)-8-benzyl-4-(cyclohexylamino)-7-methyl-1-phenyl-1,3,8-triazaspiro[4.5]dec-3-en-2-one Diastereomer A;

Racemic 5(R,S)7(S,R)-8-benzyl-4-(cyclohexylamino)-7-methyl-1-phenyl-1,3,8-triazaspiro[4.5]dec-3-en-2-one Diastereomer B;

Racemic 5(R,S)7(R,S)-8-(3-isopropoxybenzyl)-4-(isopropylamino)-7-methyl-1-(3-methylphenyl)-1,3,8-triazaspiro[4.5]dec-3-en-2-one Diastereomer A;

Racemic 5(R,S)7(S,R)-8-(3-isopropoxybenzyl)-4-(isopropylamino)-7-methyl-1-(3-methylphenyl)-1,3,8-triazaspiro[4.5]dec-3-en-2-one Diastereomer B;

5(R,S)7(R,S)-8-benzyl-4-(cyclohexylamino)-1,7-dimethyl-1,3,8-triazaspiro[4.5]dec-3-en-2-one Diastereomer A;

5(R,S)7(S,R)-8-benzyl-4-(cyclohexylamino)-1,7-dimethyl-1,3,8-triazaspiro[4.5]dec-3-en-2-one Diastereomer B; and enantiomers thereof, and pharmaceutically acceptable salts thereof.

In other preferred embodiments, the invention is directed to compounds of the invention identified in Examples 11-80, as follows:

(5R,7S)-4-(cyclohexylamino)-1-(3-fluorophenyl)-8-(3-isopropoxybenzyl)-7-methyl-1,3,8-triazaspiro[4.5]dec-3-en-2-one;

(5R,7S)-4-(cyclohexylamino)-1-(3-fluorophenyl)-7-methyl-8-(3-thienylmethyl)-1,3,8-triazaspiro[4.5]dec-3-en-2-one;

(5R,7S)-4-(cyclohexylamino)-8-(2-fluorobenzyl)-1-(3-fluorophenyl)-7-methyl-1,3,8-triazaspiro[4.5]dec-3-en-2-one;

(5R,7S)-4-(cyclohexylamino)-1-(3-fluorophenyl)-7-methyl-8-[3-(1H-pyrrol-1-yl)benzyl]-1,3,8-triazaspiro[4.5]dec-3-en-2-one;

(5R,7S)-4-(cyclohexylamino)-1-(3-fluorophenyl)-7-methyl-8-[3-(trifluoromethyl)benzyl]-1,3,8-triazaspiro[4.5]dec-3-en-2-one;

(5R,7S)-8-(3-tert-butoxybenzyl)-4-(cyclohexylamino)-1-(3-fluorophenyl)-7-methyl-1,3,8-triazaspiro[4.5]dec-3-en-2-one;

(5R,7S)-4-(cyclohexylamino)-8-[(2E)-3,7-dimethylocta-2,6-dien-1-yl]-1-(3-fluorophenyl)-7-methyl-1,3,8-triazaspiro[4.5]dec-3-en-2-one;

(5R,7S)-4-(cyclohexylamino)-1-(3-fluorophenyl)-7-methyl-8-(3-methylbut-2-en-1-yl)-1,3,8-triazaspiro[4.5]dec-3-en-2-one;

(5R,7S)-4-(cyclohexylamino)-1-(3-fluorophenyl)-7-methyl-8-[(trimethylsilyl)methyl]-1,3,8-triazaspiro[4.5]dec-3-en-2-one;

(5R,7S)-4-(cyclohexylamino)-1-(3-fluorophenyl)-7-methyl-8-[2-(trimethylsilyl)ethyl]-1,3,8-triazaspiro[4.5]dec-3-en-2-one;

(5R,7S)-4-(cyclohexylamino)-8-[3-(1-cyclopropylethoxy)benzyl]-1-(3-fluorophenyl)-7-methyl-1,3,8-triazaspiro[4.5]dec-3-en-2-one;

(5R,7S)-4-(cyclohexylamino)-1-(3-fluorophenyl)-7-methyl-8-(3-{[(1R)-1-methylpropyl]oxy}benzyl)-1,3,8-triazaspiro[4.5]dec-3-en-2-one;

(5R,7S)-4-(cyclohexylamino)-8-(2-fluoro-5-{[(1R)-1-methylpropyl]oxy}benzyl)-1-(3-fluorophenyl)-7-methyl-1,3,8-triazaspiro[4.5]dec-3-en-2-one;

(5R,7S)-4-(cyclohexylamino)-8-[3-(cyclopropylmethyl)benzyl]-1-(3-fluorophenyl)-7-methyl-1,3,8-triazaspiro[4.5]dec-3-en-2-one;

(5R,7S)-4-(cyclohexylamino)-1-(3-fluorophenyl)-7-methyl-8-[(2E)-3-methylpent-2-en-1-yl]-1,3,8-triazaspiro[4.5]dec-3-en-2-one;

(5R,7S)-4-(cyclohexylamino)-8-[3-(cyclopropyloxy)benzyl]-1-(3-fluorophenyl)-7-methyl-1,3,8-triazaspiro[4.5]dec-3-en-2-one;

(5R,7S)-4-(cyclohexylamino)-8-{3-[(1S)-1-cyclopropylethyl]benzyl}-1-(3-fluorophenyl)-7-methyl-1,3,8-triazaspiro[4.5]dec-3-en-2-one;

(5R,7S)-4-(cyclohexylamino)-8-{3-[(1R)-1-cyclopropylethyl]benzyl}-1-(3-fluorophenyl)-7-methyl-1,3,8-triazaspiro[4.5]dec-3-en-2-one;

(5R,7S)-8-(cyclohex-1-en-1-ylmethyl)-4-(cyclohexylamino)-1-(3-fluorophenyl)-7-methyl-1,3,8-triazaspiro[4.5]dec-3-en-2-one;

(5R,7S)-4-(cyclohexylamino)-8-(cyclopent-1-en-1-ylmethyl)-1-(3-fluorophenyl)-7-methyl-1,3,8-triazaspiro[4.5]dec-3-en-2-one;

(5R,7S)-4-(cyclohexylamino)-1-(3-fluorophenyl)-8-[(1-isopropyl 1H-indol-6-yl)methyl]-7-methyl-1,3,8-triazaspiro[4.5]dec-3-en-2-one;

(5R,7S)-4-(cyclohexylamino)-1-(3-fluorophenyl)-7-methyl-8-[(2-methylcyclopent-1-en-1-yl)methyl]-1,3,8-triazaspiro[4.5]dec-3-en-2-one;

(5R,7S)-4-[(1R,4R)-bicyclo[2.2.1]hept-2-ylamino]-1-(3-fluorophenyl)-7-methyl-8-(3-{[(1R)-1-methylpropyl]oxy}benzyl)-1,3,8-triazaspiro[4.5]dec-3-en-2-one;

(5R,7S)-4-[(1S,4S)-bicyclo[2.2.1]hept-2-ylamino]-1-(3-fluorophenyl)-7-methyl-8-(3-{[(1R)-1-methylpropyl]oxy}benzyl)-1,3,8-triazaspiro[4.5]dec-3-en-2-one;

(5R,7S)-4-(cyclobutylamino)-1-(3-fluorophenyl)-7-methyl-8-(3-{[(1S,2R)-2-methylcyclopropyl]oxy}benzyl)-1,3,8-triazaspiro[4.5]dec-3-en-2-one;

(5R,7S)-4-(cyclobutylamino)-1-(3-fluorophenyl)-7-methyl-8-(3-{[(1R,2S)-2-methylcyclopropyl]oxy}benzyl) 1,3,8-triazaspiro[4.5]dec-3-en-2-one;

(5R,7S)-8-(cyclopentylmethyl)-4-{[(1S,2S)-2-fluorocyclohexyl]amino}-1-(3-fluorophenyl)-7-methyl-1,3,8-triazaspiro[4.5]dec-3-en-2-one;

(5R,7S)-8-(cyclopentylmethyl)-4-{[(1R,2R)-2-fluorocyclohexyl]amino}-1-(3-fluorophenyl)-7-methyl-1,3,8-triazaspiro[4.5]dec-3-en-2-one;

(5R,7S)-4-(cyclopentylamino)-1-(3-fluorophenyl)-8-(3-isopropoxybenzyl)-7-methyl-1,3,8-triazaspiro[4.5]dec-3-en-2-one;

(5R,7S)-8-benzyl-1-(3-fluorophenyl)-7-methyl-4-(spiro[2.5]oct-6-ylamino)-1,3,8-triazaspiro[4.5]dec-3-en-2-one;

(5R,7S)-1-(3-fluorophenyl)-8-(3-isopropoxybenzyl)-7-methyl-4-{[(5S,6R)-6-phenylspiro[2.4]hept-5-yl]amino}-1,3,8-triazaspiro[4.5]dec-3-en-2-one;

(5R,7S)-1-(3-fluorophenyl)-8-(3-isopropoxybenzyl)-7-methyl-4-{[(5R,6S)-6-phenylspiro[2.4]hept-5-yl]amino}-1,3,8-triazaspiro[4.5]dec-3-en-2-one;

(5R,7S)-4-[(4,4-difluorocyclohexyl)amino]-1-(3-fluorophenyl)-8-(3-isopropoxybenzyl)-7-methyl-1,3,8-triazaspiro[4.5]dec-3-en-2-one;

(5R,7S)-8-benzyl-4-[(4,4-difluorocyclohexyl)amino]-1-(3-fluorophenyl)-7-methyl-1,3,8-triazaspiro[4.5]dec-3-en-2-one;

(5R,7S)-8-(cyclobutylmethyl)-4-{[(3R)-1,1-dimethylsilolan-3-yl]amino}-1-(3-fluorophenyl)-7-methyl-1,3,8-triazaspiro[4.5]dec-3-en-2-one;

(5R,7S)-8-(cyclobutylmethyl)-4-{[(3S)-1,1-dimethylsilolan-3-yl]amino}-1-(3-fluorophenyl)-7-methyl-1,3,8-triazaspiro[4.5]dec-3-en-2-one;

(5R,7S)-8-(cyclobutylmethyl)-4-{[(1R,2R)-2-fluorocyclohexyl]amino}-1-(3-fluorophenyl)-7-methyl-1,3,8-triazaspiro[4.5]dec-3-en-2-one;

(5R,7S)-8-(cyclobutylmethyl)-4-{[(1S,2S)-2-fluorocyclohexyl]amino}-1-(3-fluorophenyl)-7-methyl-1,3,8-triazaspiro[4.5]dec-3-en-2-one;

(5R,7S)-4-{[(1R)-1,2-dimethylpropyl]amino}-1-(3-fluorophenyl)-7-methyl-8-(3-methylbut-2-en-1-yl)-1,3,8-triazaspiro[4.5]dec-3-en-2-one;

(5R,7S)-4-{[(1S)-1,2-dimethylpropyl]amino}-1-(3-fluorophenyl)-7-methyl-8-(3-methylbut-2-en-1-yl)-1,3,8-triazaspiro[4.5]dec-3-en-2-one;

(5R,7S)-1-(3-chlorophenyl)-8-(cyclobutylmethyl)-4-(cyclohexylamino)-7-methyl-1,3,8-triazaspiro[4.5]dec-3-en-2-one;

(5R,7S)-1-(3-bromophenyl)-8-(cyclobutylmethyl)-4-(cyclohexylamino)-7-methyl-1,3,8-triazaspiro[4.5]dec-3-en-2-one;

(5R,7S)-4-(cyclohexylamino)-1-(3-fluorophenyl)-8-(3-isopropoxybenzyl)-7-methyl-1,3,8-triazaspiro[4,5]dec-3-ene-2-thione;

(5R,7S)-4-(cyclohexylamino)-8-[(2,2-dimethyl-1,2-dihydroquinolin-8-yl)methyl]-1-(3-fluorophenyl)-7-methyl-1,3,8-triazaspiro[4.5]dec-3-en-2-one;

(5R,7S)-4-(cyclohexylamino)-8-[(2,2-dimethyl-1,2,3,4-tetrahydroquinolin-8-yl)methyl]-1-(3-fluorophenyl)-7-methyl-1,3,8-triazaspiro[4.5]dec-3-en-2-one;

(5R,7R)-4-(cyclohexylamino)-1-(3-fluorophenyl)-8-(3-isopropoxybenzyl)-7-vinyl-1,3,8-triazaspiro[4.5]dec-3-en-2-one;

(5R,7R)-8-benzyl-4-(cyclohexylamino)-1-(3-fluorophenyl)-7-vinyl-1,3,8-triazaspiro[4.5]dec-3-en-2-one;

(5R,7R)-4-(cyclohexylamino)-1-(3-fluorophenyl)-8-(3-{[(1R)-1-methylpropyl]oxy}benzyl)-7-vinyl-1,3,8-triazaspiro[4.5]dec-3-en-2-one;

(5R,7R)-4-(cyclohexylamino)-1-(3-fluorophenyl)-8-(3-isopropoxybenzyl)-7-[(1E)-prop-1-en-1-yl]-1,3,8-triazaspiro[4.5]dec-3-en-2-one;

(5R,7R)-4-(cyclohexylamino)-1-(3-fluorophenyl)-8-(3-isopropoxybenzyl)-7-[(1Z)-prop-1-en-1-yl]-1,3,8-triazaspiro[4.5]dec-3-en-2-one;

(5R,7S)-1-(3-fluorophenyl)-7-methyl-4-(methylamino)-8-[(2'-methylbiphenyl-3-yl)methyl]-1,3,8-triazaspiro[4.5]dec-3-en-2-one;

(5R,7S)-8-(cyclobutylmethyl)-4-(cyclohexylamino)-1-[4'-(isopropylsulfonyl)biphenyl-2-yl]-7-methyl-1,3,8-triazaspiro[4.5]dec-3-en-2-one;

(5R,7S)-8-benzyl-4-(cyclohexylamino)-1-(cyclopropylmethyl)-7-methyl-1,3,8-triazaspiro[4.5]dec-3-en-2-one;

(5R,7S)-(5S,7R)-8-benzyl-4-(cyclohexylamino)-1-cyclopropyl-7-methyl-1,3,8-triazaspiro[4.5]dec-3-en-2-one;

(5R,7S)-(5S,7R)-8-benzyl-1-cyclobutyl-4-(cyclohexylamino)-7-methyl-1,3,8-triazaspiro[4.5]dec-3-en-2-one;

(5R,7S)-(5S,7R)-8-benzyl-4-(cyclohexylamino)-1-cyclopentyl-7-methyl-1,3,8-triazaspiro[4.5]dec-3-en-2-one;

(5R,7S)-(5S,7R)-8-benzyl-1-cyclohexyl-4-(cyclohexylamino)-7-methyl-1,3,8-triazaspiro[4.5]dec-3-en-2-one;

(5R,7S)-(5S,7R)-8-benzyl-4-(cyclohexylamino)-7-methyl-1-(2-methylprop-2-en-1-yl)-1,3,8-triazaspiro[4.5]dec-3-en-2-one;

(5R,7S)-(5S,7R)-8-benzyl-4-(cyclohexylamino)-7-methyl-1-(tetrahydrofuran-3-yl)-1,3,8-triazaspiro[4.5]dec-3-en-2-one;

(5R,7S)-1-(3-fluorophenyl)-8-(3-isopropoxybenzyl)-7-methyl-4-{[(3S)-1-(methylsulfonyl)pyrrolidin-3-yl]amino}-1,3,8-triazaspiro[4.5]dec-3-en-2-one;

(5R,7S)-4-[(3,3-difluorocyclohexyl)amino]-1-(3-fluorophenyl)-8-(3-isopropoxybenzyl)-7-methyl-1,3,8-triazaspiro[4.5]dec-3-en-2-one;

(5R,7S)-(5S,7R)-4-[(2-fluoro-1-methylethyl)amino]-1-3-fluorophenyl)-8-(3-isopropoxybenzyl)-7-methyl-1,3,8-triazaspiro[4.5]dec-3-en-2-one;

(5R,7S)-(5S,7R)-4-{[(1S)-1,2-dimethylpropyl]amino}-1-(3-fluorophenyl)-8-(3-isopropoxybenzyl)-7-methyl-1,3,8-triazaspiro[4.5]dec-3-en-2-one;

(5R,7S)-4-{[(1R,2R)-2-fluorocyclohexyl]amino}-1-(3-fluorophenyl)-8-(3-isopropoxybenzyl)-7-methyl-1,3,8-triazaspiro[4.5]dec-3-en-2-one;

(5R,7S)-4-{[(1S,2S)-2-fluorocyclohexyl]amino}-1-(3-fluorophenyl)-8-(3-isopropoxybenzyl)-7-methyl-1,3,8-triazaspiro[4.5]dec-3-en-2-one;

(5R,7S)-1-(3-fluorophenyl)-8-(3-isopropoxybenzyl)-4-[(2-isopropylcyclopropyl)amino]-7-methyl-1,3,8-triazaspiro[4.5]dec-3-en-2-one;

(5R,7S)-4-{[(1R,2R)-2-fluorocyclopentyl]amino}-1-(3-fluorophenyl)-8-(3-isopropoxybenzyl)-7-methyl-1,3,8-triazaspiro[4.5]dec-3-en-2-one;

(5R,7S)-4-{[(1S,2S)-2-fluorocyclopentyl]amino}-1-(3-fluorophenyl)-8-(3-isopropoxybenzyl)-7-methyl-1,3,8-triazaspiro[4.5]dec-3-en-2-one;

(5R,7S)-1-(3-fluorophenyl)-8-(3-isopropoxybenzyl)-7-methyl-4-[(2-propylcyclopropyl)amino]-1,3,8-triazaspiro[4.5]dec-3-en-2-one;

(5R,7S)-4-{[(1R)-2,2-difluorocyclohexyl]amino}-1-(3-fluorophenyl)-8-(3-isopropoxybenzyl)-7-methyl-1,3,8-triazaspiro[4.5]dec-3-en-2-one;

(5R,7S)-4-{[(1S)-2,2-difluorocyclohexyl]amino}-1-(3-fluorophenyl)-8-(3-isopropoxybenzyl)-7-methyl-1,3,8-triazaspiro[4.5]dec-3-en-2-one;

(5R,7S)-4-{[(1R)-2,2-difluorocyclopentyl]amino}-1-(3-fluorophenyl)-8-(3-isopropoxybenzyl)-7-methyl-1,3,8-triazaspiro[4.5]dec-3-en-2-one;

(5R,7S)-4-{[(1S)-2,2-difluorocyclopentyl]amino}-1-(3-fluorophenyl)-8-(3-isopropoxybenzyl)-7-methyl-1,3,8-triazaspiro[4.5]dec-3-en-2-one;

(5R,7S)-4-{[(1R,2S)-2-fluorocyclohexyl]amino}-1-(3-fluorophenyl)-8-(3-isopropoxybenzyl)-7-methyl-1,3,8-triazaspiro[4.5]dec-3-en-2-one;

(5R,7S)-4-{[(1S,2R)-2-fluorocyclohexyl]amino}-1-(3-fluorophenyl)-8-(3-isopropoxybenzyl)-7-methyl-1,3,8-triazaspiro[4.5]dec-3-en-2-one;

(5R,7S)-8-benzyl-1-(3-fluorophenyl)-7-methyl-4-{[(1S)-1,2,2-trimethylpropyl]amino}-1,3,8-triazaspiro[4.5]dec-3-en-2-one;

(5R,7S)-4-(cyclohexylimino)-1-(3-fluorophenyl)-8-(3-isopropoxybenzyl)-3,7-dimethyl-1,3,8-triazaspiro[4.5]decan-2-one; and pharmaceutically acceptable salts thereof.

The invention is also directed to methods of treating a patient (preferably a human) for diseases in which the β-secretase enzyme is involved, such as Alzheimer's disease, by administering a therapeutically effective amount of a spiropiperidine compound of formula (I), (I'), (II), (II'), (III), (III'), (IV) or (IV') or a pharmaceutically acceptable salt thereof, and a pharmaceutically acceptable carrier.

The invention is also directed to methods of inhibiting BACE1 enzyme activity, by administering a therapeutically effective amount of a spiropiperidine compound of formula (I), (I'), (II), (II'), (O), (III'), (IV) or (IV'), or a pharmaceutically acceptable salt thereof, and a pharmaceutically acceptable carrier, to a mammal or patient in need thereof. In another embodiment, the invention is directed to methods of inhibiting BACE2 enzyme activity, by administering a therapeutically effective amount of a spiropiperidine compound of formula (I), (I'), (II), (II'), (III), (III'), (IV) or (IV'), or a pharmaceutically acceptable salt thereof, and a pharmaceutically acceptable carrier, to a mammal or patient in need thereof.

The invention is also directed to methods of treating a patient (preferably a human) for diseases in which the β-secretase enzyme is involved, such as Alzheimer's disease, by administering a therapeutically effective amount of a spiropiperidine compound of formula (I), (I'), (II), (II'), (III), (III'), (IV) or (IV'), or a pharmaceutically acceptable salt thereof, in combination with a P450 inhibitor, such as ritonavir, and a pharmaceutically acceptable carrier.

The invention is also directed to pharmaceutical compositions for the treatment of diseases in a patient (preferably a human) in which the β-secretase enzyme is involved, such as Alzheimer's Disease, which include a therapeutically effective amount of a compound of formula (I), (I'), (II), (II'), (III), (III'), (IV) or (IV') or a pharmaceutically acceptable salt thereof, and a pharmaceutically acceptable carrier.

The invention is also directed to pharmaceutical compositions for the treatment of diseases in mammals (preferably humans) in which the β-secretase enzyme is involved, such as Alzheimer's Disease, which include a therapeutically effective amount of a compound of formula (I), (I'), (II), (II'), (III), (III'), (IV) or (IV'), or a pharmaceutically acceptable salt thereof, together with a P450 inhibitor, such as ritonavir, and a pharmaceutically acceptable carrier.

As used herein, the term "alkyl," by itself or as part of another substituent, means a saturated straight or branched chain hydrocarbon radical having the number of carbon atoms designated (e.g., $C_{1-10}$alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkylene," by itself or as part of another substituent, means a saturated straight or branched chain divalent hydrocarbon radical having the number of carbon atoms designated.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "heterocyclic," by itself or as part of another substituent, means a cycloalkyl group as defined above, in which one or more of the ring carbon atoms is replaced with a heteroatom (such as N, S or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. Preferred heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Preferably, the substituent is bonded to a ring carbon atom. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment. Preferably, the attachment is at a ring carbon atom.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. The preferred single ring aryl group for use in the invention is phenyl. Preferred fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems, and includes multiple ring systems wherein part of the molecule is aromatic and part is non-aromatic. Preferred heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl and benzoxazolyl. More preferred heteroaryl groups include indolyl, thienyl, pyridinyl, dihydroquinolinyl and tetrahydroquinolinyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of the invention have at least two asymmetric centers. Additional asymmetric centers may be present depending upon the nature of the various substituents on the molecule.

For example, for the compounds of formula (I) and (I'), the 5-carbon and 7-carbon of the spiropiperidine ring are chiral. As a result, the compounds of formula (I) may be present as two racemic diastereomers, or in four stereochemically pure forms. The diastereomeric forms for compounds of formula (I) are depicted below, as diastereomers (IA) (diastereomer A), where the amine of the spiro center and the $R^4$ group are cis to one another, and (IB) (diastereomer B), where the amine of the spiro center and the $R^4$ group are trans to one another.

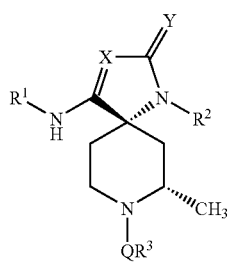
(IA)

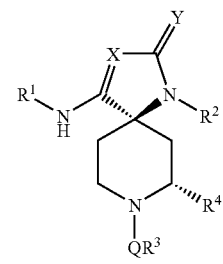
(IB)

When $R^4$ is methyl or ethyl, the diastereomer (IA) is the 5(S,R),7(S,R) configuration, the diastereomer (IB) is the 5(R,S),7(S,R) configuration. An alternative convention is to refer to diastereomer IA as having the (5S,7S) (5R,7R) configuration, and to refer to diastereomer IB as having the (5R,7S) (5S,7R) configuration.

Each of (IA) and (IB) may be present in tautomeric form, as shown below as (IA') and (IB'):

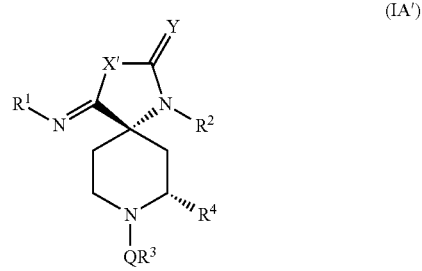
(IA')

or

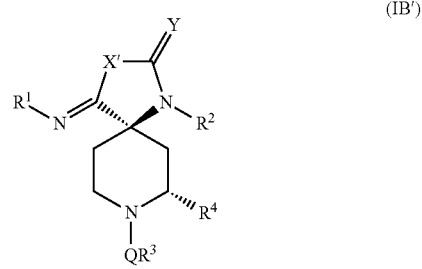
(IB')

In a preferred embodiment, the compounds of the invention are compounds of formula (IB) and its tautomer (IB').

The compounds of each of formulas (II), (II'), (III), (III'), (IV) and (IV') are also present as diastereomeric forms, as diastereomers (IIA), (IIIA) and (IVA), where the amine of the spiro center and the $R^4$ group are cis to one another, and diastereomers (IIB), (IIIB) and (IVB), where the amine of the spiro center and the $R^4$ group are trans to one another. In a preferred embodiment, the compounds of formulas (II), (II'), (III), (III'), (IV) and (IV') are present as the diastereomeric forms (IIB), (IIIB) and (IVB), and their respective tautomers, as depicted below:

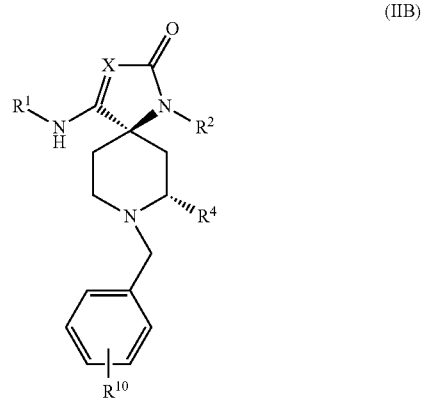
(IIB)

or its tautomer (IIB')

(IIB')
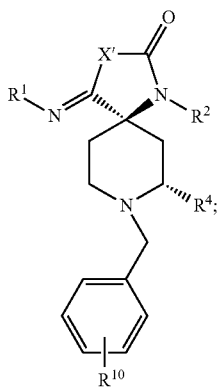

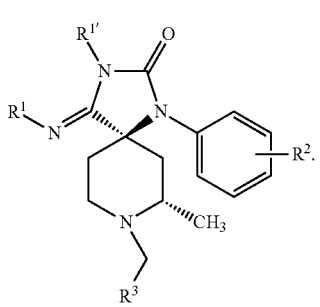
(IVB')

In addition, each of (IA) and (IB) may be present as a racemic mixture, or in one of two enantiomeric forms, as shown below with compound (IA), as compounds (IA) and (IA*):

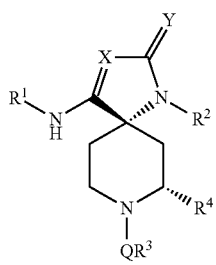
(IA)

or (IIIB)
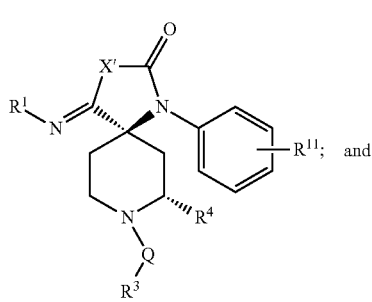

or its tautomer (IIIB')

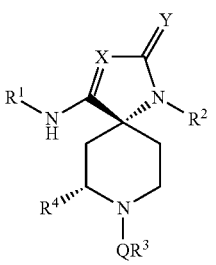
(IA*)

(IIIB')

wherein when $R^4$ is methyl or ethyl, the enantiomer IA is the 5(S),7(S) configuration and the enantiomer IA* is the 5(R),7(R) configuration.

Similarly, compounds of formula IB may exist as the separate enantiomeric compounds IB and IB*

(IVB)
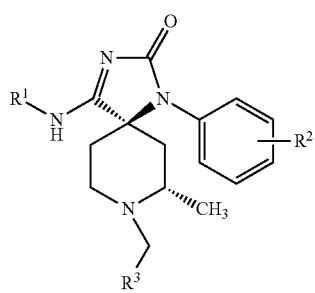

or its tautomer (IVB')

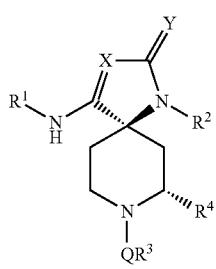
(IB)

or

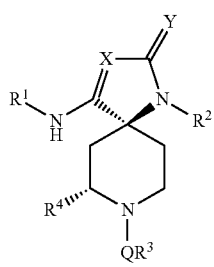

(IB*)

wherein when R⁴ is methyl or ethyl, the enantiomers IIB is the 5(R),7(S) configuration and the enantiomers IB* is the 5(S), 7(R) configuration.

In a preferred enantiomeric embodiment, the compounds of the invention are compounds of formula (IB).

Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other configurational isomers. The present invention includes all such possible isomers as well as mixtures of such isomers.

Formulas (I), (I'), (II), (II'), (III), (III'), (IV) or (IV') are shown above without a definite stereochemistry at certain positions. The present invention includes all stereoisomers of formulas (I), (I'), (II), (II'), (III), (III'), (IV) or (IV') and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

As used herein, the term "tautomer" refers to a compound which exists in an equilibrium mixture and which can be isolated in either form and react through either form. The tautomers may differ in linkage, bond, or connections between atoms, and the position or distribution of the atoms in the molecule. One common form of tautomerism occurs when an enamine group, for example a group $R_2C=CR-NHR$, exists in equilibrium with its tautomeric imine form, for example $R_2CH-CR=NR$. In the context of this invention, compounds of formula (I) may be present in the enamine form as shown below:

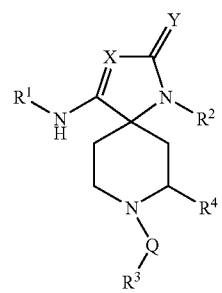

(I)

and pharmaceutically acceptable salts thereof, and individual enantiomers and diastereomers thereof, wherein X, Q, R¹, R², R³ and R⁴ are as defined above, or in the tautomeric imine form (I'), as shown below:

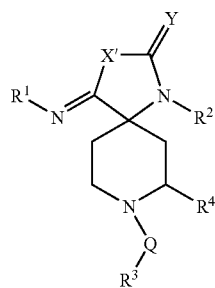

(I')

and pharmaceutically acceptable salts thereof, and individual enantiomers and diastereomers thereof, wherein X', Q, R¹, R², R³ and R⁴ are as defined above.

The compounds claimed in this invention can be prepared according to the following general procedure methods.

General Scheme 1 depicts a method for preparing 1-benzyl-2-methylpiperidin-4-one intermediates useful for making compounds of the invention. The commercially available 1-1 may be alkylated with an appropriate alkyl halide like benzyl chloride using a suitable base like potassium carbonate in a suitable solvent like acetonitrile. A similar method is described by M. E. Kopach et. al. J. Org. Chem. 2003 68 5739-5741.

General Scheme 1

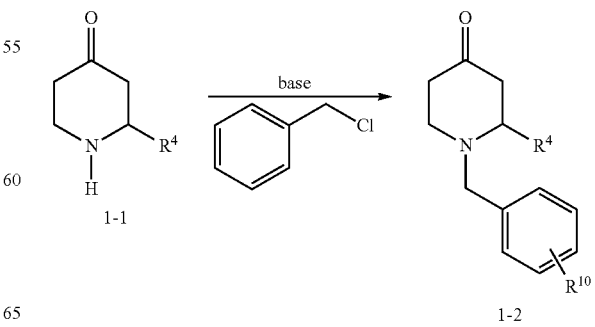

Alternatively, as shown below in General Scheme 2, an intermediate like 1-2 may be prepared using a procedure similar to the one outlined in J. Blanco-Pilado et al, in WO2004/094380. Vinyl trimethylsilane and an acyl chloride are condensed with AlCl₃ to give an intermediate that is then reacted with an amine like benzylamine to give the alkylated piperidinone 1-2.

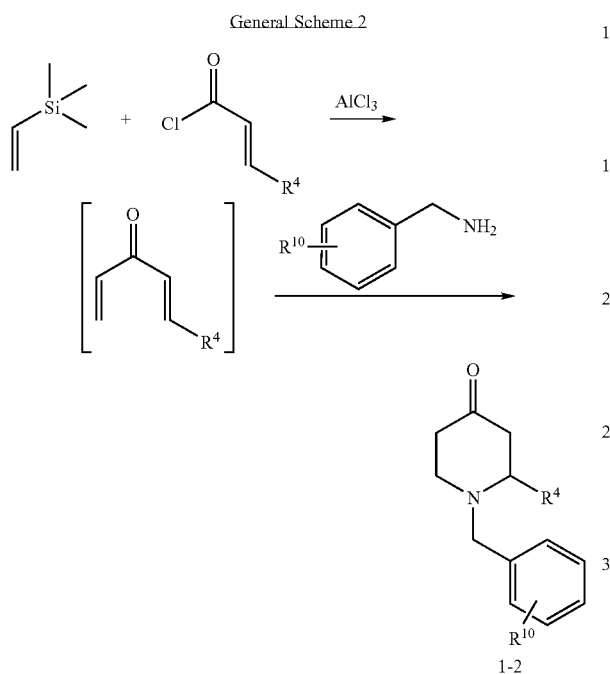

General Scheme 3 below depicts a four-component coupling reaction between a piperidinone derivative, amine, isonitrile, and cyantate, which assembles the core structure 3-1. A similar method is described in Chung et al, U.S. Pat. No. 5,221,675. Further elaboration of 3-1 is possible, for example, by removal of a temporary R³ group to give 3-2, followed by alkylation with a different R³ to give new structure 3-3, using methods similar to that described above for 1-1.

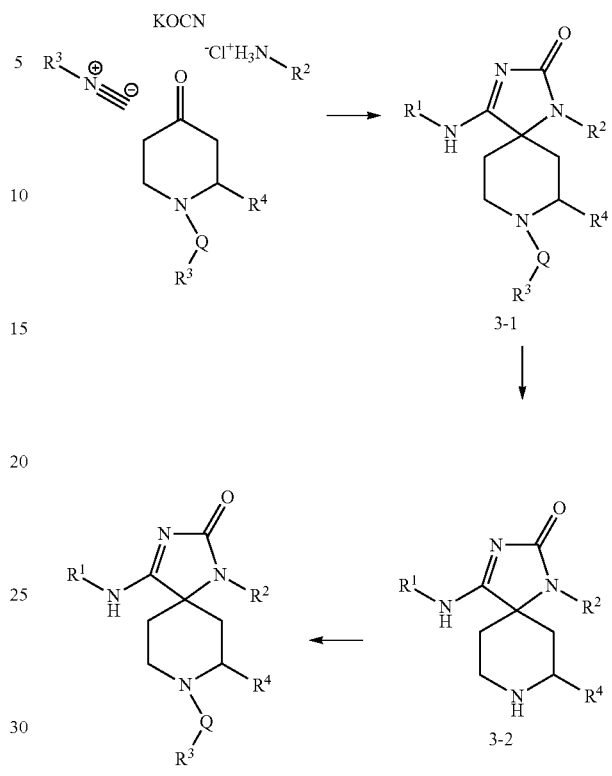

General Scheme 4 depicts the formation of compounds of the invention where X/X' CR⁵/CR⁵R⁵'. Similar to methods found in R. Jones et al, *Tetrahedron Letters*, 24 (43), 1983, 4751-4754, Strecker reaction on a suitably substituted intermediate 1-1 gives nitrile 4-1, which can be acylated to give 42 and then cyclized to 4-3 by first treatment with a base like NaOMe followed by treatment with a strong aqueous acid like 6 N HCl. 4-3 may then be treated with a suitable amine to give 4-4 and substituted with a fluorine to give 4-5 upon treatment with a fluorinating agent.

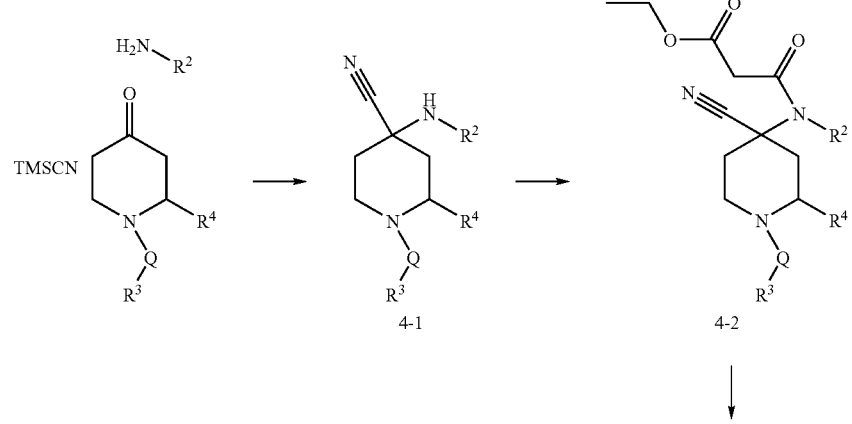

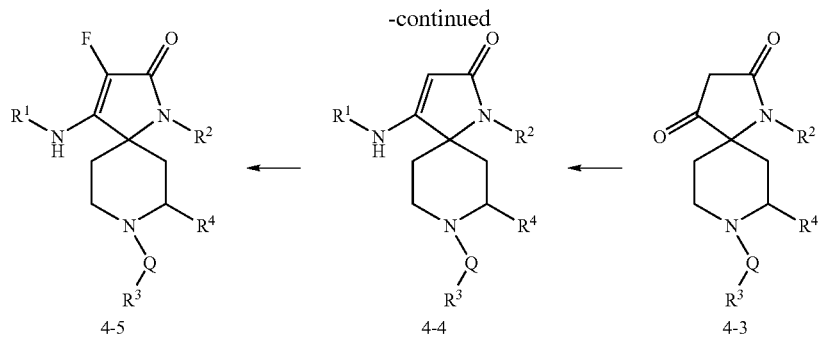

General Scheme 5 depicts an alternative route that allows the formation of compounds of the invention where $R^1$ may be varied toward the end of the synthesis. Similar to methods found in P. L. Feldman et al, *J. Org. Chem.* 1990 55, 4207, 1983, 4751-4754, Strecker reaction on a suitably substituted intermediate 1-1 gives nitrile 5-1, which can be deprotected to give the unsubstituted piperidine 5-2 and then derivitized in a manner similar to that described for 1-2 to give nitrile 5-3. 5-3 may be acylated to give 54 and then cyclized to 5-5 by treatment with water. 5-5 may then be treated with a sulfur source like hydrogen sulfide to give 5-6 and then reacted with a suitable amine to give 5-7.

General Scheme 5

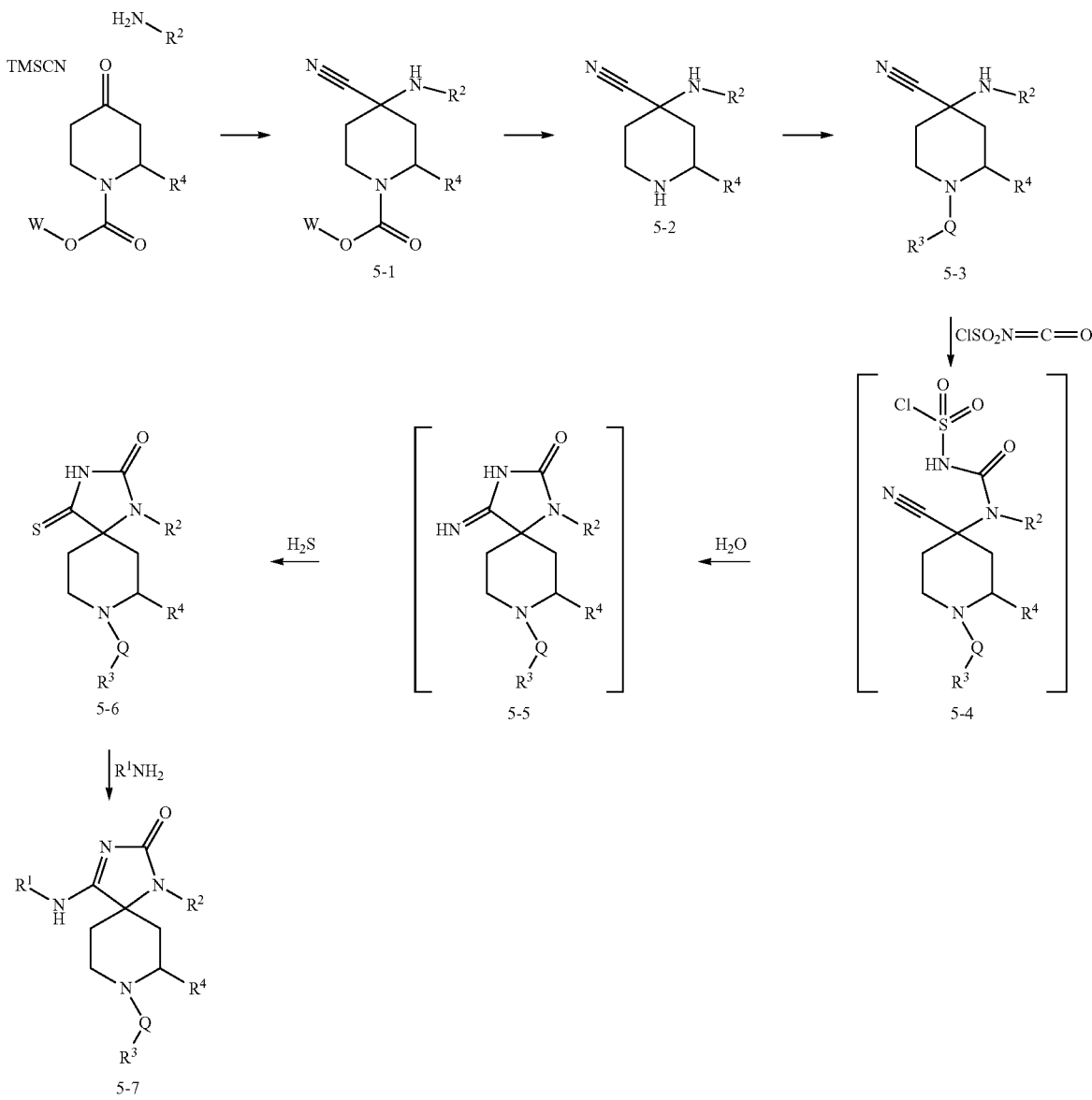

General Scheme 5a depicts a similar route that allows the formation of compounds of the invention where $R^1$ may be varied toward the end of the synthesis. Here the nitrile 5-3 may be acylated to give 5a-1 and then cyclized to 5a-2 by treatment with water. 5a-2 may then be directly reacted with a suitable amine to give 5a-3.

General Scheme 5a

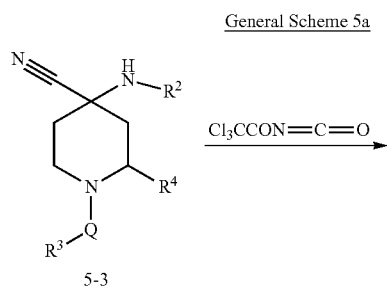

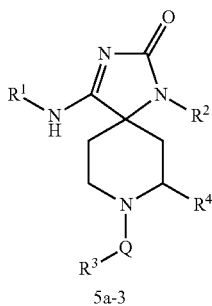

5a-3

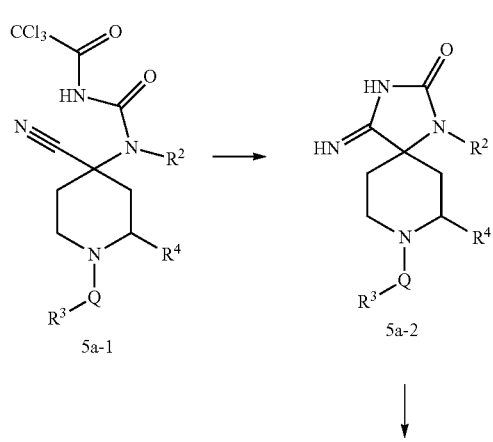

General Scheme 5b depicts an alternative route that allows the formation of compounds of the invention where $R^2$ is substituted with additional groups. Similar to methods found in P. L. Feldman et al, *J. Org. Chem.* 1990 55, 4207, 1983, 4751-4754, Strecker reaction on a suitably substituted biphenylanaline gives nitrile 5b-1, which can be acylated to give 5b-2 and then cyclized to 5b-3 by treatment with water. Addition of a suitably substituted $R^1$amine then gives 5b-4, which can be deprotected and derivitized on the piperidine nitrogen with a suitable QR3 group as described above.

General Scheme 5b

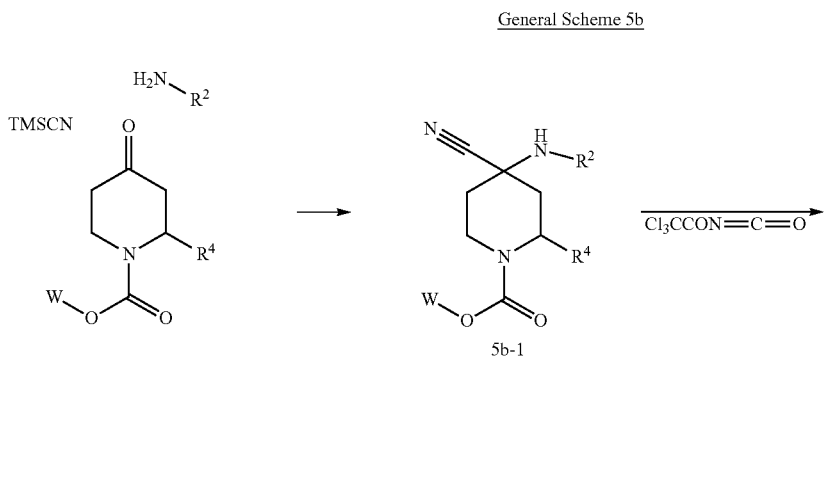

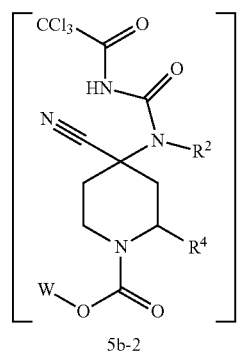

5b-2

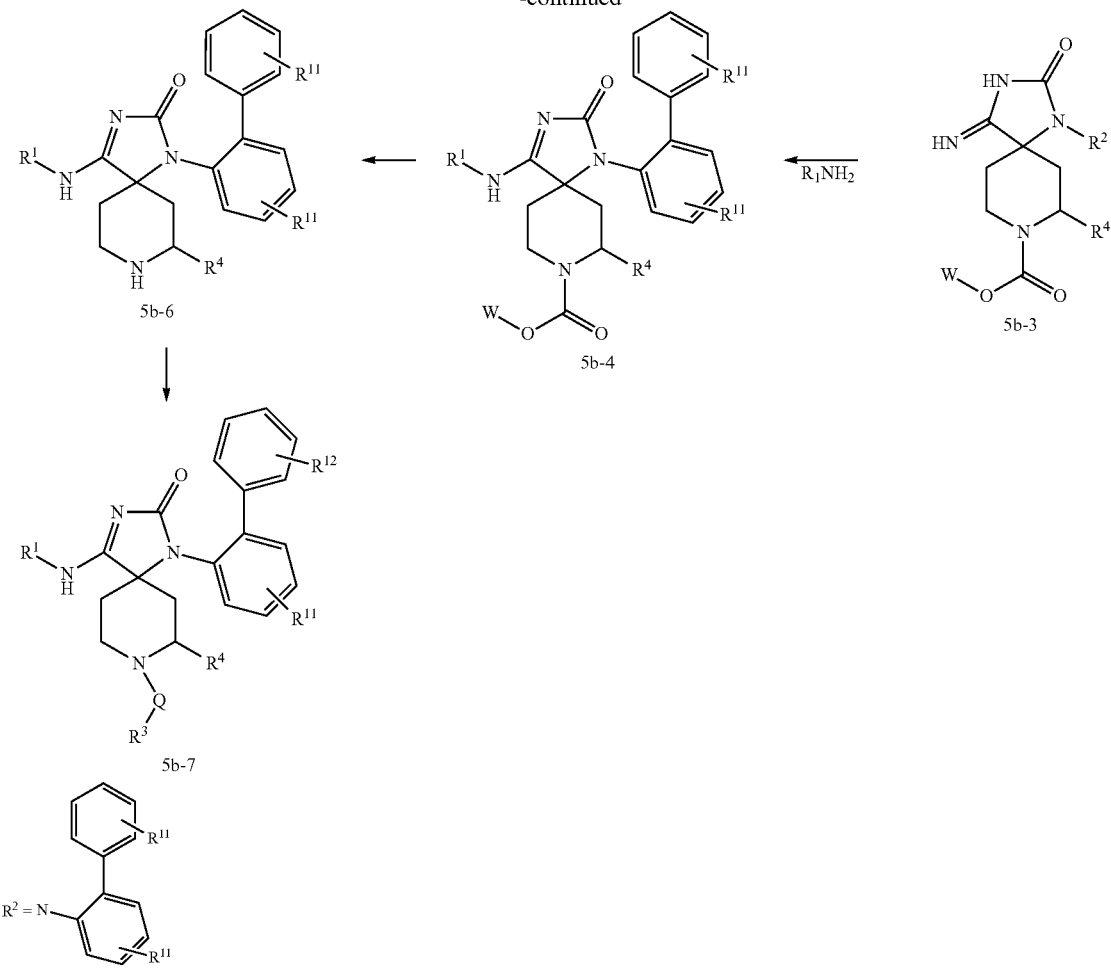

General Scheme 6 depicts an alternative route, which allows the formation of compounds of the invention where $R^3$ is substituted with additional groups. Preparation similar to that outlined above allows formation of the bromo-substituted intermediate 6-1, which may be coupled with a suitable boronic acid using a suitable catalyst like palladium acetate and a suitable ligand like 3,3',3''-Phosphinidynetris(benzene sulfonic acid). Alternatively, the boronic acid intermediate 6-3 may be reacted with an appropriate aryl halide under the same type of conditions to give 6-2.

General Scheme 6

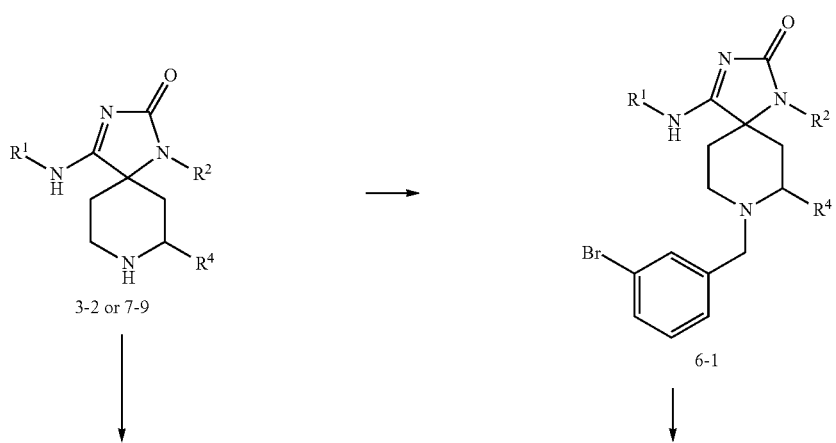

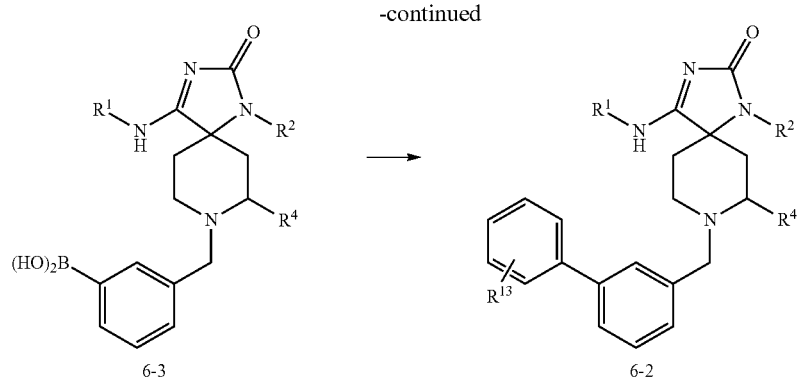

General Scheme 7 depicts an alternative route, which allows efficient variation of $R^1$ and $QR^3$ groups in compounds of the invention. In this scheme, a piperidinone protected with a suitable removable protecting group like CBZ (where W is $CH_2$-phenyl) can take part in a Strecker reaction in the presence of $Zn(CN)_2$ to give the desired stereoisomeric Strecker product as the major isomer. Alternatively, the Strecker reaction similar to that described by J. Cossy in *Synthesis* 1995 11 1368-1370 may be done with TMSCN/HOAC and the resulting mixture of diastereomeric products can be treated with TMSCN in EtOH with heat to equilibrate the mixture so that the major isomer is the desired one. Acylation with a suitable agent like trichloroacetylisocyanate followed by cyclization with methanol/water in a procedure similar to that described by R. Sarges, et. al. in *JOC* 1982, 47 4081-4085 leads to the isolable intermediate iminohydantoin 7-6 that can be converted directly to the $R^1$ substituted intermediate 7-8 by heating with a suitable amine. The nitrogen protecting group may then be removed and a suitable alkylating agent with a suitable base like potassium carbonate may used to incorporate the $QR^3$ substituent.

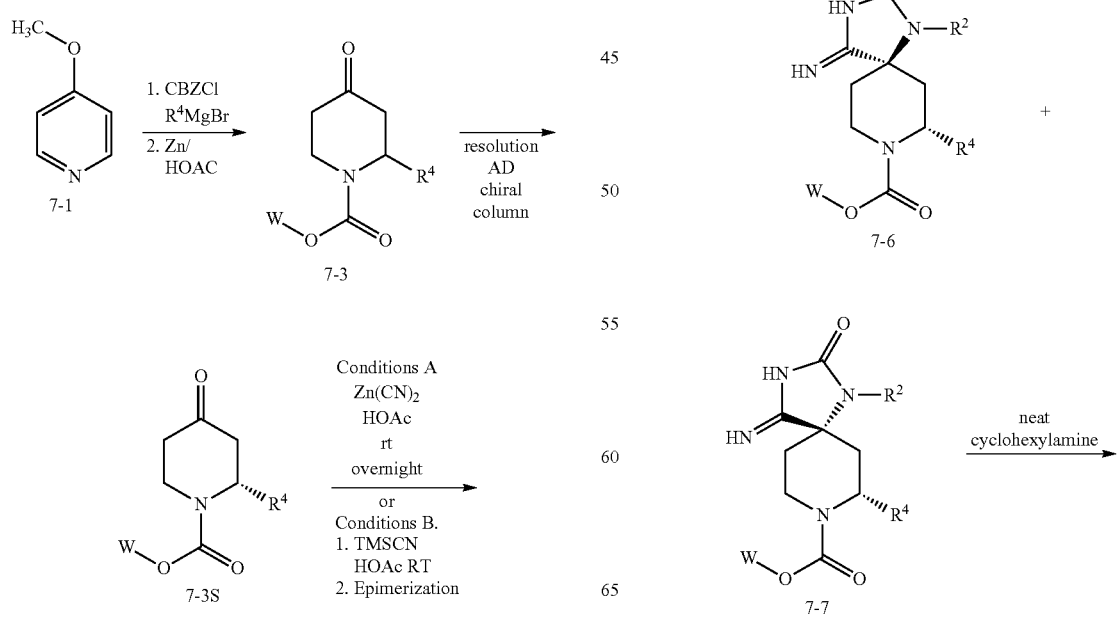

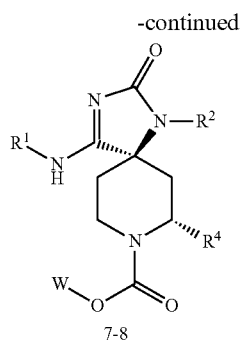

7-8

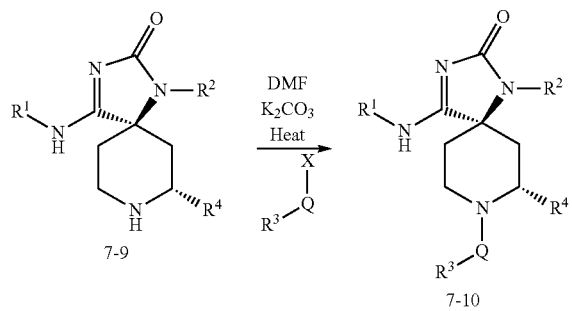

7-9　　7-10

General Scheme 8 depicts an alternative route to the preparation of compounds of the invention utilizing a sulfur-containing reagent like thiocyanate in the Ugi reaction similar to conditions described by I. Ugi et. al. *Ann.* 1963, 666 54-61 to give the thiohydantoin 8-2, and then conversion of 8-2 to the iminohydantoin 8-3 in a manner similar to that described by K. Senga et. al. *Chem. Pharm. Bull.* 26(3) 765-769 by activation with thionyl chloride followed by reaction with a suitable alcohol like methanol and acid like acetic acid.

General Scheme 8

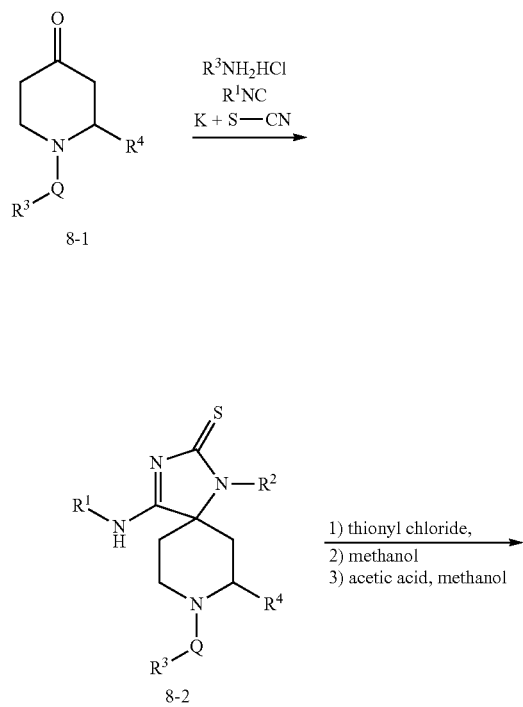

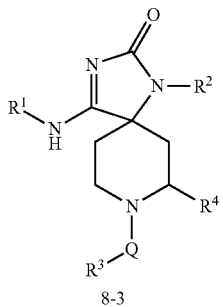

8-3

The term "substantially pure" means that the isolated material is at least 90% pure, and preferably 95% pure, and even more preferably 99% pure as assayed by analytical techniques known in the art.

By "pharmaceutically acceptable" it is meant the carrier, diluent or excipient must be compatible with the other ingredients of the formulation and not deleterious to the recipient thereof.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred salts are the sulfate, phosphate, citrate, malate, mandelate, hippurate, trifluoroacetate and hydrochloric acid salts.

The present invention is directed to the use of the compounds of formulas (I), (I'), (II), (II'), (III), (III'), (IV) or (IV') disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, dementia associated with Parkinson's Disease, progressive supranuclear palsy, head trauma, stroke, pancreatitis, inclusion body myositis, other peripheral amyloidoses, diabetes and atherosclerosis. The compounds may also be useful in enhancing cognition in patients suffering from diseases mediated by abnormal cleavage of the amyloid precursor protein.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors; glycine transport inhibitors; alpha 7 nicotinic agonists, such as SSR 180711, MEM3454 and MEM63908; gamma-secretase inhibitors, such as LY450139, LY411575 and TAK 070; gamma secretase modulators, such as E2012; tau phosphorylation inhibitors; blockers of Aβ oligomer formation; 5-HT4 agonists, such as PRX 03140; 5HT6 antagonists, such as GSK 742457, SGS-518, SAM315, E6795, SL-65.0155, SRA-333 and xaliproden; p25/CDK5 inhibitors; HMG-CoA reductase inhibitors; NK1/NK3 receptor antagonists; NSAID's including ibuprofen; vitamin E; anti-amyloid antibodies (including anti-amyloid humanized monoclonal antibodies), such as bapineuzumab, AAB002, RN1219, ACC001, CAD106 and AZD3102; 5-HT1A antagonists, such as lecozotan; COX-2 inhibitors; anti-inflammatory compounds, such as (R)-flurbiprofen, nitroflurbiprofen, rosiglitazone, ND-1251, VP-025, HT-0712 and EHT-202; CB-1 receptor antagonists or CB-1 receptor inverse agonists, such as AVE 1625; antibiotics such as doxycycline and rifampin; N-methyl-D-aspartate (NMDA) receptor antagonists, such as memantine, neramexane and EVT 101; NR2B antagonists; androgen receptor modulators; acetylcholinesterase inhibitors such as galantamine, rivastigmine, donepezil, tacrine, phenserine, ladostigil and ABT-089; mGluR5 modulators; growth hormone secretagogues such as ibutamoren, ibutamoren mesylate, and capromorelin; histamine $H_3$ receptor antagonists, such as ABT834, ABT239, GSK 189254 and CEP16795; AMPA agonists or AMPA modulators, such as CX717, LY404187 and S-18986; PDE IV inhibitors, such as MEM141, HT0712 and AVE8112; $GABA_A$ inverse agonists; $GABA_A$ α 5 receptor ligands; $GABA_B$ receptor ligands; potassium channel blockers; neuronal nicotinic agonists, such as ABT089; plasminogen activator inhibitors, such as PAZ417; cathepsin B inhibitors; GSK3β inhibitors, such as AZD1080, SAR502250 and CEP 16805; selective M1 agonists; neuronal nicotinic agonists, microtubule affinity regulating kinase (MARK) ligands; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The compounds of the invention, like many protease inhibitors, are believed to be metabolized in vivo by cytochrome P-450 monooxygenase. Cytochrome P-450 is a family of isozymes which impact drug metabolism. Cytochrome P-450 isozymes (including the CYP3A4 isozyme) transform drug molecules in vivo, typically via oxidation. Metabolism by cytochrome P-450 often leads to unfavorable pharmacokinetics, and the need for more frequent and higher doses than are desirable. Administration of such drugs with an agent that inhibits metabolism by cytochrome P-450 may improve the pharmacokinetics (i.e., increase half-life, increase time to peak plasma concentration, increase blood levels) of the drug.

In one embodiment, the invention is directed to the combination or co-administration of a compound of the invention and a cytochrome P-450 inhibitor. The invention is also directed to a method for improving the pharmacokinetics of a compound of the invention which is metabolized by cytochrome P-450 monooxygenase, by administering a compound of the invention with a cytochrome P-450 inhibitor.

The combination of a P-450 inhibitor and a compound of the invention may be administered as part of a unit dosage form combination product, or as a kit or treatment protocol wherein one or more P-450 inhibitors are administered in separate dosage forms as part of a treatment regimen.

Exemplary P-450 inhibitors include ketoconazole, clarithromycin, erythromycin, isoniazid, fluoxetine, midazolam, delavirdine, indinavir, ritonavir, dihydralazine, verapamil, troleandomycin, tamoxifen and irinotecan. Other P-450 inhibitors are disclosed in Pea et al, *Clin Pharmacokinet* 2001, 40(11), 833-868; Zhou et al, *Current Drug Metabolism* 2004, 5, 415-442; and Wienkers, *J. Pharm Toxicol Methods* 2001, 45: 79-84. A preferred P-450 inhibitor is ritonavir.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of the invention (of formulas (I), (I'), (II), (II'), (III), (III'), (IV) or (IV')), is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a compound of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of a compound of the invention and each cachet or capsule preferably contains from about 0.1 mg to about 500 mg of a compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

The terms "administration of" or "administering a" compound should be understood to mean providing a compound of the invention to a patient in need of treatment in a form that can be introduced into the patient's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of p-secretase enzyme activity may be demonstrated by methodology known in the art. Enzyme inhibition may be determined as follows.

ECL Assay: A homogeneous end point electrochemiluminescence (ECL) assay is performed using a biotinylated BACE substrate. The Km of the substrate is greater than 100 µM and can not be determined due to the limit of solubility of the substrate. A typical reaction contains approximately 0.1 nM enzyme, 0.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction proceeds for 30 min and is then stopped by the addition of 25 µL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 µM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

In particular, the compounds of the invention have activity in inhibiting the beta-secretase enzyme in the aforementioned assay, generally with an $IC_{50}$ from about 1 nM (0.001 µM) to 200 µM. Preferred compounds have an $IC_{50}$ from about 0.001 µM to 1 µM. Such results are indicative of the intrinsic activity of the compounds as inhibitors of beta-secretase enzyme activity.

sAPPβ Assay: sAPPβ is the soluble N-terminal product of APP after processing by BACE 1. Biochemical assays for BACE-1 inhibitions have been developed for evaluating the BACE inhibition properties of drug candidates. Suitable BACE1 assays use purified, soluble recombinant BACE 1 with a coumarin labeled peptide containing an optimized cleavage sequence NFEV at the P2-P2' position. An exemplary cell-based assay is described at Pietrak et al, *Analytical Biochemistry* 342 (2005), 144-151.

Preferred compounds of the invention have an IC50 value in a standard sAPPβ assay of less than 10 µM, more preferably less than 1 µM.

Additional assays used to evaluate the compounds of the invention for use as pharmaceuticals include Pgp transport assays and PXR assays.

Pgp Transport Assay: The compounds of the invention also demonstrate favorable properties in a P-glycoprotein (Pgp) efflux human assay. Pgp is a xenobiotic transport protein, which is expressed in various human tissues, including the intestine, liver and kidney. Pgp acts to transport xenobiotic materials out of cells. Many therapeutically effective compounds have been found to be Pgp substrates. As a result, the interaction of a drug candidate with Pgp is an important concern in pharmaceutical research.

Various Pgp human assays have been developed and commercialized for use in evaluating drug candidates. Typically, the Pgp human assay is designed to determine in vitro inhibitory properties of compounds for human PGP-mediated transport. An exemplary Pgp human assay is described in Keogh et al, *Eur J Pharm Sci* 27 (2006) 543-554.

PXR Assay: The pregnane X receptor (PXR) assay was designed to identify compounds which induce cyclochrome P-450 3A4 (CYP3A4). CYP3A4 is a drug metabolizing enzyme which is present in large amounts human liver microsomes. An exemplary PXR assay is described in Luo et al, *Drug Metabol and Disp* (2002) 30(7):795-804. See also Iyer et al, "Functional Evolution of the Pregrnane X Receptor," *Expert Opin Drug Metab Toxicol* (2006) 2(3):381-397.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate I: 1-benzyl-2-methylpiperidin-4-one

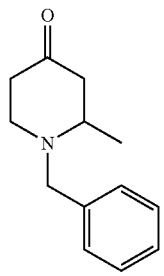

2-Methyl piperidinone hydrochloride (Atlantic Scientific Co. Inc. 0.852 g, 5.08 mmol), powdered sodium carbonate (2.15 g 20.3 mmol) and benzyl chloride (0.585 mL, 5.08 mmol) were dissolved/suspended in $CH_3CN$ (8 mL) under nitrogen and heated at 70° C. overnight. An additional 0.5 mmole benzyl chloride was added, the reaction refluxed for 4 hr, then filtered and evaporated. The residue was chromatographed on silica eluting with a gradient of 0-20% EtOAc/Hex to give the product.

$^1$H NMR (400 MHz, $CDCl_3$) δ 7.4-7.24 (m, 5H), 3.97 (d, J=13.4 Hz, 1H), 3.45 (d, J=13.4 Hz, 1H), 3.0 (m, 2H), 2.54, (m, 2H), 2.37 (t, J=6.1 Hz, 2H), 2.28 (dd, J=7.4, 14.3 Hz, 1H), 1.18 (d, J=6.4 Hz, 3H) ppm.

Alternative Synthesis of Intermediate I: 1-benzyl-2-methylpiperidin-4-one

Intermediate I was also prepared using a method shown in Scheme 2 and similar to that described by M.-J. Blanco-Pilado et al, in WO2004/094380 and to the experimental below for Intermediate II, using benzylamine as the amine.

$^1$H NMR (400 MHz, $CDCl_3$) δ 7.38-7.28 (m, 4H), 7.25 (m, 1H), 3.96 (d, J=13.6 Hz, 1H), 3.45 (d, J=13.4 Hz, 1H), 3.0 (m, 2H), 2.54 (m, 2H), 2.37 (t, J=6.3 Hz, 2H), 2.28 (dd, J=7.5, 14.1 Hz, 1H), 1.18 (d, J=6.6 Hz, 3H) ppm.

Intermediate II: 1-(3-isopropoxybenzyl)-2-methylpiperidin-4-one

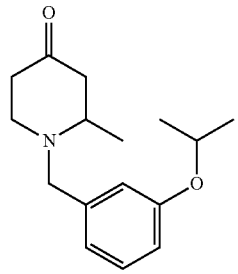

Intermediate II was prepared using a method similar to that described by M.-J. Blanco-Pilado et al in WO2004/094380, using 1-(3-isopropoxyphenyl)methanamine as the amine.

Step 1: 3-isopropoxybenzonitrile

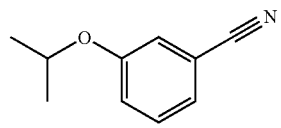

A combination of 32 g (268 mmol, Aldrich) 3-cyanophenol, 26.9 mL (268 mmol) 2-iodopropane, and 88 g (269 mmol) cesium carbonate in 1:1 $CH_2Cl_2$:$CH_3CN$ was heated to reflux and allowed to stir overnight. HPLC/MS showed pure product so the suspension was filtered, washed with $CH_3CN$ and concentrated. The remaining oil was dissolved in $CH_2Cl_2$ and filtered thru a short pad of silica with $CH_2Cl_2$. The filtrate was concentrated to dryness to give the product. An alternative preparation uses the conditions similar to the above except that potassium carbonate is used as the base.

$^1$H NMR (400 MHz, $CDCl_3$) δ 7.35 (m, 1H), 7.21 (m, 1H), 7.12 (m, 2H), 4.58 (m, 1H), 1.35 (d, 6H) ppm.

Step 2: (3-Isopropoxybenzyl)amine

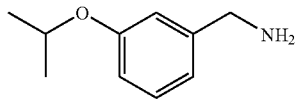

A 500 mL Parr bottle was flushed with argon, then 3-isopropoxybenzonitrile (32 g, 198 mmol) was added and diluted with 150 mL EtOH. The reaction was charged with ~2 mL of an aq. slurry of Raney Nickel, then affixed to a Parr hydrogenation apparatus. The flask was evacuated and flushed with $N_2$ three times before being charged with 40 psi $H_2$. The flask was allowed to shake for 3 hr over which time the flask was recharged to 40 psi and consumption of gas ceased. HPLC/MS showed no starting material so the catalyst was carefully filtered without drying and washed with EtOH. The filtrate was concentrated and purified on an Isco automated system affixed with a Biotage Flash 40(M) cartridge eluted with 0-5% (MeOH+0.5M $NH_3$) in $CH_2Cl_2$ over 30 min at 40 mL/min to give the product.

¹H NMR (400 MHz, CDCl₃) δ 7.24 (m, 1H), 6.85 (m, 2H), 6.76 (m, 1H), 4.56 (m, 1H), 3.83 (s, 2H), 1.4 (bs, ~2H), 1.33 (d, J=6.0 Hz, 6H) ppm.

Step 3:
1-(3-isopropoxybenzyl)-2-methylpiperidin-4-one

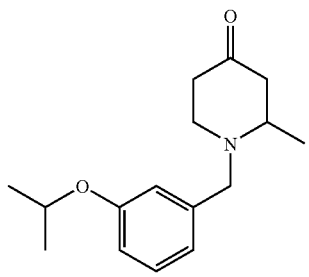

A neat solution of 11 mL (115 mmol) crotonoyl chloride (>95% pure, TCI America) was added dropwise to 8.7 g (120 mmol, Aldrich, anhydrous powder in ampules) AlCl₃ in 200 mL anhydrous CH₂Cl₂ under argon on an ice bath keeping the temperature around 15° C. then allowed to stir 10 min. The flask was cooled to −20° C. on a ethylene glycol/dry ice bath and 18.4 mL (126 mmol) vinyltrimethylsilane (Aldrich) in 10 mL DCM was added dropwise from a jacketed addition funnel cooled with ice water maintaining the temp below −15° C. Stirring continued at −20° C. for 30 min then the reaction was poured into 300 mL of a saturated aq solution of sodium-potassium tartrate containing 150 g K₂CO₃ and ~200 mL ice. The slurry was allowed to stir vigorously for 30 min then filtered thru celite and washed with CH₂Cl₂. The organic layer was separated, dried over Na₂SO₄, filtered and carefully concentrated to give about 14 g of crude (4E)-hexa-1,4-dien-3-one which was immediately taken up in 20 mL CH₃CN and added to 17 g (103 mmol) (3-isopropoxybenzyl)amine (Step 2) in a slurry of 50 mL CH₃CN, 60 mL water, 9.6 g sodium bicarbonate and stirred at rt for 16 hr. The mixture was partitioned between EtOAc and water. The organic layer was separated and dried over Na₂SO₄, filtered and concentrated. The remaining oil was purified on an Isco automated system affixed with Biotage Flash 40(L) cartridge eluted with 0-2.5% (MeOH+0.5M NH₃) in CH₂Cl₂ over 30 min at 50 mL/min to give the product.

¹H NMR (400 MHz, CDCl₃) δ 7.22 (t, J=7.7 Hz, 1H), 6.92 (m, 2H), 6.79 (dd, J=2.4, 8.2 Hz, 1H), 4.55 (septet, J=6 Hz, 1H), 3.92 (d, J=13.6 Hz, 1H), 3.40 (d, J=13.6 Hz, 1H), 3.0 (m, 2H), 2.55 (m, 2H), 2.36 (t, J=6.3 Hz, 2H), 2.27 (dd, J=7.5, 14.1 Hz, 1H), 1.34 (d, J=6.2 Hz, 6H), 1.16 (d, J=6.4 Hz, 3H) ppm.

In an alternative preparation, AlCl₃ (15 g, 0.11 mole) was added to a 3-necked flask equipped with a jacketed addition funnel, flushed with argon and cooled in an ice bath. Crotonyl chloride (21 g, 200 mmol) was added dropwise while keeping the temperature of the reaction below 15° C. The resulting light yellow solution was stirred for 15 min before the ice bath was replaced with an ethyleneglycol/dry ice bath and the solution cooled to −20° C. Vinylsilane (21.1 ml, 220 mmol) was added dropwise from the ice-cooled jacketed addition funnel keeping the temperature of the reaction below −20° C. The reaction was stirred for 3 hr and then added quickly to a slurry of 200 mL saturated aqueous sodium/potassium tartrate solution, 200 g K₂CO₃, 300 mL ice and 500 mL ether. The slurry was stirred vigorously for 30 min then filtered through celite. The organic layer was separated, dried over Na₂SO₄, filtered and carefully concentrated. The oil was dissolved in 200 mL CH₃CN and added dropwise to a cooled (0° C.) suspension of 3-(isopropoxy)benzylamine (30 g, 180 mmol) in a mixture of 2M aq NaHCO₃ (100 mL) and CH₃CN (30 mL). The reaction was stirred at rt overnight and partitioned between water and EtOAc. The organic layer was dried over Na₂SO₄, filtered and concentrated. The resulting oil was chromatographed on silica eluting with 0-50% EtOAc/Hexanes.

¹H NMR (400 MHz, CDCl₃) δ 7.25 (m, 1H), 6.95 (m, 2H), 6.9 (m, 1H), 4.55 (m, 1H), 3.92 (d, 1H), 3.4 (d, 1H), 3.0 (m, 2H), 2.55 (m, 2H), 2.4 (m, 2H), 2.25 (m, 1H), 1.35 (d, 6H), 1.2 (d, 3H) ppm.

Intermediate III: 1-(chloromethyl)-3-{[(1R)-1-methylpropyl]oxy}benzene

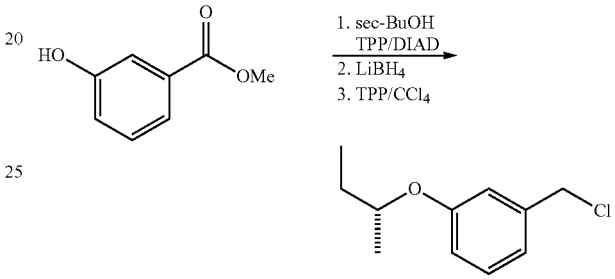

Step 1: methyl
3-{[(1R)-1-methylpropyl]oxy}benzoate

To a 0° C. solution of methyl 3-hydroxybenzoate (5.00 g, 32.9 mmol) in toluene (32.9 ml) was added (S)-(+)-sec-butanol (3.34 ml, 36.1 mmol), triphenylphosphine (9.48 g, 36.1 mmol), and DIAD (7.03 ml, 36.1 mmol). After warming to rt overnight, the reaction mixture was filtered through a fritted funnel and washed with toluene. The filtrate was concentrated. The residue was purified on a silica gel cartridge (0% EtOAc/hexanes to 10% EtOAc/hexanes) to give the desired product.

Step 2: (3-{[(1R)-1-methylpropyl]oxy}phenyl)methanol

To a solution of methyl 3-{[(1R)-1-methylpropyl]oxy}benzoate (3.50 g, 16.8 mmol) in THF (67 mL) was added 2M lithium borohydride solution in THF (25.2 ml, 50.4 mmol). The reaction was heated to 50° C. overnight. The reaction was quenched with MeOH and the solvents were concentrated. The residue was dissolved in EtOAc and washed with saturated NaHCO₃. The aqueous phase was extracted with dichloromethane and the organics were combined, washed with H₂O (2 times) dried with MgSO₄, filtered, and concentrated. The residue was purified on a silica gel cartridge (10% EtOAc/hexanes to 20% EtOAc/hexanes) to give the desired product.

Step 3: 1-(chloromethyl)-3-{[(1R)-1-methylpropyl]oxy}benzene

To a solution of (3-{[(1R)-1-methylpropyl]oxy}phenyl)methanol (1.01 g, 5.60 mmol) in carbon tetrachloride (18.7 ml) was added triphenylphosphine (1.40 g, 5.32 mmol). The reaction was heated to reflux overnight. The reaction was filtered through a fritted funnel and washed with carbon tetrachloride. The filtrate was concentrated. The residue was purified on a silica gel cartridge (0% EtOAc/hexanes to 10% EtOAc/hexanes) to give the desired product.

1H NMR (CDCl$_3$): δ7.26-7.22 (m, 1H); 6.92-6.91 (m, 2H); 6.85-6.82 (m, 1H); 4.55 (s, 2H); 4.33-4.29 (m, 1H); 1.69-1.58 (m, 2H); 1.29 (d, J=6.05 Hz, 3H); 0.979 (t, J=7.42 Hz, 3H).

Intermediate IV: 2-(chloromethyl)-1-fluoro-4-{[(1R)-1-methylpropyl]oxy}-benzene

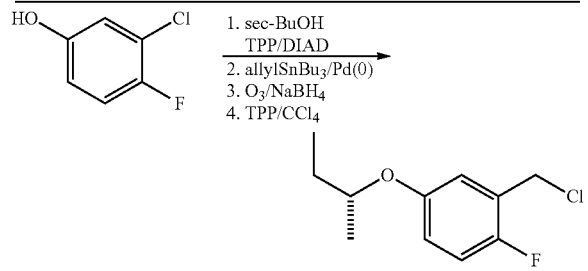

Step 1: 2-chloro-1-fluoro-4-{[(1R)-1-methylpropyl]oxy}benzene

To a 0° C. solution of 3-chloro-4-fluorophenol (2.10 g, 14.3 mmol) in toluene (14.3 ml) was added (S)-(+)-sec-butanol (1.39 ml, 15.0 mmol), triphenylphosphine (3.76 g, 14.3 mmol), and DIAD (3.06 ml, 15.76 mmol). The reaction warmed to rt overnight. The reaction mixture was filtered through a fritted funnel and washed with toluene. The filtrate was concentrated. The residue was diluted with EtOAc and washed with 1N NaOH. The aqueous phase was extracted with EtOAc (2 times). The combined organics were dried with MgSO$_4$, filtered, and concentrated. The residue was purified on a silica gel cartridge (0% EtOAc/hexanes to 4% EtOAc/hexanes) to give the desired product.

Step 2: 1-fluoro-4-{[(1R)-1-methylpropyl]oxy}-2-vinylbenzene

To a solution of 2-chloro-1-fluoro-4-{[(1R)-1-methylpropyl]oxy}benzene (1.75 g, 8.64 mmol) in dioxane (28.8 ml) under argon were added bis(tri-t-butylphosphine) palladium (0) (0.221 g, 0.432 mmol) and cesium fluoride (2.89 g, 19.0 mmol). Argon was bubbled through the reaction for 2 min. To the reaction was added tributyl (vinyl) tin (3.03 ml, 10.4 mmol) and the argon bubbled for another 5 min. The reaction was sealed and heated to 100° C. overnight. The reaction was partitioned between H$_2$O and EtOAc. The aqueous phase was extracted with EtOAc (3 times). The combined organics were dried with MgSO$_4$, filtered, and concentrated. The residue was purified by column chromatography on a silica gel cartridge (0% EtOAc/hexanes to 4% EtOAc/hexanes) to give the desired product.

Step 3: (2-fluoro-5-{[(1R)-1-methylpropyl]oxy}phenyl)methanol

Ozone was bubbled through a −78° C. solution of 1-fluoro-4-{[(1R)-1-methylpropyl]oxy}-2-vinylbenzene (0.81 g, 4.17 mmol) in dichloromethane (27.8 ml) and MeOH (13.90 ml) until the reaction color remained blue. The reaction stirred 10 min, and then was purged with N$_2$ for 10 min. MeOH (25 mL) was added, followed by sodium borohydride (0.237 g, 6.25 mmol). The reaction warmed to rt. After 1 h, the reaction mixture was concentrated in vacuo. The residue was purified by column chromatography on a silica gel cartridge (12% EtOAc/hexanes) to give the desired product.

Step 4: 2-(chloromethyl)-1-fluoro-4-{[(1R)-1-methylpropyl]oxy}benzene

To a solution of (2-fluoro-5-{[(1R)-1-methylpropyl]oxy}phenyl)methanol (0.091 g, 0.459 mmol) in carbon tetrachloride (4.59 ml) was added triphenylphosphine resin (0.241 g, 0.918 mmol). The reaction was heated to 78° C. overnight in a pressure tube with minimal stirring. The reaction mixture was filtered through a fritted funnel and washed with carbon tetrachloride. The filtrate was concentrated to give the desired product.

$^1$H NMR (CDCl$_3$): δ 6.96 (t, J=9.16 Hz, 1H); 6.93-6.90 (m, 1H); 6.82-6.78 (m, 1H); 4.59 (s, 2H); 4.26-4.18 (m, 1H); 1.78-1.57 (m, 2H); 1.27 (d, J=6.04 Hz, 3H); 0.975 (t, J=7.33 Hz, 3H).

Intermediate V: 1-(chloromethyl)-3-(cyclopropylmethyl)benzene

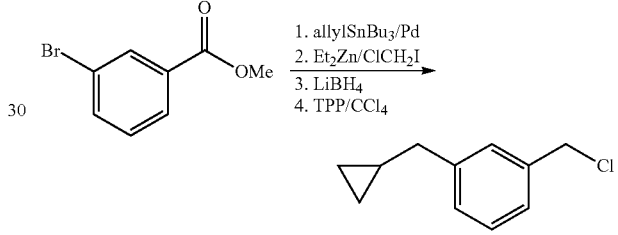

Step 1: methyl 3-allylbenzoate

To a solution of methyl 3-bromobenzoate (10.0 g, 46.5 mmol) in DMF (50 mL) was added ally tributyltin (23.1 g, 69.8 mmol) followed by tetrakis(triphenylphoshine) palladium(0) (1.08 g, 0.93 mmol). After stirring 80° C. overnight the reaction mixture was poured into H$_2$O (500 mL), extracted with ethyl acetate (three times), dried over MgSO$_4$ and concentrated under vacuum to afford the desired product.

LRMS (M+1)=177.0

Step 2: methyl 3-(cyclopropylmethyl)benzoate

To a solution of methyl 3-allylbenzoate (8.39 g, 47.6 mmol) in dichloroethane (100 mL) was added iodochloromethane (26.9 mL, 152 mmol). The solution was cooled to 0° C. and diethyl zinc (1.0 M in heptanes, 76.2 mL, 76.2 mmol) was added. The cooling bath was removed and the reaction was stirred at rt for 30 min. The reaction mixture was quenched with 1N HCl, extracted with methylene chloride (three times), dried with MgSO$_4$ and concentrate under vacuum to afford the desired product.

LRMS (M+1)=191.1

Step 3: [3-(cyclopropylmethyl)phenyl]methanol

To a solution of methyl 3-(cyclopropylmethyl)benzoate (9.06 g, 47.6 mmol) in THF (100 mL) was added lithium borohydride (2.0 M in THF, 71.4 mL, 142.9 mmol). After stirring at 50° C. for 1 h the reaction was cooled, quenched with excess methanol and concentrated under vacuum. Purification by silica gel chromatography (30% EtOAc/hexanes) afforded the desired product.

Step 4:
1-(chloromethyl)-3-(cyclopropylmethyl)benzene

To a solution of [3-(cyclopropylmethyl)phenyl]methanol (1.67 g, 10.3 mmol) in carbon tetrachloride (100 mL) was added polystyrene bound triphenyl phosphine (2.15 mmol/g, 9.57 g, 20.6 mmol). After stirring at 100° C. overnight the resin was filtered of and the solvent was removed under vacuum to afford the desired product.

$^1$H NMR (CDCl$_3$): δ 7.31-7.21 (m, 4H), 4.58 (s, 2H), 2.55 (d, J=7.0 Hz, 2H), 0.98 (m, 1H), 0.55 (m, 2H), 0.20 (m, 2H).

Intermediate VI: 1-bromo-3-methylpent-2-ene

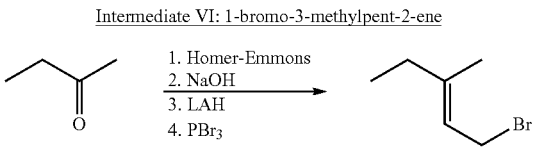

Step 1: methyl-3-methylpent-2-enoate

To a 0° C. mixture of methyl diethylphosphonoacetate (12.7 ml, 69.3 mmol) and sodium methoxide (13.0 ml, 69.3 mmol) was added dropwise 2-butanone (5.81 ml, 69.3 mmol) over 30 min. After the addition, the mixture warmed to rt and stirred overnight. To the reaction was added 20 mL of H$_2$O. The mixture was extracted with EtOAc (3 times). The combined organics were dried with MgSO$_4$, filtered, and concentrated. The crude oil was distilled at 110° C. at 35 mmHg to give the desired product.

Step 2: 3-methylpent-2-enoic acid

To a solution of methyl-3-methylpent-2-enoate (3.27 g, 25.5 mmol) in MeOH (8.50 ml) was added 1N sodium hydroxide solution (30.6 ml, 30.6 mmol). The reaction was heated to 70° C. for 4 h. The reaction was washed with EtOAc. The aqueous phase was acidified with 1N HCl and extracted with EtOAc (3 times). The combined organics were dried with MgSO$_4$, filtered, and concentrated to give the desired product.

Step 3: 3-methylpent-2-en-1-ol

Methanol (0.71 ml, 17.5 mmol) in ether (5.48 ml) was added to 2M lithium aluminum hydride solution (17.5 ml, 17.5 mmol) at 0° C. To the reaction was added dropwise 3-methylpent-2-enoic acid (2.00 g, 17.5 mmol) in ether (5.48 ml). The solution warmed to rt overnight. The reaction was slowly quenched with 0.316 mL H$_2$O, 0.316 mL 1N NaOH and 0.950 mL of water. The mixture was filtered, and the layers were separated. The aqueous phase was extracted with EtOAc (2 times). The combined organics were dried with MgSO$_4$, filtered, and concentrated to give the desired product.

Step 4: 1-bromo-3-methylpent-2-ene

To a −15° C. solution of phosphorous tribromide (0.235 ml, 2.50 mmol) and pyridine (0.162 ml, 2.00 mmol) in hexanes (4.99 ml) was added 3-methylpent-2-en-1-ol (0.500 g, 4.99 mmol) in ether (4.99 ml) via cannula. The reaction warmed to 0° C. for 2 h. The bath was removed and the reaction stirred at rt for 1 h. The reaction was diluted with H$_2$O and hexanes. The layers were separated and the organics were washed with 0.5 M KHSO$_4$, brine, dried with MgSO$_4$, filtered, and concentrated to give the desired product.

$^1$H NMR (CDCl$_3$): δ 5.55-5.48 (m, 1H); 4.03 (d, J=8.24 Hz, 2H); 2.18-2.05 (m, 2H); 1.73 (s, 3H); 1.01 (t, J=7.50 Hz, 3H).

Intermediate VII: 1-(chloromethyl)-3-(1-cyclopropylethyl)benzene

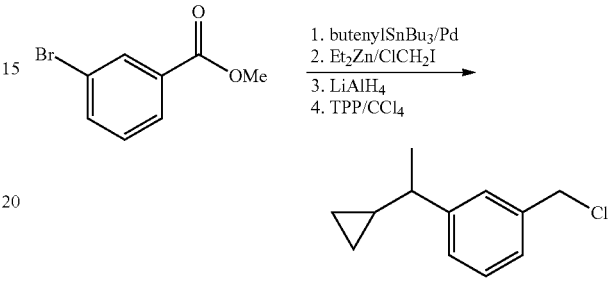

Step 1: methyl 3-(1-methylprop-2-en-1-yl)benzoate

To a solution of methyl 3-bromobenzoate (1.81 g, 8.42 mmol) in DMF (50 mL) was added (E)-4-(tributylstannyl)but-2-ene (Weigand, S.; Bruckner, R. *Synthesis*, 1995, 475) (3.48 g, 10.1 mmol) followed by tetrakis(triphenylphoshine)palladium(0) (0.49 g, 0.42 mmol). After stirring 80° C. overnight the reaction mixture was poured into H$_2$O (500 mL), extracted with ethyl acetate (three times), dried over MgSO$_4$ and concentrated under vacuum to afford the desired product. Purification by silica gel chromatography (5% EtOAc/hexanes) afforded the desired product.

LRMS (M+1)=191.1

Step 2: methyl 3-(1-cyclopropylethyl)benzoate

To a solution of methyl 3-(1-methylprop-2-en-1-yl)benzoate (0.85 g, 4.49 mmol) in dichloroethane (20 mL) was added iodochloromethane (2.54 mL, 14.4 mmol). The solution was cooled to 0° C. and diethyl zinc (1.0 M in heptanes, 7.13 mL, 7.13 mmol) was added. The cooling bath was removed and the reaction was stirred at rt for 30 min. The reaction mixture was quenched with 1N HCl, extracted with methylene chloride (three times), dried with MgSO$_4$ and concentrate under vacuum to afford the desired product.

LRMS (M+1)=205.1

Step 3: [3-(1-cyclopropylethyl)phenyl]methanol

To a solution of methyl 3-(1-cyclopropylethyl)benzoate (0.917 g, 4.48 mmol) in THF (50 mL) was added lithium aluminum hydride (1.0 M in THF, 13.5 mL, 13.5 mmol). After stirring at rt for 15 min the reaction was cooled and quenched with water, extracted into ethyl acetate (three times) and concentrated under vacuum. Purification by silica gel chromatography (30% EtOAc/hexanes) afforded the desired product.

Step 4:
1-(chloromethyl)-3-(1-cyclopropylethyl)benzene

To a solution of [3-(1-cyclopropylethyl)phenyl]methanol (0.128 g, 0.73 mmol) in carbon tetrachloride (20 mL) was added polystyrene bound triphenyl phosphine (2.15 mmol/g, 0.68 g, 1.5 mmol). After stirring at 100° C. overnight the resin was filtered of and the solvent was removed under vacuum to afford the desired product.

$^1$H NMR (CDCl$_3$) δ 7.32-7.16 (m, 4H), 4.60 (s, 2H), 2.00 (m, 1H), 1.34 (d, J=7.1 Hz, 3H, 0.94 (m, 1H), 0.56 (m, 1H), 0.44 (m, 1H), 0.19 (m, 2H).

Intermediate VIII: 1-(bromomethyl)cyclohexane

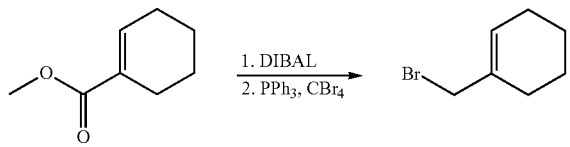

Step 1: cyclohex-1-en-1-ylmethanol

To a 0° C. solution of methyl-1-cyclohexene-1-carboxylate (1.46 mL, 10.7 mmol) in THF (10 mL) was added 20 wt % DIBAL in toluene (18.2 mL, 32.1 mmol). After stirring at 0° C. for 2 h, 1N HCl was added to quench the solution. The resulting mixture was extracted with ether (three times), washed with H$_2$O and brine, dried with Na$_2$SO$_4$ and concentrated. The crude compound was chromatographed to give the desired product.

Step 2: 1-(bromomethyl)cyclohexene

To a 0° C. solution of cyclohex-1-en-1-ylmethanol (0.20 g, 2.04 mmol) and triphenylphosphine (0.59 g, 2.24 mmol) was added carbon tetrabromide (0.74 g, 2.24 mmol). After stirring at rt for 72 h, the reaction mixture was concentrated and chromatographed to give the desired product.

Intermediate IX: 1-(bromomethyl)cyclopentene

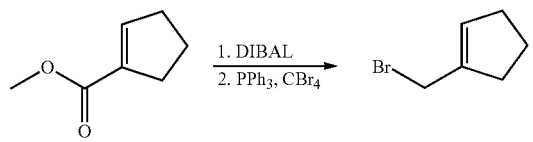

1-(bromomethyl)cyclopentene was prepared using the same procedures as Intermediate VIII but starting from methyl 1-cyclopentencarboxylate.

Intermediate X: 1-isopropyl-1H-indole-6-carbaldehyde

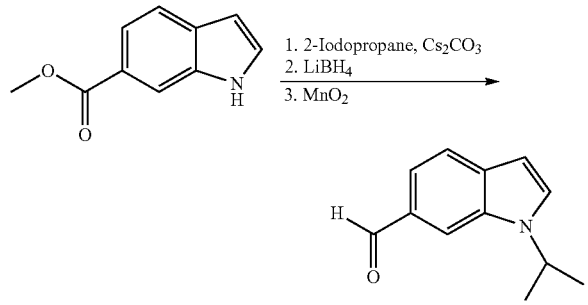

Step 1: methyl 1-isopropyl-1H-indole-6-carboxylate

To a solution of methyl 1H-indole-6-carboxylate (5.00 g, 28.5 mmol) and cesium carbonate (18.6 g, 57.1 mmol) in DMPU (50 mL) was added 2-iodopropane (3.71 mL, 37.1 mmol). After stirring at 80° C. for 4 h, the solution was cooled to rt, poured onto ether, washed with H$_2$O (three times) and brine, dried with Na$_2$SO$_4$, and concentrated. The crude compound was chromatographed to give the desired product. LCMS (M+1)=218.1

Step 2: (1-isopropyl-1H-indol-6-yl)methanol

To a 0° C. solution of methyl 1-isopropyl-1H-indole-6-carboxylate (0.50 g, 2.30 mmol) in THF (5 mL) was added 1M lithium borohydride in THF (6.90 mL, 6.90 mmol). After stirring at rt for 96 h, quenched with MeOH and let stir for 1 h. The reaction mixture was concentrated, partitioned between saturated sodium bicarbonate and EtOAc, washed with H$_2$O and brine, dried with Na$_2$SO$_4$, and concentrated. The crude compound was chromatographed to give the desired product.

LCMS (M+1)=190.2

Step 3: 1-isopropyl-1H-indole-6-carbaldehyde

To a solution of (1-isopropyl-1H-indol-6-yl)methanol (0.18 g, 0.97 mmol) in CCl$_4$ (5 mL) was added manganese dioxide (0.13 g, 1.45 mmol). After stirring at 60° C. for 1 h, then 77° C. for 2 h, filtered reaction mixture through celite and concentrated. Partitioned crude compound between saturated sodium bicarbonate and EtOAc, washed with H$_2$O and brine, dried with Na$_2$SO$_4$, and concentrated. The crude compound was chromatographed to give the desired product.

LCMS (M+1)=188.1

Intermediate XI: 1-(bromomethyl)-2-methylcyclopentene

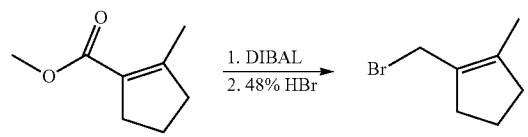

Step 1: (2-methylcyclopent-1-en-1-yl)methanol

To a 0° C. solution (0.24 g, 1.73 mmol) methyl 2-methylcyclopent-1-ene-1-carboxylate (*Can. J. Chem.*, 1979, 57, 1431) in THF (5 mL) was added 1M DIBAL in THF (5.18 mL, 5.18 mmol). After stirring at 0° C. for 2 h, 1N HCl was added to quench the solution. The resulting mixture was extracted with ether (three times), washed with H$_2$O and brine, dried with Na$_2$SO$_4$, and concentrated. The crude compound was chromatographed to give the desired product.

Step 2: 1-(bromomethyl)-2-methylcyclopentene

To a 0° C. solution of (2-methylcyclopent-1-en-1-yl)methanol (0.07 g, 0.62 mmol) in pentane (1.5 mL) was added 48% HBr (0.14 mL, 1.24 mmol). After stirring at 0° C. for 30 min, the solution was washed with brine, saturated sodium bicarbonate, and brine again. The organic layer was concentrated to give the desired product, which was used without further purification.

Intermediate XII: 3: 1-(chloromethyl)-3-(1-cyclopropylethoxy)benzene

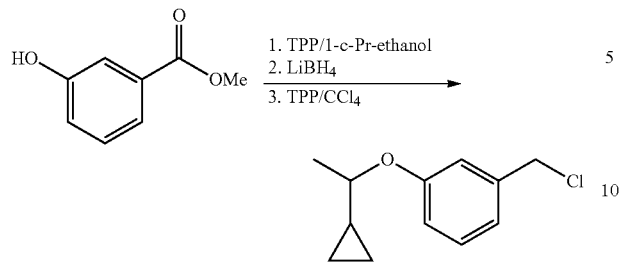

Step 1: methyl 3-(1-cyclopropylethoxy)benzoate

Methyl 3-hydroxybenzoate (10.0 g, 65.7 mmol) in toluene (65.7 ml) was cooled to 0° C. and added 1-cyclopropylethanol (6.43 ml, 65.7 mmol), triphenylphosphine (18.9 g, 72.3 mmol), and DIAD (14.1 ml, 72.3 mmol). The reaction warmed to rt for sixteen hours. The reaction mixture was filtered through a fritted funnel to remove precipitated triphenylphosphine oxide and washed with toluene. The filtrate was concentrated. The residue was purified by column chromatography on silica gel Biotage 65i, eluting with 10% ethyl acetate/hexanes to give a colorless oil.

Step 2: [3-(1-cyclopropylethoxy)phenyl]methanol

Methyl 3-(1-cyclopropylethoxy)benzoate (11.7 g, 53.1 mmol) in tetrahydrofuran (212 mL) was added lithium borohydride (80.0 ml, 159 mmol). The reaction was heated at 50° C. for twelve hours. The reaction was quenched with methanol. The solvents were concentrated. The residue was dissolved in ethyl acetate and washed with saturated NaHCO$_3$. The aqueous layer was extracted three times with dichloromethane and the organics were combined, washed twice with water, dried with MgSO$_4$, filtered, and concentrated. The enantiomers were resolved on the chiral OD column (10 cm) with a flow rate of 300 ml/mn wavelength 275 nm running 97/3 hexanes/ethanol as the solvent system.

Step 3: 1-(chloromethyl)-3-(1-cyclopropylethoxy)benzene

[3-(1-cyclopropylethoxy)phenyl]methanol (0.418 g, 2.17 mmol) in carbon tetrachloride (8.70 ml) was added triphenylphosphine resin (1.14 g, 4.35 mmol). The reaction was refluxed overnight with minimal stirring at 78° C. The next day the mixture was filtered through a fritted funnel and washed with dichloromethane. The filtrate was concentrated and no purification was necessary.

$^1$H NMR (CDCl$_3$): δ7.23-7.21 (m, 1H), 6.94-6.92 (m, 2H), 6.85-6.83 (m, 1H), 4.54 (s, 2H), 3.86-3.82 (m, 1H), 1.36 (d, J=6.1 Hz, 3H), 1.16-1.09 (m, 1H), 0.58-0.52 (m, 2H), 0.41-0.36 (m, 1H), 0.30-0.24 (m, 1H).

Intermediate XIII: 1-(chloromethyl)-3-(cyclopropyloxy)benzene

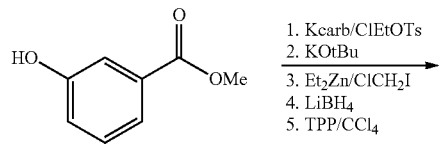

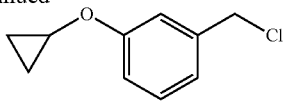

Step 1: methyl 3-(2-chloroethoxy)benzoate

To a solution of methyl 3-hydroxybenzoate (10.0 g, 65.7 mmol) in DMF (100 mL) was added potassium carbonate (18.17 g, 131.4 mmol) and 2-chloroethyl-p-toluenesulfonate (15.7 g, 67.0 mmol). After stirring at 60° C. overnight the reaction mixture was poured into H$_2$O, extracted with ethyl acetate (three times), dried over MgSO$_4$ and concentrated under vacuum. Purification by silica gel chromatography (10% EtOAc/hexanes) afforded the desired product.
LRMS (M+1)=215.0

Step 2: methyl 3-(vinyloxy)benzoate

To a 0° C. solution of methyl 3-(2-chloroethoxy)benzoate (5.61 g, 26.1 mmol) in THF (50 mL) was added potassium tert-butoxide (3.67 g, 32.7 mmol). When the addition was complete the reaction was allowed to warm to rt. After stirring at rt overnight the reaction was quenched with water. The solution was extracted with diethyl ether (three times), dried over MgSO$_4$, and concentrated under vacuum. Purification by silica gel chromatography afforded the desired product.
LRMS (M+1)=179.1

Step 3: methyl 3-(cyclopropyloxy)benzoate

To a solution of methyl 3-(vinyloxy)benzoate (0.83 g, 3.99 mmol) in dichloroethane (20 mL) was added iodochloromethane (1.09 mL, 14.9 mmol). The solution was cooled to 0° C. and diethyl zinc (1.0 M in hexanes, 7.48 mL, 7.48 mmol) was added. The cooling bath was removed and the reaction was stirred at rt for 30 min. The reaction mixture was quenched with 1N HCl, extracted with methylene chloride (three times), dried with MgSO$_4$ and concentrate under vacuum to afford the desired product.
LRMS (M+1)=193.1

Step 4: 3-(cyclopropyloxy)phenyl]methanol

To a solution of methyl 3-(cyclopropyloxy)benzoate (2.83 g, 14.7 mmol) in THF (50 mL) was added lithium borohydride (2.0 M in THF, 22.1 mL, 44.2 mmol). The reaction mixture was heated to 50° C. for min after which methanol (0.60 mL, 14.73 mL) was added and stirred for 15 min. The reaction was cooled and quenched with excess methanol and concentrated under vacuum. Purification by silica gel chromatography (30% EtOAc/hexanes) afforded the desired product.

Step 5: 1-(chloromethyl)-3-(cyclopropyloxy)benzene

To a solution of 3-(cyclopropyloxy)phenyl]methanol (1.77 g, 10.8 mmol) in carbon tetrachloride (30 mL) was added triphenylphosphine (2.54 g, 9.70 mmol). After heating to 100° C. for 12 hr the solution was concentrated under vacuum. Purification by silica gel chromatography (5% EtOAc/hexanes) afforded desired product.
$^1$H NMR (CDCl$_3$): δ 7.26 (m, 1H), 7.07 (m, 1H), 7.01-6.97 (m, 2H), 4.56 (s, 2H), 3.73 (m, 1H), 0.80-0.77 (m, 4H).

Intermediate XIV: 2,2-dimethyl-1,2,3,4-tetrahydroquinoline-8-carboxylic acid

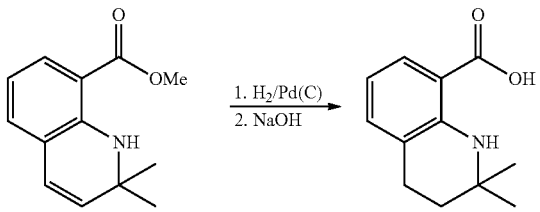

Step 1: methyl 2,2-dimethyl-1,2,3,4-tetrahydro-quinoline-8-carboxylate

A solution of methyl 2,2-dimethyl-1,2-dihydroquinoline-8-carboxylate (Example 47, step 3) (1.00 g, 4.63 mmol) in methanol (20 mL) containing a catalytic amount of 10% palladium on carbon was placed under an atmosphere of hydrogen at ambient pressure and temperature. After stirring at room temperature for 2 h the reaction mixture was filtered through a pad of celite and concentrated under vacuum. Purification by silica gel chromatography (2.5% EtOAc/hexanes) afforded the desired compound.

Step 2: 2,2-dimethyl-1,2,3,4-tetrahydroquinoline-8-carboxylic acid

To a solution of methyl 2,2-dimethyl-1,2,3,4-tetrahydroquinoline-8-carboxylate (0.138 g, 0.629 mmol) in THF (5 mL) and $H_2O$ (5 mL) was added a 1N aqueous solution of sodium hydroxide (1.88 mL, 1.88 mmol). After stirring at 50° C. overnight the reaction mixture was acidified to pH 2 using 1N aqueous HCl, extracted with ethyl acetate (three times), dried over $MgSO_4$ and concentrated under vacuum to afford the desired compound that was used without further purification.
LRMS (M+1)=206.0

Intermediate XV: (5R,7S)-(5S,7R)-8-benzyl-1-(3-fluorophenyl)-7-methyl-4-thioxo-1,3,8-triazaspiro[4.5]decan-2-one

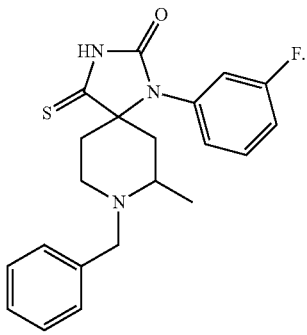

Step 1: 8-benzyl-1-(3-fluorophenyl)-7-methyl-4-thioxo-1,3,8-triazaspiro[4.5]decan-2-one The thiohydantoin was prepared from 1-benzyl-2-methylpiperidin-4-one (Intermediate I) using a procedure similar to that described for (5R,7S)-(5S,7R)-1-(3-fluorophenyl)-8-(3-isopropoxybenzyl)-7-methyl-4-thioxo-1,3,8-triazaspiro[4.5]decan-2-one (Intermediate XXXIII)

Intermediate XVI: cis 2-(3-methoxyphenyl)cyclopentanamine

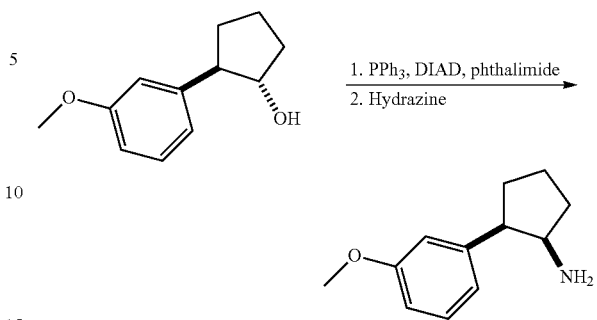

Step 1: cis 2-(3-methoxyphenyl)cyclopentyl]-1H-isoindole-1,3(2H)-dione

To a 0° C. solution of trans-2-(3-methoxyphenyl)cyclopentanol (Platte Valley Scientific, 0.35 g, 1.82 mmol), triphenylphosphine (0.62 g, 2.37 mmol), and phthalimide (0.27 g, 1.82 mmol) in $CH_2Cl_2$ (10 mL) was added DIAD (0.47 mL, 2.37 mmol). After stirring at room temperature overnight, the solution was poured onto saturated sodium bicarbonate, extracted with EtOAc (three times), washed with $H_2O$ and brine, dried with $Na_2SO_4$, and concentrated. The crude compound was chromatographed to give the desired product.
LCMS (M+1)=321.9

Step 2: cis 2-(3-methoxyphenyl)cyclopentanamine

To a solution of cis 2-[2-(3-methoxyphenyl)cyclopentyl]-1H-isoindole-1,3(2H)-dione (0.23 g, 0.72 mmol) in toluene (3 mL) was added hydrazine (0.23 mL, 7.23 mmol). After stirring at room temperature for 1 h, then 95° C. for 4 h, a precipitate formed. The mixture was cooled to rt, filtered, and washed with toluene. The filtrate was concentrated to give the desired product, which was used without further purification.
LCMS (M+1)=192.0

Intermediate XVII: 1-(chloromethyl)-3-{cis-2-methylcyclopropyl]oxy}-benzene

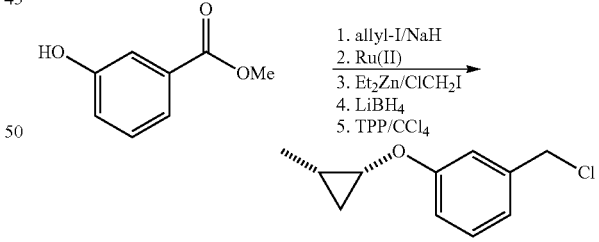

Step 1: methyl 3-(allyloxy)benzoate

To a solution of methyl 3-hydroxybenzoate (5.0 g, 32.9 mmol) in DMF (20 mL) was added allyl iodide (6.62 g, 39.4 mmol) followed by sodium hydride (60% oil dispersion, 0.95 g, 39.4 mmol). After stirring at rt for 5 h, the reaction mixture was quenched with $H_2O$, extracted with ethyl acetate (three times), dried over $MgSO_4$ and concentrated under vacuum. Purification by silica gel chromatography (10% EtOAc/hexanes) afforded the desired product.
LRMS (M+1)=193.1

Step 2: methyl 3-[(1E)-prop-1-en-1-yloxy]benzoate and methyl 3-[(1Z)-prop-1-en-1-yloxy]benzoate To a solution of methyl 3-(allyloxy)benzoate (2.20 g, 11.4 mmol) in THF (20 mL) was added chlorohydridotris(triphenylphosphine) ruthenium (II) toluene adduct (0.23 g, 0.23 mmol). After stirring at 80° C. for 24 h the reaction mixture was concentrated under vacuum. Purification by silica gel chromatography (10% EtOAc/hexanes) afforded a mixture of E and Z olefin isomers that were separated on a ChiralPak AD column.

LRMS (M+1)=193.1

Step 3: methyl 3-{cis-2-methylcyclopropyl]oxy}benzoate

To a solution of methyl 3-[(1E)-prop-1-en-1-yloxy]benzoate (1.0 g, 5.2 mmol) in dichloroethane (10 mL) was added iodochloromethane (2.93 mL, 16.6 mmol). The solution was cooled to 0° C. and diethyl zinc (1.0 M in heptanes, 5.20 mL, 5.20 mmol) was added. The cooling bath was removed and the reaction was stirred at rt for 30 min. The reaction mixture was quenched with 1N HCl, extracted with methylene chloride (three times), dried with $MgSO_4$ and concentrate under vacuum to afford the desired product.

LRMS (M+1)=207.3

Step 4: (3-{cis-2-methylcyclopropyl]oxy}phenyl)methanol

To a solution of methyl 3-{cis-2-methylcyclopropyl]oxy}benzoate (0.925 g, 4.49 mmol) in THF (10 mL) was added lithium borohydride (2.0 M in THF, 6.72 mL, 13.5 mmol). After stirring at 50° C. overnight the reaction was cooled and quenched with excess methanol and concentrated under vacuum. Purification by silica gel chromatography (30% EtOAc/hexanes) afforded the desired product.

Step 5: 1-(chloromethyl)-3-{cis-2-methylcyclopropyl]oxy}benzene

To a solution of (3-{cis-2-methylcyclopropyl]oxy}phenyl)methanol (0.275 g, 1.54 mmol) in carbon tetrachloride (40 mL) was added polystyrene bound triphenyl phosphine (2.15 mmol/g, 1.44 g, 3.08 mmol). After stirring at 100° C. overnight the resin was filtered of and the solvent was removed under vacuum to afford the desired product.

$^1$H NMR (CDCl$_3$) δ 7.27 (m, 1H), 7.04 (d, J=1.6 Hz, 1H), 6.71 (m, 2H), 4.57 (s, 2H), 3.40 (m, 1H), 1.15 (d, J=5.5 Hz, 3H), 1.12 (m, 1H), 0.94 (m, 1H), 0.58 (m, 1H).

Intermediate XVIII: spiro[2.5]octan-6-amine

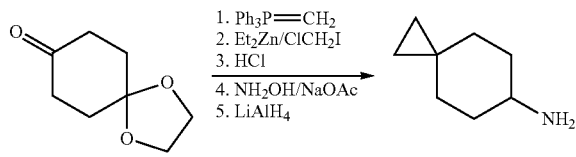

1. Ph$_3$P=CH$_2$
2. Et$_2$Zn/ClCH$_2$I
3. HCl
4. NH$_2$OH/NaOAc
5. LiAlH$_4$

Step 1: 8-methylene-1,4-dioxaspiro[4.5]decane

To a slurry of 8.46 g (23.7 mmol) triphenylphosphonium bromide in 60 mL of ether was added 9.4 mL (23.7 mmol) of n-BuLi at rt. The ylide was allowed to form over 4 h before a solution containing 3.7 g (23.7 mmol) of 1,4 cyclohexanedione ethylene ketal in 5: ether/THF was added. The resulting mixture was refluxed gently overnight, cooled, and filtered. The filtrate was washed with water (two times), brine, and dried over $MgSO_4$. Evaporation of the solvent and column chromatography (9:1 Hexanes/EtOAc) afforded the desired olefin.

$^1$H NMR δ 4.64 (s, 2H), 3.95 (s, 4H), 2.31 (t, J=7 Hz, 2H), 1.71 (t, J=7 Hz, 2H).

Step 2: 7,10-dioxaspiro[2.2.4.2]dodecane

Chloroiodomethane (4.8 mL, 61.6 mmol) was added to a 0° C. mixture containing 2.97 g (19.3 mmol) of the olefin from step 1 in 50 mL of DCE followed by the addition of 30.8 mL (30.8 mmol) of $Et_2Zn$ (1M in hexanes). The reaction was stirred at 0° C. for 1 h before it was quenched with 1N HCl. The mixture was extracted with DCM (three times) and the combined extracts were dried over $MgSO_4$ and concentrated. Column chromatography (9:1 Hexanes/EtOAc) afforded the desired compound as a colorless liquid.

Step 3: spiro[2.5]octan-6-one

A solution containing 3.0 g (17.8 mmol) of the ketal from step 2 in 100 mL of THF was treated with 100 mL (100 mmoL) of 1N HCl. The reaction was allowed to stir for 16 h then extracted with ether (3 times). The combined extracts were washed with brine and dried over $MgSO_4$. Evaporation of the solvent afforded the desired ketone as an oil.

$^1$H NMR (CDCl$_3$) δ 2.4 (t, J=7 Hz, 2H), 1.65 (t, J=7 Hz, 2H), 0.45 (s, 4H).

Step 4: spiro[2.5]octan-6-one oxime

To a solution containing 2.1 g (16.9 mmol) of the ketone from step 3 in 10 mL of ethanol was added 2.0 g (28.7 mmol) of hydroxylamine hydrochloride followed by 4.0 g (29 mmol) of NaOAc in 20 mL of water. The resulting mixture was refluxed for 3 h, cooled and concentrated to one-half volume and the precipitate was collected.

$^1$H NMR (CDCl$_3$) δ 8.38 (bs, 1H), 2.61 (t, J=7 Hz, 2H), 2.3 (t, J=7 Hz, 2H), 1.65 (m, 4H), 0.41 (s, 4H).

Step 5: spiro[2.5]octan-6-amine

A solution containing 1.0 g (7.2 mmol) of the oxime from step 4 in 30 mL of THF was treated with 21 mL (21 mmol) of LAH (1M in ether). The reaction mixture was refluxed for 3 h, cooled and quenched with 4 mL of water and 8 mL of 1N NaOH. The solids were filtered and the filtrate was extracted with ether (three times). The combined extracts were dried and evaporated to give the desired amine.

$^1$H NMR (CDCl$_3$) δ 2.61 (m, 1H), 2.0-1.6 (m, 4H), 1.25 (m, 2H), 0.9 (d, 2H), 0.41-0.18 (s, 4H).

Intermediate XIX: trans 6-phenylspiro[2.4]heptan-5-amine

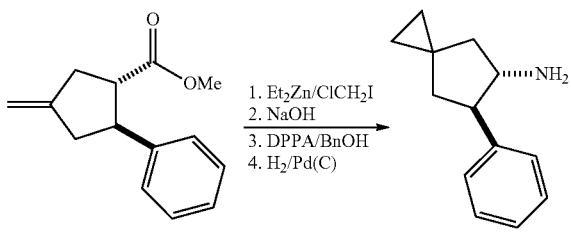

Step 1: methyl trans-6-phenylspiro[2.4]heptane-5-carboxylate

Chloroiodomethane (6.3 g, 35.5 mmol) was added to a 0° C. mixture containing 2.4 g (11.1 mmol) of methyl trans-4-methylene-2-phenylcyclopentanecarboxylate (*J. Am. Chem. Soc.* 1983, 105, 2315) in 25 mL of DCE followed by the addition of 17.8 mL (17.8 mmol) of $Et_2Zn$ (1M in hexanes). The reaction was stirred at 0° C. for 1 h before it was quenched with 1N HCl. The mixture was extracted with DCM (three times) and the combined extracts were dried over $MgSO_4$ and concentrated. Column chromatography (9:1 Hexanes/EtOAc) afforded the desired compound as a colorless liquid.
LRMS (M+H)=231.0

Step 2: trans-6-phenylspiro[2.4]heptane-5-carboxylic acid

To a solution containing 1.0 g (4.3 mmol) of the ester from step 2 dissolved in 25 mL of a 1/1 methanol/THF mixture was added 13 mL (13 mmol) of NaOH. The reaction was stirred for 3 h before it was concentrated and treated with 20 mL of 1N HCl. The precipitate was dissolved in 50 mL of DCM and separated from the aqueous phase. The organic extract was dried over $MgSO_4$ and concentrated to give the desired carboxylic acid.
LRMS=171.02.

Step 3: benzyl[trans-6-phenylspiro[2.4]hept-5-yl]carbamate

To a solution containing 750 mg (3.47 mmol) of the acid from step 3 in 25 mL of benzene was added 0.53 mL (3.8 mmol) of TEA, 413 mg (3.8 mmol) of benzyl alcohol and 0.75 mL (3.5 mmol) of DPPA and the solution was refluxed under nitrogen for 17 h. The reaction mixture was cooled and diluted with 100 mL of EtOAc and washed with saturated $NaHCO_3$ (three times), water (two times) and brine. The organic extracts were dried over $MgSO_4$, concentrated and chromatographed (3:2 Hexanes/EtOAc) to afford the desired carbamate.
LRMS (M+H)=322.01.

Step 4: trans 6-phenylspiro[2.4]heptan-5-amine

A solution containing 1.0 g (3.1 mmol) of the carbamate from step 4 and 131 mg of 10% $Pd(OH)_2$ in 20 mL of methanol was stirred under a balloon of hydrogen for 2 h. The reaction mixture was filtered through Celite and evaporated to leave the desired amine as an oil.
LCMS (M−$NH_3$)=171.0

$^1$H NMR ($CDCl_3$) δ 7.41-7.13 (m, 5H), 3.41 (q, J=7 Hz, 1H), 2.82 (q, J=7 Hz, 1H), 2.21 (bs, 2H), 1.93 (m, 3H), 1.65 (m, 1H), 0.55 (m, 4H).

Intermediate XX: 1,1-dimethylsilolan-3-amine

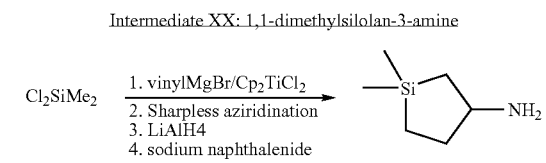

Step 1: 1,1-dimethyl-2,5-dihydro-1H-silole

To a −40° solution of dichlorodimethylsilane (6.0 g, 46.5 mmol) in THF (100 mL) was added bis(cyclopentadienyl) titanium dichloride (0.58 g, 2.3 mmol) followed by vinyl magnesium bromide (11.0M in THF, 98 ml, 98 mmol). After stirring for 4 h at −40° C. the reaction was quenched with water, extracted using diethyl ether (three times) and dried using $MgSO_4$. The solution was filtered through a pad of silica gel and concentrated under vacuum

Step 2: 3,3-dimethyl-6-[(4-methylphenyl)sulfonyl]-6-aza-3-silabicyclo[3.1.0]hexane To a solution of 1,1-dimethyl-2,5-dihydro-1H-silole (3.0 g, 26.7 mmol) in acetonitrile (50 mL) was added phenyltrimethylammonium tribromide (1.0 g, 2.67 mmol) and chloramine-T (6.69 g, 29.4 mmol). After stirring at rt overnight the reaction mixture was filtered though a pad of Celite and concentrated under vacuum. Purification by silica gel chromatography (20% EtOAc/hexanes) afforded the desired product.
LRMS (M+1)=281.9

Step 3: N-(1,1-dimethylsilolan-3-yl)-4-methylbenzenesulfonamide

To a 0° C. solution of 3,3-dimethyl-6-[(4-methylphenyl)sulfonyl]-6-aza-3-silabicyclo[3.1.0]hexane (0.5 g, 1.8 mmol) in THF (10 ml) was added lithium aluminum hydride (11.0M THF, 5.33 mL, 5.33 mol). After stirring at rt overnight, the reaction was quenched by the sequential addition of $H_2O$ (0.2 mL), 1N NaOH (0.2 mL), and $H_2O$ (0.6 mL). The mixture was filtered through a pad of celite and concentrated under vacuum. Purification by silica gel chromatography (20% EtOAc/hexanes) afforded the desired product.

Step 4: 1,1-dimethylsilolan-3-amine

To a solution of naphthalene (0.764 g, 5.96 mmol) in DME (6 mL) was added sodium metal (0.137 g, 5.96 mmol). After stirring the reaction mixture for 30 min a solution of N-(1,1-dimethylsilolan-3-yl)-4-methylbenzenesulfonamide (0.338 g, 1.19 mmol) in DME (5 mL) was added. The reaction mixture was stirred at rt for 2 h the quenched using ethereal HCl to pH=2 and concentrated under vacuum. The residue was dissolved in diethyl ether and water extracted with diethyl ether (three times). The aqueous layer was treated w/ NaOH until pH=10 and extracted with diethyl ether (three times), dried over $MgSO_4$ and concentrated under vacuum.

$^1$H NMR ($CDCl_3$) δ 3.13 (m, 1H), 1.88 (m, 1H), 1.49 (br, s, 2H), 1.30 (m, 1H), 1.00 (m, 1H), 0.77 (m, 1H), 0.50 (m, 1H), 0.34 (dd. J=9.5, 14 Hz, 1H), 0.15 (s, 3H), 0.11 (s, 3H).

Intermediate XXI:

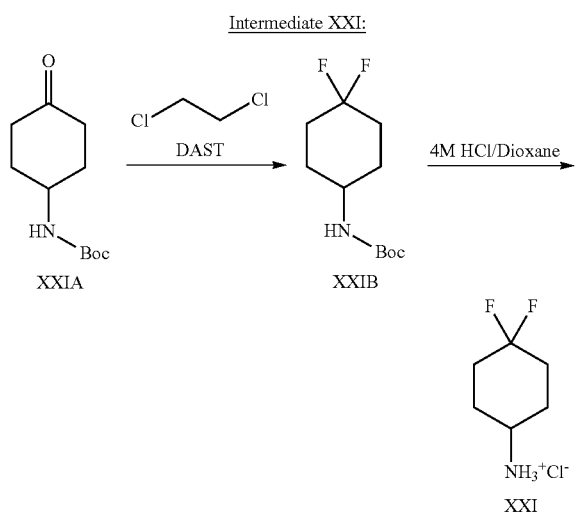

To a stirred solution of XXIA (0.85 g, 0.004 mol) in 8.0 mL dichloroethane, was added diethylaminosulfur trifluoride (0.79 mL, 0.006 mol). The mixture was stirred at 60° C. overnight, then quenched with saturated NaHCO$_3$, extracted with EtOAc (3×). The combine extracts were washed with brine, dried over anhydrous MgSO$_4$, filtered, concentrated and purified by silica gel column chromatography (ETOAc-Hex 0.5:9.5) to yield XXIB as a white solid. Compound XXIB was treated with 4M HCl/dioxane at room temperature for 1 h. The solvent was removed under reduced pressure to afford XXI as an amine-HCl salt.

EI-MS m/z: 136.20 (M+H)$^+$.

Intermediate XXII: (3S)-1-(methylsulfonyl)pyrrolidin-3-aminium chloride

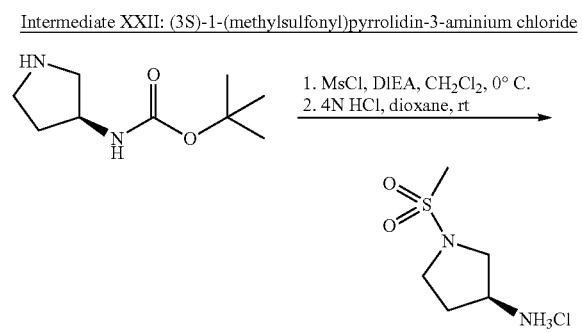

The BOC-protected aminopyrrolidine (enantiomerically pure, TCI, 1.0097 g, 5.42 mmol, 1.0 eq) was dissolved in CH$_2$Cl$_2$ (11 mL). DIEA (1.10 mL, 6.33 mmol, 1.17 eq) was added, and the reaction was stirred and cooled to 0° C. Methanesulfonyl chloride (0.50 mL, 6.46 mmol, 1.2 eq.) was added, and the reaction was stirred and allowed to warm to rt over 2 h. The reaction was diluted with CH$_2$Cl$_2$, and washed with 1N hydrochloric acid, then with saturated sodium bicarbonate solution. The organic solution was dried over magnesium sulfate, filtered, and concentrated. The crude product was dissolved in dioxane (10 mL), and 4N hydrochloric acid in dioxane (3 mL) was added. After 1 h, LCMS revealed that there was still a reasonable amount of starting material remaining, additional 3 mL of hydrochloric acid in dioxane was added, and the reaction was allowed to sit at rt for 18 h. The reaction mixture was concentrated to afford the desired amine hydrochloride.

EI-MS m/z: 165 (M+H)$^+$.

Intermediate XXIII: Trans-2-fluorocyclohexanaminium bromide

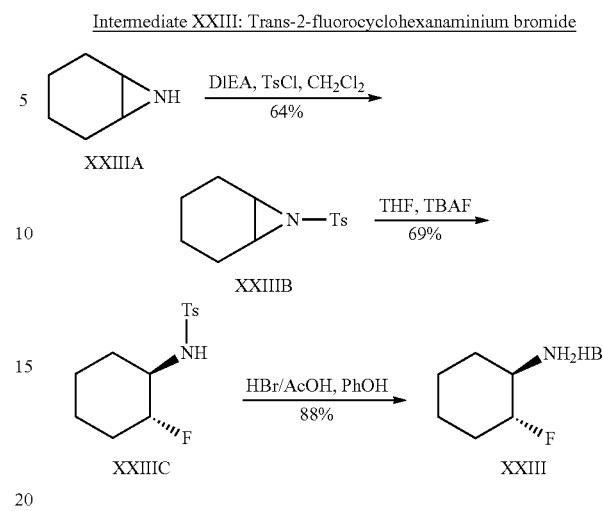

The cyclohexene imine XXXIIA was prepared according to the procedure of Watson and Yudin (J. Org. Chem. 2003, 68, 5160-5167, supp. material pg. S3). A solution of XXXIIA (5.2 g, 0.053 mol) and DIEA (9.2 mL, 0.053 mol) in CH$_2$Cl$_2$ (266.0 mL) was stirred at 0° C., and p-methyl-benzenesulfonyl chloride (10.0 g, 0.053 mol) was added slowly. The resulting mixture was stirred at rt for 2 h, quenched with water, and extracted with CH$_2$Cl$_2$ three times. The combine extracts were washed with water, saturated NaHCO$_3$, brine, and dried over anhydrous MgSO$_4$, filtered, concentrated and purified by silica gel column chromatography (EtOAc-Hexanes 1:9) to afford XXIIIB as a white solid.

EI-MS m/z: 252.15 (M+H)$^+$.

To a stirred solution of XXIIIB (8.6 g, 0.034 mol) in 68.0 mL THF, was added 37.5 mL of 1M Bu$_4$NF in THF. The resulting mixture was stirred at 45° C. until completion (monitored by TLC). The solvent was evaporated, and the crude was purified by silica gel column chromatography (EtOAc-Hexanes 2:8) to afford XXIIIC as white solid.

EI-MS m/z: 272.10 (M+H)$^+$.

A thick-walled pressure bottle was charged with XXIIIC (6.4 g, 0.024 mol), phenol (2.2 g, 0.024 mol), and 118.0 mL of 33% w/w HBr in acetic acid. The bottle was firmly stoppered, and the mixture was heated at 70° C. for 8 h. The bottle was chilled on ice. The mixture was poured into 500.0 mL of cold dry ether, and chilled using ice bath for several hours. The precipitated solid were collected and washed thoroughly with additional ether to afford XXIII as amine-HBr salt. EI-MS m/z: 118.20 (M+H)$^+$. $^1$H NMR (CD$_3$OD): δ ppm 1.3-1.6 (m, 4H), 1.7-1.9 (br m, 2H), 2.08 (m, 1H), 2.19 (m, 1H), 3.23 (m, 1H), 4.4-4.6 (2×td, J=10.27, 4.89 Hz, 1H),

Intermediate XXIV: 3,3-difluorocyclohexanaminium chloride

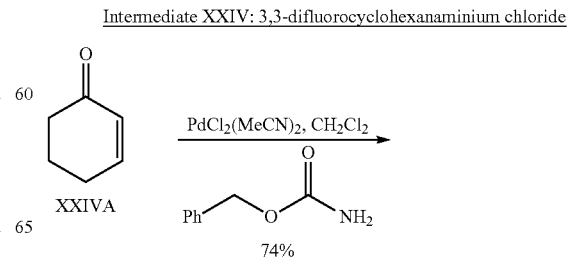

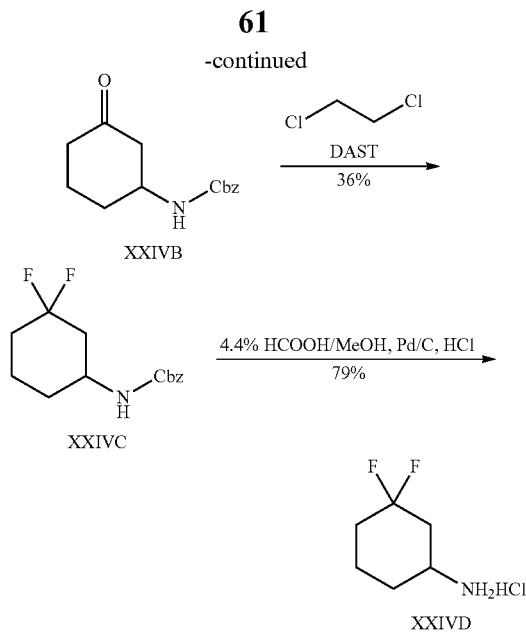

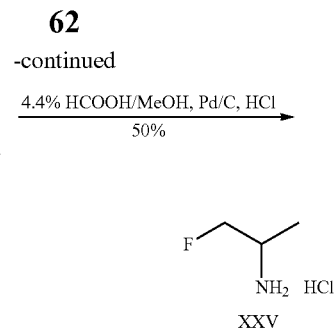

To a solution of XXIVA (1.4 ml, 0.015 mol) in 15.0 mL CH₂Cl₂, was added PdCl₂(MeCN)₂ (0.259 g, 0.001 mol) and carbamic acid benzyl ester (1.5 g, 0.010 mol). The resulting mixture was stirred at rt 24 h, filtered through a short bed of silica gel, washed with EtOAc three times, concentrated and purified by silica gel column chromatography (EtOAc-Hexanes 3:7) to yield XXIVB as a white solid.

$^1$H NMR (CD$_3$OD): δ 1.67 (m, 2H), 1.97 (m, 1H), 2.10 (m, 1H), 2.24 (m, 2H), 2.37 (m, 1H), 2.70 (dd, J=14.18, 4.40 Hz, 1H), 3.99 (br. s., 1H), 4.77 (br. s., 1H), 5.08 (s, 2H), 7.34 (m, 5H).

EI-MS m/z: 248.10 (M+H)$^+$.

To a stirred solution of XXIVB (0.988 g, 0.004 mol) in dichloroethane, was added diethylaminosulfur trifluoride (0.79 mL, 0.006 mol). The mixture was stirred at 60° C. overnight, then quenched with saturated NaHCO$_3$, and extracted with EtOAc three times. The combine extracts were washed with brine, dried over anhydrous MgSO$_4$, filtered, and concentrated. Crude XXIVC was purified by silica gel column chromatography (EtOAc-Hexanes 2:8) to yield a white solid.

EI-MS m/z: 270.10 (M+H)$^+$.

A round-bottomed flask was charged with XXIVC (0.300 g, 0.001 mol) and 23.0 mL of 4.4% formic acid/MeOH, purged with nitrogen gas, then added ~0.300 g of 10% Pd/C. The resulting mixture was stirred under nitrogen at rt until completion (monitored by LCMS). The mixture was filtered over celite followed by a MeOH rinse. The solvent was removed under reduced pressure to yield XXIV as an amine-HCOOH salt. The crude product was treated with 4N HCl/dioxane and the volatiles removed under reduced pressure. This treatment was repeated three times. The white precipitate was obtained to afford XXIV as an amine-HCl salt.

EI-MS m/z: 136.20 (M+H)$^+$.

Intermediate XXV: 1-fluoropropan-2-aminium chloride

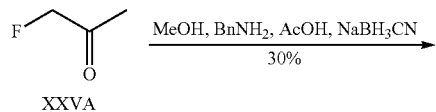

To a stirred solution of XXVA (1.4 mL, 0.020 mol), benzyl amine (2.2 mL, 0.020 mol), acetic acid (1.7 mL, 0.030 mol) in 100.0 mL MeOH, was added sodium cyanoborohydride (1.9 g, 0.030 mol) in small portions. The mixture was stirred at 60° C. overnight. After solvent removal, water was added. The product was extracted with EtOAc (three times). The combine extracts were washed with water (twice), brine, and dried over anhydrous MgSO$_4$, filtered, and concentrated to afford crude XXVB which was purified by silica gel column chromatography (EtOAc-Hexanes 3:7-4:6) to yield a yellow oil.

EI-MS m/z: 168.15 (M+H)$^+$.

XXV was synthesized in a similar manner described for XXIV above.

Compound XXVB (0.9 g, 0.005 mol) afforded XXV as an amine-HCl salt.

$^1$H NMR (CD$_3$OD): δ ppm 1.32 (dd, J=6.85, 0.98 Hz, 3H), 3.63 (br, 1H), 4.40 (dd, J=10.27, 6.36 Hz, 0.5H), 4.52 (dd, J=10.52, 6.60 Hz, 0.5H), 4.58 (dd, J=10.52, 3.18 Hz, 0.5H), 4.70 (dd, J=10.52, 3.18 Hz, 0.5H).

Intermediate XXVI: 2-isopropylcyclopropanaminium chloride

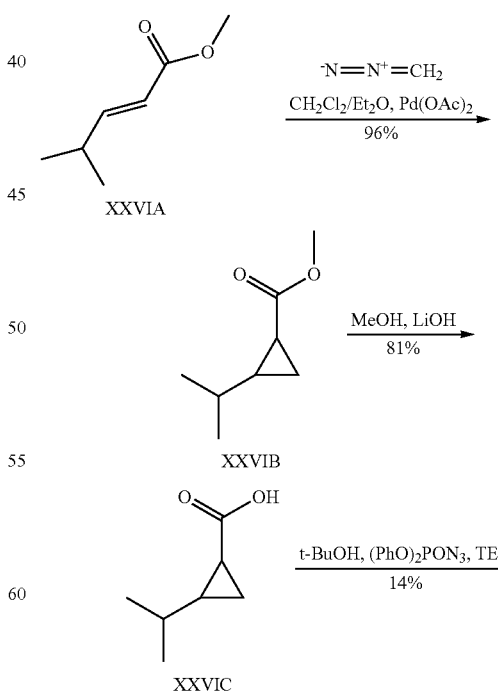

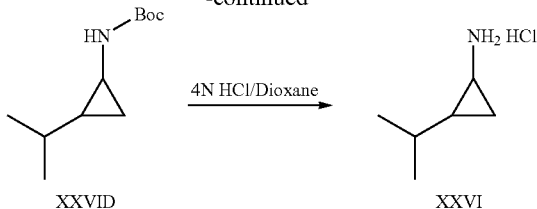

To an ice cold solution of XXVIA (1.28 g, 0.010 mol) and Palladium(II) acetate (0.017 g, 0.074 mmol) in 50.0 mL of 2:5 w/w CH$_2$Cl$_2$/Et$_2$O, was added slowly ~50.0 mL of ethereal solution of diazomethane (Caution: Diazomethane is explosive and toxic. For handling procedures, see Moore and Reed, *Org. Synth. Coll.* Vol. 5, Pg. 351, see also procedure or preparation of Intermediate XXVIII) which was prepared from N-methyl-N'-nitroso-N-nitrosoguanidine (5.9 g, 0.040 mol) right before being used. The reaction mixture was stirred at 0° C. for 1 h, allowed to warm to rt for 3 h, and quenched with few drops AcOH, extracted with Et$_2$O (twice). The combine extracts were washed twice with saturated NaHCO$_3$, once with brine, and dried over anhydrous MgSO$_4$, filtered, and concentrated to afford crude XXVIB as colorless oil. $^1$H NMR (CD$_3$OD): δ ppm 0.72 (m, 1H), 0.96 (m, 6H), 1.05 (d, J=6.85 Hz, 1H), 1.12 (m, 1H), 1.21 (m, 1H), 1.38 (m, 1H), 3.65 (s, 3H).

To a solution of crude XXVIB (1.37 g, 0.0096 mol) in 48.0 mL MeOH, was added 10.0 mL of 1M LiOH. The reaction mixture was stirred at 60° C. overnight. MeOH was removed under reduced pressure. The reaction mixture was quenched with 2N HCl, extracted with EtOAc (three times), washed with brine, and dried over anhydrous MgSO$_4$, filtered, and concentrated to afford crude XXVIC as colorless oil.

EI-MS m/z: 129.15 (M+H)$^+$.

To a solution of crude XXVIC (1.0 g, 0.0078 mol) and triethylamine (1.2 mL, 0.0086 mol) in 15.6 mL t-butyl alcohol, was added diphenyl phosphoryl azide (1.26 mL, 0.0086 mol). The reaction mixture was stirred at 90° C. overnight. t-Butyl alcohol was removed under reduced pressure. The reaction mixture was quenched with 50.0 mL of 10% Na$_2$CO$_3$, extracted three times with Et$_2$O, washed with 10% Na$_2$CO$_3$, brine, and dried over anhydrous MgSO$_4$, filtered, concentrated and purified by silica gel column chromatography (EtOAc-Hexanes 1:9) to yield XXVID as colorless oil. Compound XXVID was treated with 4N HCl/dioxane at room temperature for 1 h. The solvent was removed under reduced pressure to afford XXVI as an amine-HCl salt.

$^1$H NMR (CD$_3$OD): δ ppm 0.72 (m, 1H), 0.87 (m, 1H), 0.9-1.1 (br m, 8H), 2.40 (ddd, J=7.58, 3.67, 3.42 Hz, 1H).

Intermediate XXVII: trans-2-fluorocyclopentanaminium chloride

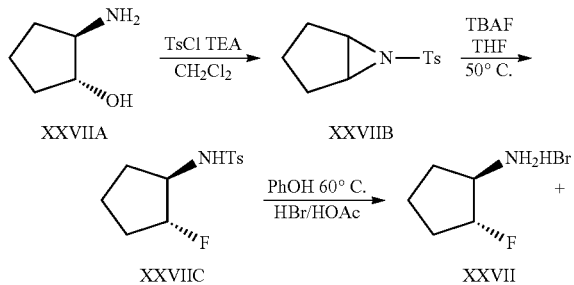

TsCl (10.1 g, 2.0 eq) was added to a stirred solution of crude racemic compound XXVIIA (2.69 g, 0.0266 mol), triethylamine (14.8 mL, 4.0 eq) in CH$_2$Cl$_2$ (60 mL). The reaction mixture was stirred overnight. The reaction mixture was extracted with saturated aqueous NaHCO$_3$/CH$_2$Cl$_2$ twice, aqueous NaH$_2$PO$_4$ (pH=4) solution/CH$_2$Cl$_2$ twice, washed with brine twice, dried with Na$_2$SO$_4$ and concentrated to afford crude compound XXVIIB Purification by Combiflash chromatography (120 g silica gel, 10% EtOAc/Hexane) gave compound XXVIIB.

EI-MS m/z: 238(M+H)$^+$.

1.0M TBAF in THF (7.0 mL, 1.3 eq) was added dropwise to a stirred solution of compound XXVIIB (1.27 g, 0.00536 mol) in THF (8 mL). The reaction mixture was stirred at 45° C. overnight. Concentration and purification by Combiflash chromatography (120 g silica gel, 10% EtOAc/Hexane) afforded compound XXVIIC.

EI-MS m/z: 258(M+H)$^+$.

Compound XXVIIC (0.712 g, 0.00277 mol) and Phenol (0.521 g, 2.0 eq) were dissolved in 33% HBr in HOAc (10 mL) under N$_2$ protection. The reaction mixture was stirred at 60° C. overnight, concentrated and dissolved in EtOAc (10-15 mL). Hexane (10-20 mL) was added until most of product precipitated. The solvent was decanted, and the precipitate was washed with Et$_2$O once. Drying in vacuo at 60° C. for 2 hours afforded compound XXVII.

EI-MS m/z: 104 (M+H)$^+$.

Intermediate XXVIII: 2-propylcyclopropanaminium

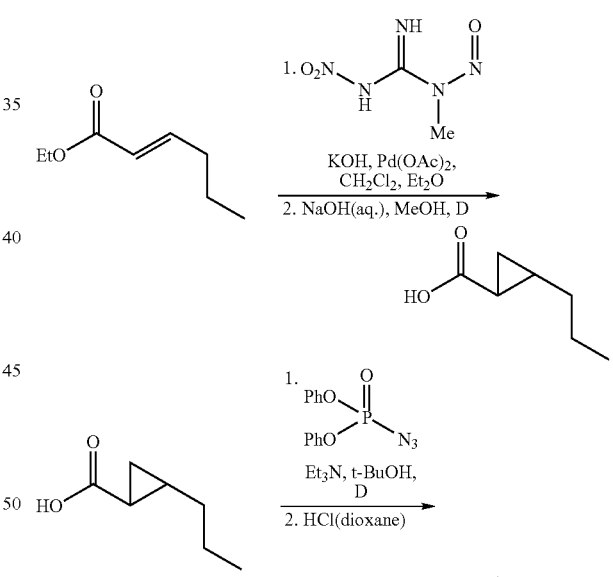

Caution: Diazomethane is explosive and toxic. For handling procedures, see Moore and Reed, *Org. Synth. Coll.* Vol. 5, Pg. 351). A solution of diazomethane was prepared as follows. A biphasic mixture of 60 mL diethyl ether and potassium hydroxide (7.0 g, 175 mmol) dissolved to a volume of 21 mL with water, were placed into a smooth 125 mL Erlenmeyer flask. The mixture was cooled to 0° C. and a blast shield placed in front of the reaction. The N-methyl-N'-nitro-N-nitrosoguanidine (8.94 g, 60.8 mmol) was added in portions over 5 minutes, with some visible gas evolution occurring with each addition. The mixture was left to sit at 0° C. for 10 min.

The ethyl trans-2-hexenoic acid (2.1441 g, 15.1 mmol) was dissolved into dichloromethane (15 mL) containing palladium diacetate (22.3 mg, 0.10 mmol, 0.007 eq.). This mixture was stirred and cooled to 0° C.

The ethereal diazomethane solution was then decanted from the Erlenmeyer flask and added to the olefin solution, in portions, using a smooth plastic pipette. The stirred reaction was then allowed to warm to rt over 1.5 h. The reaction was then cooled to 0° C., and the excess diazomethane was quenched by addition of acetic acid until gas evolution stopped. The reaction mixture was then diluted with diethyl ether, washed with saturated sodium bicarbonate solution, dried over magnesium sulfate, filtered and then concentrated to an oil. $^1$H NMR revealed the crude product to consist of a 3:1 mixture of cyclopropane:olefin. This mixture was carried on directly to the next reaction.

A portion of the crude cyclopropane ester (573.3 mg, 3.67 mmol) was dissolved into methanol (6 mL), and 4 mL of 1N NaOH (aq) solution (aq.) was added. The mixture was stirred hard and heated in an aluminum block at 70° C. for 1 h, then cooled to rt. The reaction mixture was then diluted with ether, acidified with $^1$H hydrochloric acid, and extracted twice with ether to provide the crude acid.

The acid (390.4 mg, 3.04 mmol, 1.0 eq.) was placed in a scintillation vial. tert-Butyl alcohol (5 mL) was added, followed by triethylamine (0.49 mL, 3.52 mmol, 1.16 eq.) and diphenylphosphoryl azide (942.2 mg, 3.42 mmol, 1.13 eq.). The reaction was stirred and heated to 90° C. in an aluminum block for 18 h, then cooled to rt. The reaction mixture was diluted with diethyl ether, washed with 1N hydrochloric acid, then with 10% potassium carbonate solution. The organic solution was dried over magnesium sulfate, filtered and concentrated to oil. The oil was purified by flash chromatography over silica gel (10% ethyl acetate in hexanes, using TLC and ninhydrin stain for product detection) to provide the N-Boc-amine.

The crude N-Boc-amine was dissolved into dioxane (1 mL), and treated with 4N hydrochloric acid (anhydr.) in dioxane (2 mL) for 4 h. The reaction mixture was then concentrated to a solid and placed under high vacuum for 3 days, providing the desired cyclopropylamine as the hydrochloride salt as a white solid.

$^1$H NMR (CD$_3$OD, 400 MHz) δ: 2.35 (ddd, J=7.4, 4.0, 3.4 Hz, 1H), 1.46 (ddd, J=7.3, 7.3, 7.3 Hz, 2H), 1.38-1.20 (m, 2H), 1.18-1.07 (m, 1H), 0.96 (t, J=7.4 Hz, 3H), 0.92-0.84 (m, 1H), 0.67 (ddd, J=6.8, 6.8, 6.4 Hz, 1H).

Intermediate XXIX: 2,2-difluorocyclohexanaminium chloride

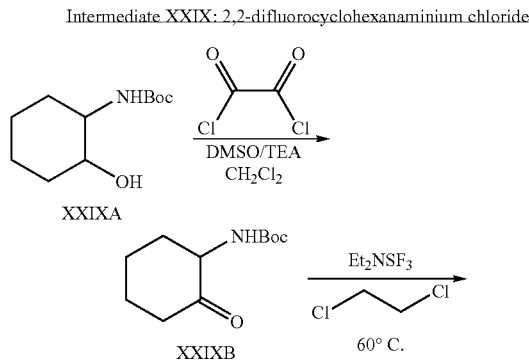

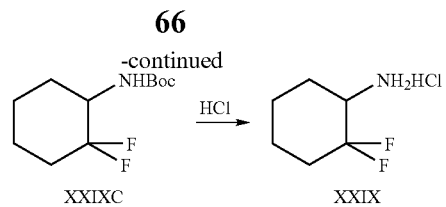

DMSO (2.51 mL, 6 eq) in CH$_2$Cl$_2$ (2 mL) was added dropwise at −78° C. to a stirred solution of oxalyl chloride (1.52 mL, 3 eq) in CH$_2$Cl$_2$ (11 mL) under N$_2$ atmosphere. After stirring for 10 min, compound XXIXA (1.27 g, 0.00590 mol) in CH$_2$Cl$_2$ (3 mL) was added dropwise. The reaction mixture was stirred at −78° C. for 6 h. TEA (4.93 mL, 6 eq) was added dropwise at −78° C. The reaction mixture was extracted with saturated aqueous NaHCO$_3$/EtOAc twice, aqueous NaH$_2$PO$_4$ (PH=4) solution/EtOAc twice, washed with brine twice, dried with MgSO$_4$ and concentrated to afford crude compound XXIXB. Purification by Combiflash chromatography (120 g silica gel, 10% EtOAc/Hexanes) gave compound XXIXB.

EI-MS m/z: 214 (M+H)$^+$.

DAST reagent (Et$_2$NSF$_3$) was added dropwise to a stirred solution of compound XXIXB (0.972 g, 0.00456 mol) in 1,2-dichloroethane (9 mL) under N$_2$ atmosphere. The reaction mixture was stirred at 60° C. overnight. Extraction with saturated aqueous NaHCO$_3$/EtOAc twice, washing with brine twice, dried with MgSO$_4$ and concentration afforded crude compound XXIXC (1.20 g). EI-MS m/z: 136 (M—C$_5$H$_8$O$_2$+H)$^+$. Crude compound XXIXC was dissolved in 4N HCl/dioxane (5 mL), stirred for 1 hour, concentrated and purified by reverse phase C-18 column to afford compound XXIX.

EI-MS m/z: 136 (M+H)$^+$.

Intermediate XXX: 2,2-difluorocyclopentanaminium chloride

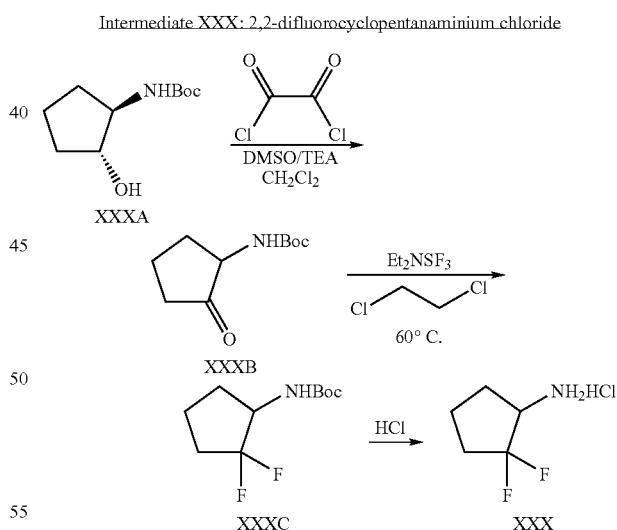

DMSO (1.92 mL, 6 eq) in CH$_2$Cl$_2$ (2 mL) was added dropwise at −78° C. to a stirred solution of oxalyl chloride (1.16 mL, 3 eq) in CH$_2$Cl$_2$ (11 mL) under N$_2$ protection. After stirring for 10 min, compound XXXA (0.905 g, 0.00450 mol) in CH$_2$Cl$_2$ (3 mL) was added dropwise. The reaction mixture was stirred at −78° C. for 6 hours. TEA (3.76 mL, 6 eq) was added dropwise at −78° C. The reaction mixture was extracted with saturated aqueous NaHCO$_3$/EtOAc twice, aqueous NaH$_2$PO$_4$ (pH=4) solution/EtOAc twice, washed with brine twice, dried with MgSO$_4$ and concentrated to afford crude compound XXXB (1.25 g). Purification by Combiflash chromatography (80 g silica gel, 8% EtOAc/Hexanes) afforded compound XXXB.

EI-MS m/z: 100 (M —$C_5H_8O_2$+H)$^+$.

DAST reagent ($Et_2NSF_3$) was added dropwise to a stirred solution of compound XXXB (0.303 g, 0.00152 mol) in 1,2-dichloroethane (3 mL) under $N_2$ atmosphere. The reaction mixture was stirred at 60° C. overnight. The reaction was extracted with saturated aqueous $NaHCO_3$/EtOAc twice, washed with brine twice, dried with $MgSO_4$, concentrated and purified by Combiflash chromatography (40 g silica gel, 5% EtOAc/Hexanes) to afford compound XXXC.

EI-MS m/z: 122 (M+H)$^+$.

Compound XXXC (0.098 g, 0.443 mmol) was dissolved in 4N HCl/dioxane (3 mL), stirred for several 20 hours, and then concentrated to afford crude compound XXX.

EI-MS m/z: 122 (M+H)$^+$.

Intermediate XXXI: cis-2-fluorocyclohexanaminium chloride

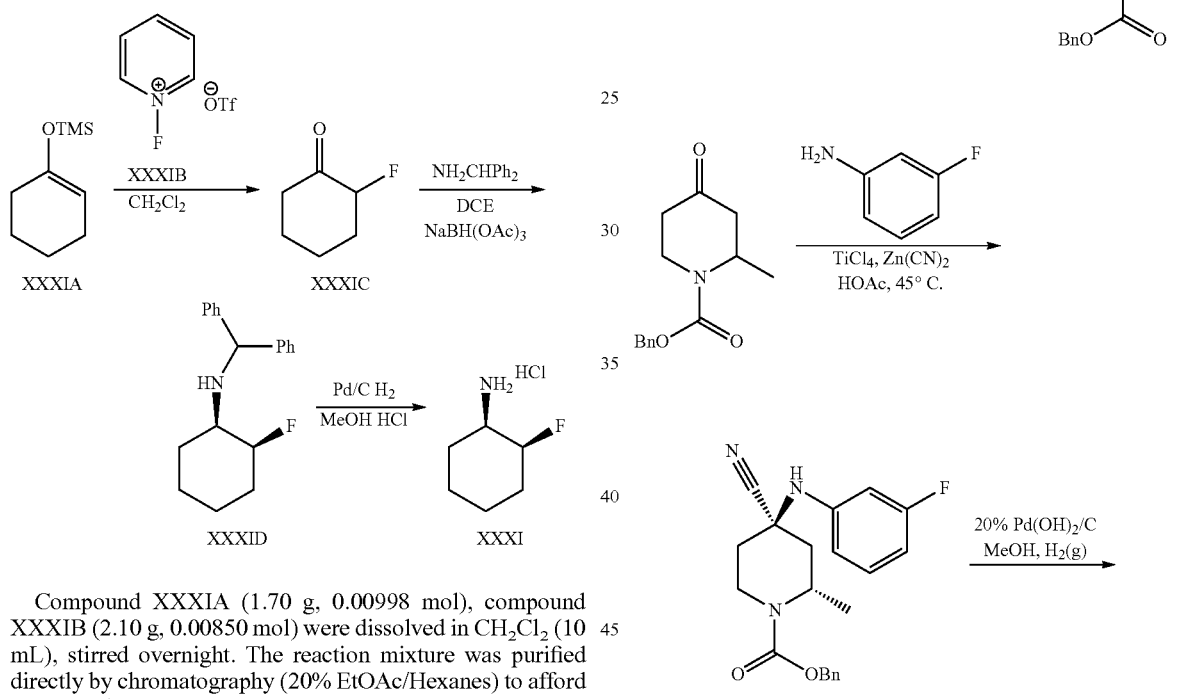

Compound XXXIA (1.70 g, 0.00998 mol), compound XXXIB (2.10 g, 0.00850 mol) were dissolved in $CH_2Cl_2$ (10 mL), stirred overnight. The reaction mixture was purified directly by chromatography (20% EtOAc/Hexanes) to afford compound XXXIC.

$^1$H NMR (CDCl$_3$). δ 4.78-4.98 (ddd, J$_{HF}$=48 Hz, J$_{HH}$=8 Hz, J'HH=4 Hz, 1H), δ 2.50-2.60 (m, 1H), δ 2.36-2.46 (m, 1H), δ 2.25-2.36 (m, 1H), δ 1.93-2.07 (m, 2H), δ 1.78-1.93 (m, 1H), δ 1.59-1.76 (m, 2H).

NaBH(OAc)$_3$ (1.718 g, 2.0 eq) was added to a stirred solution of compound XXXIC (0.471 g, 0.00405 mol), aminodiphenylmethane (0.769 mL, 1.1 eq) in 1,2-dichloroethane (10 mL). The mixture was stirred overnight. The reaction mixture was quenched with saturated aqueous NH$_4$Cl solution, extracted with $CH_2Cl_2$ twice, washed with brine twice, dried with $Na_2SO_4$ and concentrated to afford crude compound XXXID.

EI-MS m/z: 284 (M+H)$^+$.

Crude compound XXXID (0.909 g), MeOH (35 mL), 1M HCl aqueous solution (8.11 mL, 2.0 eq), and 10% Pd/C (0.458 g) were placed in a Parr flask. The mixture was hydrogenated on a Parr shaker at 40 psi for 1.5 hours. Filtration through celite, concentration and purification by reverse phase C-18 column afforded compound XXXI.

Intermediate XXXII: (5R,7S)-(5S,7R)-1-(3-fluorophenyl)-4-imino-8-(3-isopropoxybenzyl)-7-methyl-1,3,8-triazaspiro[4.5]decan-2-one

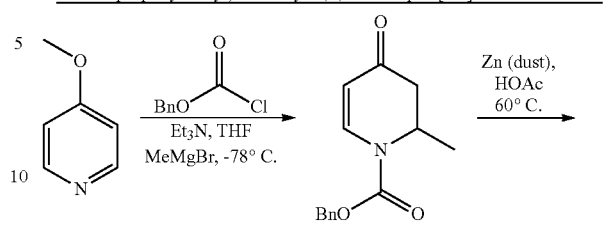

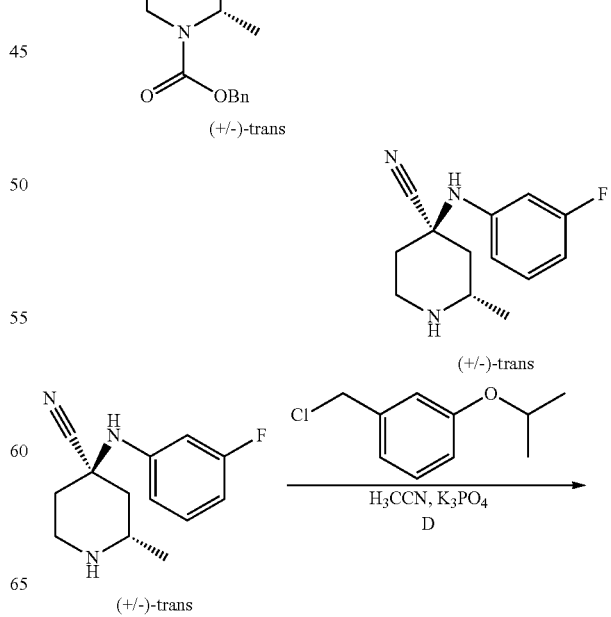

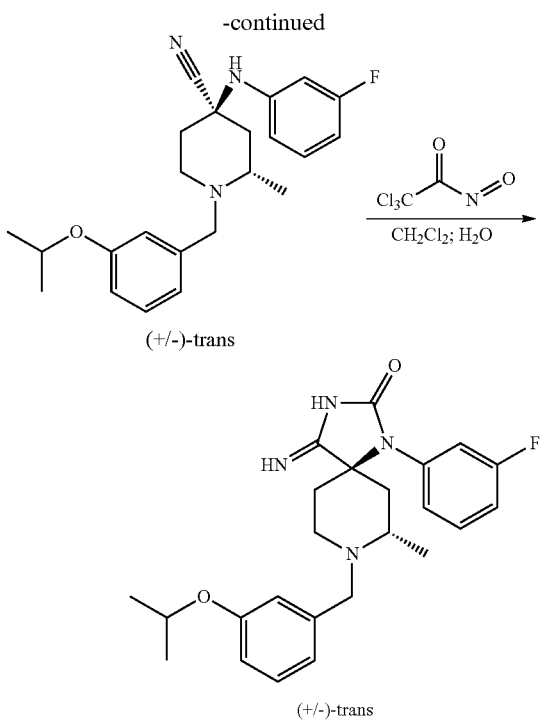

(+/-)-trans 4-methoxypyridine (5.36 g, 49.1 mmol, 1.0 eq) was weighed into a 500 mL flask with a stir bar and septum. The flask was flushed with nitrogen, and THF (80 mL) was added, followed by triethylamine (0.70 mL, 5.0 mmol, 0.10 eq). The solution was stirred and cooled to −78° C., at which point benzyl chloroformate (7.0 mL, 49.7 mmol, 1.01 eq) was added over 1 min, giving a large amount of white precipitate. An additional portion of THF (50 mL) was added to assist stirring. After stirring at −78° C. for 10 min, a 1.4M solution of methyl magnesium bromide in toluene:THF (3:1) (50 mL, 70 mmol, 1.4 equiv) was added over 1.5 min, causing most of the precipitate to go into solution. The cold bath was removed and the reaction was allowed to stir and warm to rt over 2 h. The reaction was then cooled to −10° C. in an ice salt bath, then quenched by addition of 1H hydrochloric acid. The reaction was diluted with ether, and the aqueous layer removed. The organic layer was washed with brine, dried over magnesium sulfate, filtered and concentrated to provide the desired enone, which was carried on directly to the next reaction.

$^1$H NMR (CDCl$_3$-d, 400 MHz) δ: 7.74 (br s, 1H), 7.38 (m, 5H), 5.31 (m, 1H), 5.26 (s, 2H), 4.72 (br s, 1H), 2.84 (dd, J=15.6, 7.3 Hz, 1H), 2.30 (d, J=15.6 Hz, 1H), 1.25 (br s, 3H).

EI-MS m/z: 246 (M+H)$^+$.

The enone (11.7 g, 47.7 mmol, 1 eq) was dissolved into acetic acid (70 mL), heated to 60° C., and zinc dust (12.9 g, 197 mmol, 4.14 eq) was added in 4 portions over 2.5 h. The reaction was then filtered through celite using ethyl acetate, then concentrated to an oil. The oil was dissolved into diethyl ether and water, and the aqueous layer was removed. The organic layer was washed three times with saturated sodium bicarbonate solution, then dried over magnesium sulfate, filtered and concentrated. The crude product was purified by filtration over silica gel in a Buchner funnel, using 25% ethyl acetate in hexanes to remove less polar impurities, followed by 50% ethyl acetate in hexanes to elute the desired product, which was obtained as a yellow oil after concentration.

A portion of the ketone (5.36 g, 21.7 mmol, 1.0 eq), 3-fluoroaniline (6.0 mL, 62.4 mmol, 2.88 eq) and acetic acid (70 mL) were placed in a 200 mL flask. The solution was stirred and cooled to slightly below rt in an ice bath, then a 1 M solution of titanium tetrachloride in dichloromethane (28 mL, 28 mmol, 1.29 eq) was added over 2 min. The reaction was then stirred and warmed to 50° C. in an oil bath, and zinc cyanide (10.0 g, 85.2 mmol, 3.93 eq) was added. The reaction was stirred at 50° C. for 15.5 h, at which point LCMS indicated that a small amount of ketone remained. Another portion of aniline (1.3 mL, 13.5 mmol, 0.62 eq) was added, followed by zinc cyanide (1.97 g, 16.8 mmol, 0.77 eq). LCMS after 30 min indicated that all of the ketone had been consumed. The reaction was diluted with dichloromethane and washed twice with 1N hydrochloric acid, then three times with saturated sodium bicarbonate solution. The organic solution was then dried over magnesium sulfate, filtered and concentrated to provide the aminonitrile. If desired, the mixture of trans and cis products can be separated at this stage, using silica gel chromatography, at 1.2-1.3% Et$_2$O in CH$_2$Cl$_2$, giving the desired anti isomer as the faster eluting fraction.

A portion of trans aminonitrile (1.859 g, 5.06 mmol) was dissolved into methanol (40 mL) in a Parr flask. A slurry of 20% Pd(OH)$_2$/C (247.8 mg) in ethyl acetate (2 mL) was added, and the flask was attached to a Parr shaker, and hydrogenated under 40 psi hydrogen pressure for 3.5 h. The reaction was then filtered through celite, and concentrated to an oil. If not previously separated, the cis and trans isomers are separable at this stage by silica gel chromatography (95% dichloromethane: 5% of 2N ammonia (MeOH)), with the undesired cis isomer (Rf~0.20) eluting slightly faster than the desired trans isomer (Rf~0.16).

EI-MS m/z: 234 (M+H)$^+$.

A portion of the above trans piperidine (211 mg, 0.91 mmol, 1.0 eq.) and 3-(isopropoxy)benzyl chloride (250 mg, 1.35 mmol, 1.48 eq.)) were dissolved into 5 mL of acetonitrile containing potassium carbonate (540 mg, 3.9 mmol, 4.2 eq.). The reaction mixture was stirred at 60° C. for 16 hrs and was then poured into saturated sodium bicarbonate solution. After extraction with 30 mL of dichloromethane three times, the combined organic layer was dried over sodium sulfate. The desired product was obtained by column chromatography (3% ether, 97% dichloromethane).

A portion of benzyl piperidine prepared as described above (1.7563 g, 4.60 mmol, 1.0 eq.) was placed in a flask and dichloromethane (20 mL) was added. The mixture was stirred and cooled to 0° C., and trichloroacetyl isocyanate (0.60 mL, 5.05 mmol, 1.10 eq.) was added. After stirring for 5 min, LCMS revealed that some of the starting material remained. Another portion of trichloroacetyl isocyanate (0.20 mL, 1.69 mmol, 0.37 eq.) was added. The reaction mixture was then stirred for 10 min and then water (415 µL, 23.1 mmol, 5.0 eq.) was added. The reaction mixture was then capped and placed in a −20° C. freezer overnight. The reaction was then warmed to rt and stirred hard for 2.5 h with a magnetic stirrer. The reaction was then concentrated to a white foam. Flash chromatography over silica gel (95:6.5:1 dichloromethane: methanol:saturated ammonium hydroxide (aq.) provided the desired iminohydantoin as a white solid.

$^1$H NMR (CD$_3$OD, 400 MHz) δ: 7.34 (q, J=7.7 Hz, 1H), 7.15-7.00 (m, 4H), 6.77 (d, J=8.3 Hz, 1H), 6.70-6.60 (m, 2H), 4.54 (septet, J=5.9 Hz, 1H), 3.85 (d, J=13.7 Hz, 1H), 3.14 (d, J=13.2 Hz, 1H), 2.65-2.55 (m, 1H), 2.35-2.25 (m, 1H), 2.20-2.05 (m, 3H), 2.00-1.85 (m, 2H), 1.29 (dd, J=6.1, 1.2 Hz, 6H), 1.18 (d, J=5.9 Hz, 3H).

EI-MS m/z: 425 (M+H)$^+$.

Intermediate XXXIII: (5R,7S)-(5S,7R)-1-(3-fluorophenyl)-8-(3-isopropoxybenzyl)-7-methyl-4-thioxo-1,3,8-triazaspiro[4.5]decan-2-one

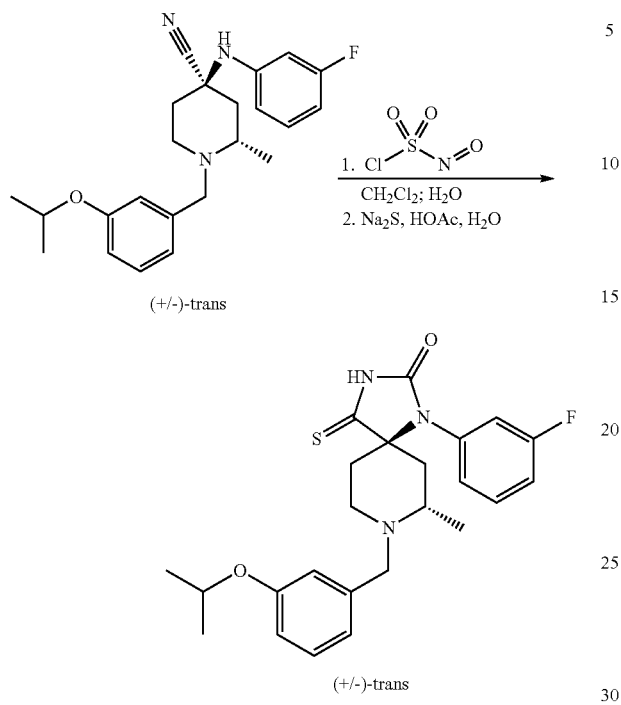

A portion of the racemic, trans aminonitrile (2.4716 g, 6.48 mmol, 1.0 eq.) was dissolved into dichloromethane (32 mL). The reaction was stirred and cooled to 0° C., at which point chlorosulfonyl isocyanate (0.76 mL, 7.77 mmol, 1.20 eq.). After 45 min, LCMS indicated that some starting material remained. Another portion of chlorosulfonyl isocyanate (0.060 mL, 0.61 mmol, 0.09 eq.) was added. After 5 min, water (10 mL) was added, and the biphasic mixture was stirred hard.

In a 1 L glass bottle with a plastic cap, a solution of anhydrous sodium sulfide (9.79 g, 125 mmol, 19.4 eq.) in water (150 mL) was prepared and cooled to an internal temperature of less than 5° C. Acetic acid (10.3 mL, 180 mmol, 27.8 eq.) was added dropwise over 10 min, keeping the internal temperature below 8° C., causing moderate gas evolution. The dichloromethane solution of the iminohydantoin was then added to the thiol solution, using a total of 20 mL additional dichloromethane for the transfer. The bottle was then capped, stirred hard and allowed to warm to rt. After two days of stirring, the reaction was diluted with ethyl acetate, and the organic layer was removed. The organic layer was washed with saturated sodium bicarbonate solution, then with brine. The organic solution was then dried over magnesium sulfate, filtered and concentrated. Flash chromatography over silica gel (25% ethyl acetate in hexanes) provided the desired thiohydantoin.

$^1$H NMR (CD$_3$OD, 400 MHz) δ: 7.40-7.30 (m, 1H), 7.15-7.05 (m, 2H), 7.01 (d, J=7.4 Hz, 1H), 6.94 (d, J=8.8 Hz, 1H), 6.80-6.60 (m, 3H), 4.52 (septet, J=5.9 Hz, 1H), 3.86 (d, J=13.7 Hz, 1H), 3.15-2.85 (m, 1H), 2.85-2.40 (m, 2H), 2.40-2.15 (m, 1H), 2.05-1.70 (m, 4H), 1.32 (d, J=6.3 Hz, 6H), 1.25-1.05 (m, 2H).

EI-MS m/z: 442 (M+H)$^+$.

Example 1

Racemic 5(R,S)7(R,S)-8-benzyl-4-(cyclohexylamino)-1-(3-fluorophenyl)-7-methyl-1,3,8-triazaspiro[4.5]dec-3-en-2-one diastereomer A

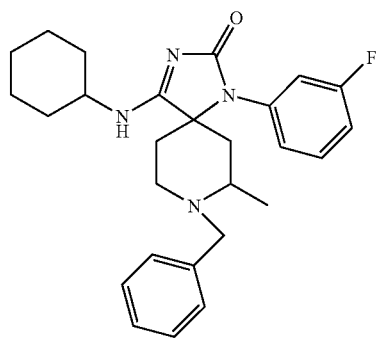

In a flask 1-benzyl-2-methylpiperidin-4-one (Intermediate 1,163 mg, 0.8 mmol) was dissolved in MeOH (0.275 mL) and a solution of KOCN (0.11 mL of an approximately 9 Molar solution made from dissolving 0.81 mg KOCN in 1.1 mL water) was added in one portion with vigorous stirring. Cyclohexyl isocyanide (0.096 mL, 0.76 mmol) was added, followed by powdered aniline hydrochloride (0.118 g, 0.802 mmol, added in small portions over 5 minutes). The reaction was stirred overnight, then evaporated and the residue portioned between CHCl$_3$ and saturated bicarbonate solution, the organic was dried with Na$_2$SO$_4$, filtered and evaporated. The residue was chromatographed on a reverse phase column eluting with a gradient of 5-95% CH$_3$CN/water 0.1% TFA. The earlier eluting of two diastereomers was isolated after lyophilization of the fractions and its free base obtained by partitioning between CHCl$_3$ and saturated bicarbonate. The organic layer was dried (Na$_2$SO$_4$) filtered and evaporated to give the product as a foam.

$^1$H NMR (400 MHz, CDCl$_3$) δ 7.7 (d, J=7.8 Hz, 1H), 7.4-7.28 (m, 6H), 7.0 (m, 3H), 3.99 (m, 1H), 3.70 (d, J=13.5 Hz, 1H), 3.62 (d, J=13.5 Hz, 1H), 3.1 (m, 1H), 2.73 (m, 1H), 2.55 (m, 1H), 2.03 (m, 3H), 1.90 (m, 1H), 1.8-1.6 (m, 4H), 1.38 (m, 2H), 1.2-1.0 (m, 3H), 1.15 (d, J=6.2 Hz, 3H) ppm.

Example 2

Racemic 5(R,S)7(S,R)-8-benzyl-4-(cyclohexylamino)-1-(3-fluorophenyl)-7-methyl-1,3,8-triazaspiro[4.5]dec-3-en-2-one Diastereomer B

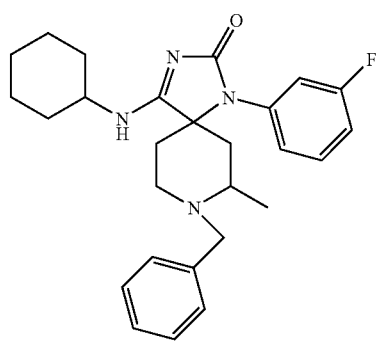

In a pear-shaped flask Intermediate I (0.800 mg, 3.93 mmol) was dissolved in MeOH (1.3 mL) and a solution of KOCN (0.547 mL of an approximately 9 Molar solution made from dissolving 0.81 mg KOCN in 1.1 mL water) was added in one portion with vigorous stirring. Cyclohexyl isocyanide (0.473 mL, 3.74 mmol) was added, followed by powdered 3-fluoroaniline hydrochloride (prepared by treating an ice-cooled solution of 3-fluoroanaline in ether with a 1 Molar solution of HCl in ether and isolated either by evaporating to give the solid or by filtering off and collecting the solid precipitate) 0.581 g, 3.93 mmole, added in small portions over 5 min). The reaction was stirred 48 hr, then partioned between CHCl$_3$ and saturated bicarbonate solution, the organic was dried with Na$_2$SO$_4$, filtered and evaporated. The residue was chromatographed on silica eluting with a gradient of 0-5% MeOH/CHCl$_3$ and the earlier and later diastereomeric products were isolated. The later eluting diastereomer was further purified by reverse phase column eluting with a gradient of 10-95% CH$_3$CN/water 0.1% TFA. The pure fractions were evaporated and the free base obtained by partitioning between CHCl$_3$ and saturated bicarb. The organic layer was dried (Na$_2$SO$_4$) filtered and evaporated to give the product as a foam.

$^1$H NMR (400 MHz, CDCl$_3$) δ 8.24 (d, J=7.7 Hz, 1H), 7.4-7.3 (m, 4H), 7.2 (buried), 7.0 (m, 3H), 4.15 (d, J=12.8 Hz, 1H), 3.94 (m, 1H), 3.0 (d, J=12.8 Hz, 1H), 2.78 (m, 1H), 2.58 (m, 1H), 2.24 (dd, J=7.0, 14.5 Hz, 1H), 2.1 (m, 3H), 1.95-1.8 (m, 4H), 1.75-1.5 (m, 3H), 1.35 (m, 2H), 1.28 (d, J=6.4 Hz, 3H), 1.2 (m, 1H), 1.0 (m, 1H).

Example 2 was separated into its enantiomers 2a and 2b by reverse phase chiral chromatography on a ChiralPak AD 5 cm×50 cm 20 g prep column eluting with a gradient of 90/10 to 40/60 hexanes/EtOH containing 0.1% diethylamine monitored at 265 nM.

The first eluting enantiomer 2a was further purified by nonchiral reverse phase HPLC and the free base isolated from partition between saturated bicarbonate and CHCl$_3$.

5(R),7(S)-8-benzyl-4-(cyclohexylamino)-1-(3-fluorophenyl)-7-methyl-1,3,8-triazaspiro[4.5]dec-3-en-2-one $^1$H NMR (400 MHz, CDCl$_3$) δ 8.24 (d, J=7.7 Hz, 1H), 7.4-7.3 (m, 4H), 7.25 (buried), 7.0 (m, 3H), 4.14 (d, J=12.6 Hz, 1H), 3.95 (m, 1H), 3.0 (d, J=12.8 Hz, 1H), 2.79 (m, 1H), 2.58 (m, 1H), 2.24 (dd, J=7.0, 14.8 Hz, 1H), 2.2-2.0 (m, 3H), 1.9-1.75 (m, 3H), 1.75-1.6 (m, 3H), 1.45-1.3 (m, 2H), 1.25 (d, J=6.2 Hz, 3H), 1.2 (m, 1H), 1.0 (dq, J=3.6, ~12 (×3) Hz) ppm.

Second eluting enantiomer 2b. The material obtained from the chiral column were partitioned between saturated bicarbonate and CHCl$_3$, dried with Na$_2$SO$_4$, filtered and evaporated to give the product.

5(S),7(R)-8-benzyl-4-(cyclohexylamino)-1-(3-fluorophenyl)-7-methyl-1,3,8-triazaspiro[4.5]dec-3-en-2-one $^1$H NMR (400 MHz, CDCl$_3$) δ 8.27 (d, J=8.2 Hz, 1H), 7.4-7.3 (m, 4H), 7.25 (buried), 7.0 (m, 3H), 4.14 (d, J=12.8 Hz, 1H), 3.95 (m, 1H), 3.0 (d, J=12.8 Hz, 1H), 2.79 (m, 1H), 2.58 (m, 1H), 2.24 (dd, J=7.1, 14.4 Hz, 1H), 2.2-2.0 (m, 3H), 1.9-1.75 (m, 3H), 1.75-1.6 (m, 3H), 1.45-1.3 (m, 2H), 1.28 (d, J=6.2 Hz, 3H), 1.2 (m, 1H), 1.0 (dq, J=3.1, ~12 (×3) Hz) ppm.

In a manner similar to that described for Examples 1 and 2, using the appropriate intermediates outlined above and the appropriate amine and isocyanide, the following compounds of Table 1 were prepared:

TABLE 1

| Ex. No. | Intermediate | Structure | IUPAC Name | Mass Spec M + 1 Data |
|---|---|---|---|---|
| 3 | II | 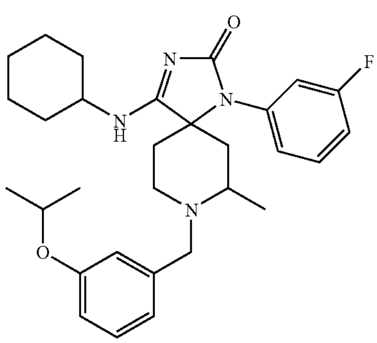 | Racemic 5(R,S)7(R,S)-4-(cyclohexylamino)-1-(3 fluorophenyl)-8-(3-isopropoxybenzyl)-7-methyl-1,3,8-triazaspiro[4.5]dec-3-en-2-one Diastereomer A | 507.5 |
| 4 | II | 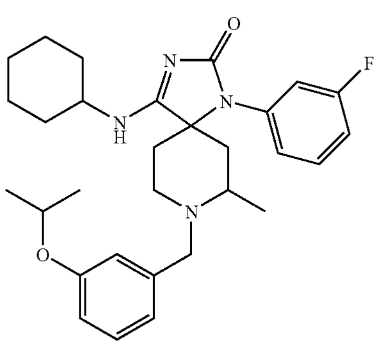 | Racemic 5(R,S)7(S,R)-4-(cyclohexylamino)-1-(3-fluorophenyl)-8-(3-isopropoxybenzyl)-7-methyl-1,3,8-triazaspiro[4.5]dec-3-en-2-one Diastereomer B | 507.5 |

TABLE 1-continued

| Ex. No. | Intermediate | Structure | IUPAC Name | Mass Spec M + 1 Data |
|---|---|---|---|---|
| 5 | I | 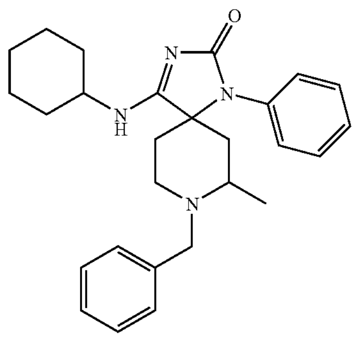 | Racemic 5(R,S)7(R,S)-8-benzyl-4-(cyclohexylamino)-7-methyl-1-phenyl-1,3,8-triazaspiro[4.5]dec-3-en-2-one Diastereomer A | 431.4 |
| 6 | I | 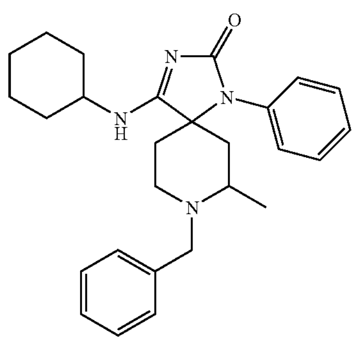 | Racemic 5(R,S)7(S,R)-8-benzyl-4-(cyclohexylamino)-7-methyl-1-phenyl-1,3,8-triazaspiro[4.5]dec-3-en-2-one Diastereomer B | 431.4 |
| 7 | II | 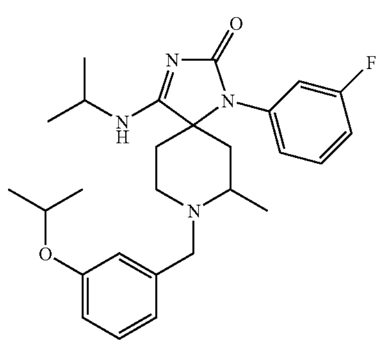 | Racemic 5(R,S)7(R,S)-8-(3-isopropoxybenzyl)-4-(isopropylamino)-7-methyl-1-(3-methylphenyl)-1,3,8-triazaspiro[4.5]dec-3-en-2-one Diastereomer A | 467.5 |
| 8 | II | 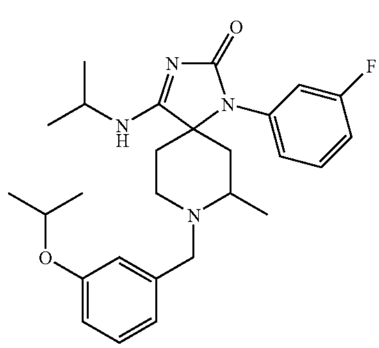 | Racemic 5(R,S)7(S,R)-8-(3-isopropoxybenzyl)-4-(isopropylamino)-7-methyl-1-(3-methylphenyl)-1,3,8-triazaspiro[4.5]dec-3-en-2-one Diastereomer B | 467.5 |

TABLE 1-continued

| Ex. No. | Intermediate | Structure | IUPAC Name | Mass Spec M + 1 Data |
|---|---|---|---|---|
| 9 | I | 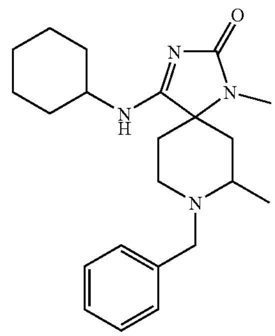 | 5(R,S)7(R,S)-8-benzyl-4-(cyclohexylamino)-1,7-dimethyl-1,3,8-triazaspiro[4.5]dec-3-en-2-one Diastereomer A | 369.1 |
| 10 | I | 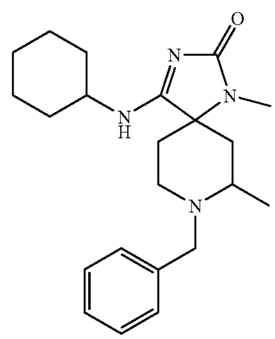 | 5(R,S)7(S,R)-8-benzyl-4-(cyclohexylamino)-1,7-dimethyl-1,3,8-triazaspiro[4.5]dec-3-en-2-one Diastereomer B | 369.1 |

Examples 1 to 10 are depicted above in enamine form, but may also exist in tautomeric imine form, as described above.

Example 11

(5R,7S)-4-(cyclohexylamino)-1-(3-fluorophenyl)-8-(3-isopropoxybenzyl)-7-methyl-1,3,8-triazaspiro[4.5]dec-3-en-2-one (R,S enantiomer of Example 4)

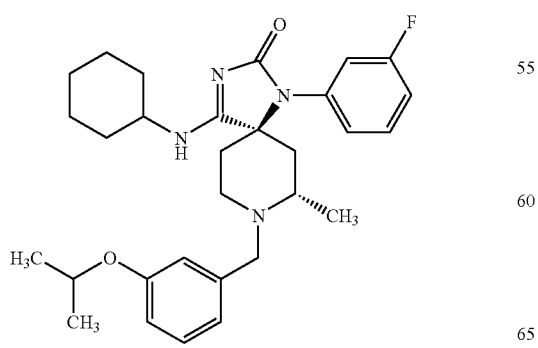

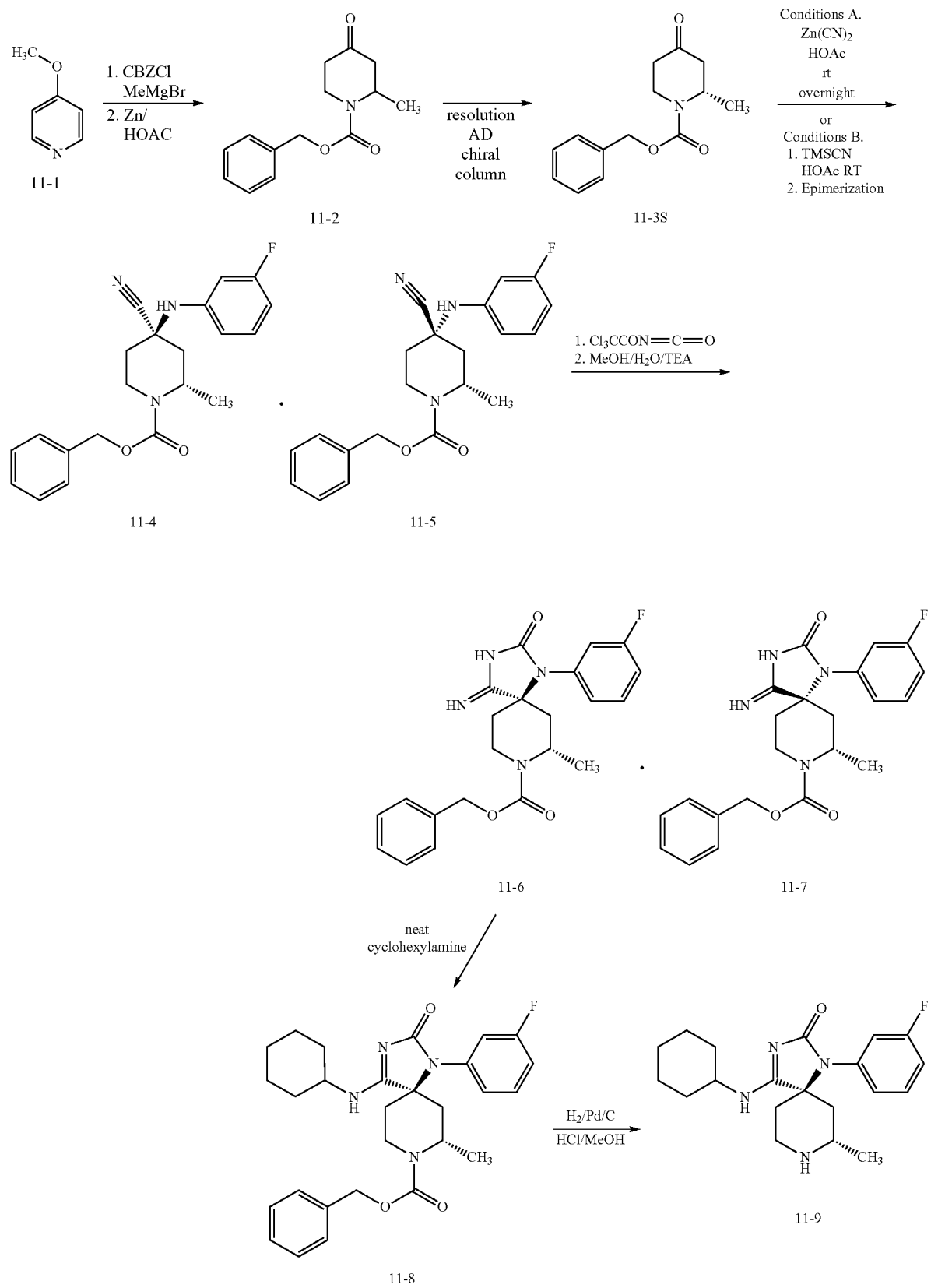

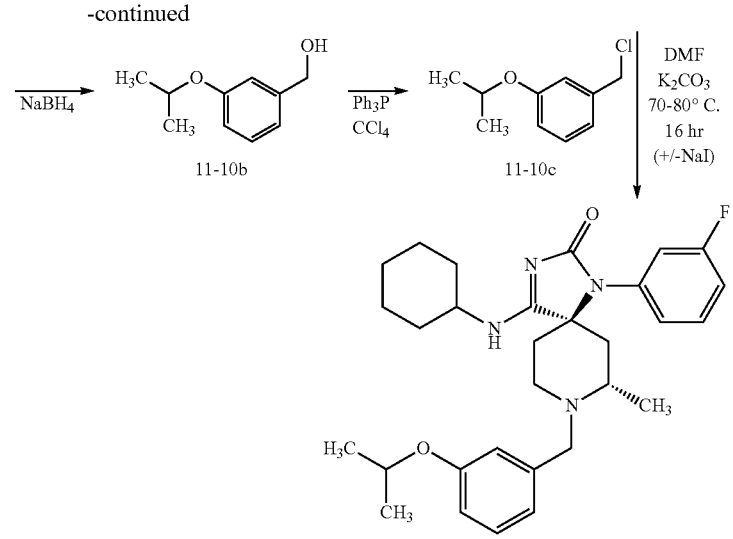

11-10 (Example 11)

Step 1: Racemic Benzyl 2-methyl-4-oxo-3,4-dihydropyridine-1(2H)-carboxylate 11-2

4-methoxypyridine (796 g, 7.29 mole) was stirred in 8 L of anhydrous THF in a 20 L reactor. The reactor was cooled to −30° C., then methylmagnesium bromide (5.1 L, 7.29 mole) was added as a 1.4M solution in 3:1 toluene/THF was added via cannula one 800 mL bottle at a time with 800 mls added over a 5 min time period. After the addition was complete and the reaction temperature was −30° C., benzyl chloroformate (1244 g, 7.29 mole) was added dropwise over a 60 min period via addition funnel. The warmest temperature reached was 16° C. After addition was complete the reaction was warmed to 25° C. and stirred for 1.5 hrs. The reaction was cooled to 0° C. and quenched with 4.0 L of 2 N HCl. 4 L of MTBE and brine was added and the layers separated. The temperature was now 25° C. The aqueous phase was extracted with 2×2 L of MTBE. The combined organics were washed with brine and dried over $Na_2SO_4$, filtered and concentrated to give the crude oil. Chromatography using a Varian Metaflash 150 long (15 cm×60 cm long 5 kilo silica) and eluting with 10-35% EtOAc/Heptanes gave the product as an oil.

$^1$H NMR (400 MHz, $CDCl_3$) δ 7.85 (dd, J=1.5, 8.2 Hz, 1H), 7.38 (m, 6H), 5.31 (d, J=12 Hz, 1H), 5.27 (d, J=12 Hz, 1H), 4.74 (m, 1H), 2.92 (dd, J=7.17 Hz, 1H), 2.26 (d, J=17 Hz, 1H), 1.21 (d, J=7 Hz, 3H).
LCMS observed mass=202

Step 2: Reduction to Racemic benzyl 2-methyl-4-oxopiperidine-1-carboxylate 11-3

Benzyl 2-methyl-4-oxo-3,4-dihydropyridine-1(2H)-carboxylate (823 g, 3.35 mole) was stirred in 5 L of glacial acetic acid and heated to 90° C. under argon in a 20 L reactor. Zinc dust (218 g, 3.35 mole) was added and the reaction heated to 100° C. for 1 h. Several more 0.25-0.5 eq portions of zinc dust were added over the next few hrs, the reaction was allowed to cool to ambient temperature overnight, then re-heated and treated with further portions of zinc dust (total 10 hr 100° C., 548 g, 8.43 mole, 2.5 eq zinc). The reaction was filtered through a pressed pad of Celite, rinsing with 4.0 L of HOAc. The zinc pad was never allowed to dry and the temperature of the zinc pad was monitored by thermocouple. The pad was washed with copious amounts of $H_2O$ and stored under water until disposal. The filtrate was concentrated and co-evaporated with toluene to give crude product that was diluted with 700 mL 10% EtOAc/Heptane and ~200 ml $CH_2Cl_2$ was added to form a single phase. This material was loaded onto a Varian 150 M (2.5 Kg) silica gel column and eluted with a gradient of 10% EtOAc to 40% EtOAc in Heptane. The fractions were concentrated to give the crude product as an oil. The crude material may be treated with a workup from aqueous bicarbonate.

$^1$H NMR (400 MHz, $CDCl_3$) δ 7.37 (m, 5H), 5.18 (s, 2H), 4.80 (m, 1H), 4.34 (m, 1H), 3.38 (m, 1H), 2.7(dd, J=6.7, 18 Hz, 1H), 2.5 (m, 1H), 2.2-2.4 (m, 2H), 1.2 (d, J=7 Hz, 1H).
LCMS observed mass=248.2 (m+1)

Step 3: Resolution to benzyl (2S)-2-methyl-4-oxopiperidine-1-carboxylate 11-3S

The crude Racemic benzyl 2-methyl-4-oxopiperidine-1-carboxylate was dissolved in MeOH and chromatographed on a 10 cm Chiralpak AD column eluting with 100% MeOH in 2.5 g injections to give the two separated enantiomers. The desired enantiomer eluted first, 95% ee.

Step 4: Benzyl (2S,4R)-4-cyano-4-[(3-fluorophenyl) amino]-2-methylpiperidine-1-carboxylate 114 and benzyl (2R,4R)-4-cyano-4-[(3-fluorophenyl)amino]-2-methylpiperidine-1-carboxylate 11-5

Conditions A: $Zn(CN)_2$
CBZ piperidinone 7-3S (30.2 g, 0.122 mole) was dissolved in 240 mL of glacial acetic acid and 3-fluoroaniline (13.55 g, 0.122 mole) was added followed by zinc cyanide (71.6 g, 0.61 mole). In an alternative method, 2.5 equivalents of Zinc Cyanide may be used. The reaction was stirred at room temperature overnight then poured into an equal volume of ice/ammonium hydroxide solution (260 mL) and the pH adjusted until it was basic. The basic solution was extracted three times with chloroform and the organics were dried over $MgSO_4$, filtered and evaporated. The crude material loaded directly onto a silica gel column and chromatographed with 30%

Ethyl acetate/Hexanes to give the products as a viscous yellow oil. The diastereomers were not separated at this point.

$^1$H NMR (400 MHz, CDCl$_3$ mixture of diastereomers) δ 7.36 (m, ~12H), 7.21 (m, ~2H), 6.63 (m, ~6H), 6.42 (m, ~1H), 5.18 (s, ~1H), 5.15 (s, ~4H), 4.9 (bs, ~1H), 4.8 (m, ~1H), 4.6 (m, ~1H), 4.28-4.2 (m, ~2H), 4.0 (m, ~1H), 3.84 (s, ~1H), 3.76 (s, ~1H), 3.4-3.2 (m, ~3H), 2.7 (m, ~1H), 2.6-2.2 (m, ~9H), 1.95 (m, ~1H), 1.85 (m, ~1H), 1.45 (d, J=7 Hz, ~3H), 1.2 (d, J=7 Hz, ~2H).
LC/MS ion fragment mass of 251

Step 4: Benzyl (2S,4R)-4-cyano-4-[(3-fluorophenyl)amino]-2-methylpiperidine-1-carboxylate 11-4 and benzyl (2R,4R)-4-cyano-4-[(3-fluorophenyl)amino]-2-methylpiperidine-1-carboxylate 11-5

Conditions B: TMSCN/AcOH and Epimerization

CBZ piperidinone 7-3S (13.91 g, 0.056 moles) was dissolved in 56 mL of Glacial acetic acid and cooled to 0° C. 3-fluoroaniline (6.5 g, 0.059 moles) was added followed by dropwise addition of TMSCN (6.7 g, 9 mL, 0.067 moles). The reaction was stirred at rt for a few hours, an additional 0.5 ml of aniline and 1 mL of TMSCN was added and the reaction stirred until starting material was consumed (overnight). Some crystalline product was filtered off and washed with hexanes. The volume of the mother liquor was reduced in vacuo and then poured into an ice/ammonium hydroxide solution. The solution was extracted two times with dichloromethane and the organics were dried over Na$_2$SO$_4$, filtered and evaporated. The crude material was loaded directly onto a silica gel column and eluted with 40% diethyl ether/hexanes and 30% ethylacetate/hexanes, to give the product as an amber oil. The combined products were dissolved in EtOH (150 mL). To this TMSCN was added (15 mL, 0.110 Mol) and the mixture sealed and heated in an 85° C. oil bath for 6 h. The mixture was concentrated to dryness to yield the crude product as an oil. The crude material was loaded directly onto a silica gel column and then eluted with 40% diethyl ether/hexanes and 30% ethylacetate/hexanes to give the products as an amber oil.

$^1$H NMR (400 MHz, CD$_3$OD, mixture of diastereomers) δ 7.35 (m, ~5H), 7.3(m, ~2H), 7.2-7.1 (m, ~1.5H), 6.68 (m, ~1.5H), 6.6 (m, ~1.5H), 6.5 (m, ~1.5H), 5.13 (ABq, ~3H), 4.55 (m, ~1H), 4.38 (m, ~0.5H), 4.2 (m, ~1H), 4.0 (m, ~0.5H), 3.4-3.3 (m, ~3H), 2.5 (m, ~2.5H), 2.25 (m, ~1H), 2.15 (m, ~1H), 1.9 (m, ~1H), 1.7 (m, ~1H) ppm.
LCMS (m+1)=251.2

Step 5: Cyclization to benzyl (5R,7S)-1-(3-fluorophenyl)-4-imino-7-methyl-2-oxo-1,3,8-triazaspiro[4.5]decane-8-carboxylate 11-6 and benzyl (5R,7R)-1-(3-fluorophenyl)-4-imino-7-methyl-2-oxo-1,3,8-triazaspiro[4.5]decane-8-carboxylate 11-7

The mixture of benzyl (2S,4R) and (2R,4R)-4-cyano-4-[(3-fluorophenyl)amino]-2-methylpiperidine-1-carboxylate and benzyl (2R,4R)-4-cyano-4-[(3-fluorophenyl)amino]-2-methylpiperidine-1-carboxylate (43.7 g, 0.119 moles) was dissolved in 400 mL CH$_2$Cl$_2$ and trichloroacetylisocyanate (29.2 g, 0.155 moles) was added via pipette. The reaction turned red instantly and faded over 15 min, the reaction was monitored by LCMS and the reaction to form the acylated intermediate was done in 10 min. The reaction was stirred at rt for another 45 min and again showed no starting material by LCMS. 50 mL of MeOH was added followed by 20 mL of water and 27 mL (0.155 moles) of Hunig's base. The reaction was heated at 50° C. for 4 hrs, when LCMS showed the cyclization was done. The reaction was diluted with CH$_2$Cl$_2$, washed with brine and dried over MgSO$_4$, filtered and evaporated to give the crude product, which was chromatographed on silica with 10% MeOH/CHCl$_3$/1% Triethylamine. The desired isomer eluted after the undesired isomer to give the desired product as a white solid.

$^1$H NMR (400 MHz, CD$_3$OD) δ 7.3 (m, 4H), 7.23 (bd, J=7 Hz, 2H), 7.12 (m, 2H), 7.04 (dt, J=2, 8 Hz, 1H), 4.92 (d, J=12.3 Hz, 1H), 4.67 (bd, J=11 Hz, 1H), 3.95 (dd, J=7.14 Hz, 1H), 3.46 (m, 1H), 3.12 (m, 1H), 2.56 (m, 1H), 2.19 (m, 1H), 1.94 (dd, J=11.5, 14.7 Hz, 1H), 1.01 (d, J=6.2 Hz, 3H) ppm. acylated intermediate LCMS ion fragment detected=207.1 desired iminohydantoin product LCMS ion fragment detected=410.9

Step 6: Benzyl (5R,7S)-4-(cyclohexylamino)-1-(3-fluorophenyl)-7-methyl-2-oxo-1,3,8-triazaspiro[4.5]dec-3-ene-8-carboxylate 11-8

Benzyl (5R,7S)-1-(3-fluorophenyl)-4-imino-7-methyl-2-oxo-1,3,8-triazaspiro[4.5]decane-8-carboxylate (27.2 g, 0.066 moles) was dissolved in 100 mL toluene, cyclohexylamine (60 mL, 0.523 moles) was added and the mixture was heated to 110° C. over the weekend in a 1 L roundbottom flask fitted with a condenser. The reaction was diluted with CHCl$_3$ and MeOH until soluble and washed with 1 Normal HCl three times to remove excess cyclohexylamine. The organic was dried with MgSO$_4$, filtered and concentrated to give the product which was used in the next step without further purification.

$^1$H NMR (400 MHz, CDCl$_3$) δ 7.42-7.10 (m, 9H), 4.88-4.81 (m, 2H), 4.66 (d, J=11.6 Hz), 3.98 (dd, J=7.3, 14.1 Hz, 1H), 3.66 (m, 1H), 3.55 (m, 1H), 3.24 (ddd, J=5.6, 12.4, 14.2 Hz, 1H), 2.78 (m, 1H), 2.54 (dd, J=7.0, 14.6 Hz, 1H), 2.24 (dd, J=5.1, 16.0 Hz, 1H), 2.03 (m, 2H), 1.84 (m, 2H), 1.69 (m, 1H), 1.73-1.23 (m 3H), 1.05 (d, J=6.1 Hz, 3H).
LCMS ion fragment=493.01

Step 7: (5R,7S)-4-(cyclohexylamino)-1-(3-fluorophenyl)-7-methyl-1,3,8-triazaspiro[4.5]dec-3-en-2-one (11-9)

Benzyl (5R,7S)-4-(cyclohexylamino)-1-(3-fluorophenyl)-7-methyl-2-oxo-1,3,8-triazaspiro[4.5]dec-3-ene-8-carboxylate (27.9 g, 0.057 moles) was suspended in MeOH (~200 mL) and methanolic HCl was added until the solids all went into solution. Pd(OH)$_2$ (4 g, moisture content 60%) was added and the reaction was flushed with hydrogen and kept under a hydrogen balloon. The reaction was stirred at room temperature for 30 min. The reaction was evacuated and recharged with H$_2$ once to remove CO$_2$. The reaction was filtered through celite and concentrated, then the free base was obtained by portioning between CHCL$_3$ and 1 N NaOH. The organic was dried over MgSO$_4$, filtered and evaporated to give the product.

$^1$H NMR (400 MHz, CD$_3$OD) δ 7.45 (m, 1H), 7.18 (m, 3H), 3.74 (m, 2H), 2.85 (m, 1H), 2.50 (m, 2H), 2.1 (m, 2H), 1.96 (m, 3H), 1.81 (m, 4H), 1.6 (m, 2H), 1.5-1.05 (m, 6H), 0.98 (d, J=6 Hz, 3H) ppm.
LCMS ion mass fragment=359.0

Step 8: (5R,7S)-4-(cyclohexylamino)-1-(3-fluorophenyl)-8-(3-isopropoxybenzyl)-7-methyl-1,3,8-triazaspiro[4.5]dec-3-en-2-one (11-10)

(5R,7S)-4-(cyclohexylamino)-1-(3-fluorophenyl)-7-methyl-1,3,8-triazaspiro[4.5]dec-3-en-2-one (17 g, 0.0475 moles) was dissolved in DMF (200 mL) and powdered K$_2$CO$_3$ (26.2 g, 0.190 moles), 3-isopropoxybenzylchloride (11-10c 8.77 g, 0.0475 moles) and NaI (0.36 g, 0.0024 moles) was added. The solution was heated to 65° C. overnight. The reaction was diluted with water (500 mL) and extracted three times with CHCl$_3$. The combined organics were dried over MgSO$_4$, filtered and concentrated then chromatographed using a series of solvents: 50% Ethyl acetate/Hexanes, then 100% Ethyl acetate, then 10% MeOH/CHCl$_3$ containing 1% TEA to give the product, which was further purified on a Waters automated system affixed with a Chiralpak AD 10 cm×50 cm cartridge eluting at 150 mL/min with isocratic 20% isopropyl alcohol in hexanes with no modifier.

An alternative workup consisted of filtering the cooled reaction through celite and diluting with EtOAc, then washing with aqueous LiCl solution and brine. The organic layers were dried over Na$_2$SO$_4$, then concentrated and pumped on with heat to remove residual DMF. Chromatography on silica eluting with 0-100% EtOAc/Hexanes gave the product, which was purified further as described above.

$^1$H NMR (400 MHz, CDCl$_3$) δ 8.34 (d, J=8.4 Hz, 1H), 7.32 (dd, J=8, 14.6 Hz, 1H), 7.24 (m, 1H), 7.0 (m, 3H), 6.8 (m, 3H), 4.55 (pentet, J=6 Hz, 1H), 4.10 (d, J=12.8 Hz, 1H), 3.95 (m, 1H), 2.92 (d, J=12.8 Hz, 1H), 2.8 (m, 1H), 2.54 (m, 1H), 2.23 (dd, J=7.14 Hz, 1H), 2.1 (m, 3H), 1.9-1.6 (m, 7H), 1.4 (m, 1H), 1.33 (d, J=6 Hz, 6H), 1.26 (d, J=6.3 Hz, 3H), 1.35-1.2 (m, 2H), 1.1 (m, 1H).

LCMS ion fragment=507.11

Step 9: (5R,7S)-4-(cyclohexylamino)-1-(3-fluorophenyl)-8-(3-isopropoxybenzyl)-7-methyl-1,3,8-triazaspiro[4.5]dec-3-en-2-one dihydrochloride (Example 11 HCl salt)

(5R,7S)-4-(cyclohexylamino)-1-(3-fluorophenyl)-8-(3-isopropoxybenzyl)-7-methyl-1,3,8-triazaspiro[4.5]dec-3-en-2-one was dissolved in high quality acetonitrile, cooled to 0° C. and 2.5 equivalents of HCl in diethyl ether were added. The solution was allowed to warm to rt. The solution was then reduced to a powdery solid on the rotovap. The residue was suspended in acetonitrile and evaporated two times to give the desired bis-salt.

$^1$H NMR (400 MHz, CDCl$_3$) δ 11.1 (bs, 1H), 10.23 (bs, 1H), 7.5-7.1 (m, 5H), 6.9 (m, 3H), 4.59 (pentet, J=6 Hz, 1H), 4.53 (bd, J=11 Hz, 1H), 4.32 (bs, 1H), 3.66 (bs, 1H), 3.5-3.2 (m, 3H), 2.97 (bs, 1H), 2.85 (bd, J=15 Hz, 1H), 2.63 (bd, J=15 Hz, 1H), 2.21 (m, 1H), 2.0 (m, 2H), 1.7-1.4 (m, 10H), 1.34 (d, J=6 Hz, 3H), 1.31 (d, J=6 Hz, 3H), 1.28 (m, 1H), 1.19 (m, 1H).

Step 10a: 3-isopropoxybenzaldehyde

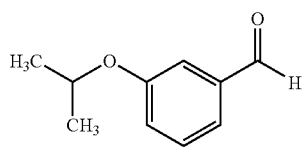

To a 1 molar solution of 3-hydroxybenzaldehyde (10 g, 0.819 moles) in isopropyl alcohol (820 mL) was added 2-iodopropane (146.2 g, 0.860 moles) followed by powdered potassium carbonate (339.5 g, 0.457 moles) and the mixture was heated to reflux under nitrogen for a minimum of 8 hrs. The reaction was complete by TLC. Water was added to the cooled reaction until all salts were dissolved. The mixture was extracted with ether three times. The combined ether extracts were washed with water, 2 M NaOH and again with water until clear (three times) then brine. The organic layer was dried over magnesium sulfate and filtered and evaporated to give the desired product as a pale oil.

$^1$H NMR (400 MHz, CDCl$_3$) δ 9.95 (s, 1H), 7.2 (m, 3H), 7.12 (m, 1H), 4.6 (m, 1H), 1.32 (bs, 6H) ppm.

LCMS ion fragment=164.1

Step 10b: Prep of 3-isopropoxybenzylalcohol

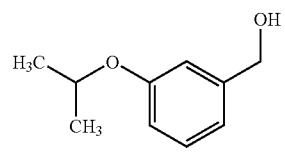

To a 1 molar solution of 3-isopropoxy benzaldehyde (102 g, 0.621 moles) in methanol (620 mL) cooled to 0° was added (slowly) sodium borohydride powder (25.8 g, 0.683 moles)-dissolved in a minimum of methylene chloride and passed through a plug of silica gel washing with more methylene chloride until the silica gel was free of the product. The eluent was stripped to an oil and pumped on high vacuum overnight.

$^1$H NMR (400 MHz, CDCl3) δ 7.25 (m, 1H), 6.9 (bs, 2H), 6.8 (db, J=8 Hz, 1H), 4.65 (d, J=8 Hz, 2H), 4.55 (pentet, J=6 Hz, 1H), 1.7 (m, 1H), 1.34 (d, J=6 Hz, 6H).

LCMS ion fragment=appears as 367.2

Step 10c: Prep of 3-isopropoxybenzylchloride with triphenylphosphine

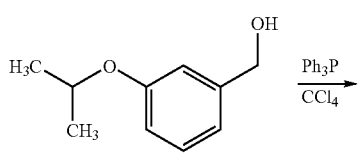

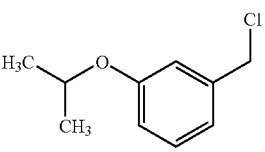

To a stirred solution of the 3-isopropoxybenzylalcohol (19.5 g, 116 mmole) in carbon tetrachloride was added triphenylphosphine (32 g, 122 mmoles) and the mixture was refluxed. The crude reaction was pre-loaded onto silica gel and chromatographed eluting with 10% EtOAc/hexanes to give the product.

$^1$H NMR (400 MHz, CDCl$_3$) δ 7.25 (m, 1H), 6.95 (m, 2H), 6.82 (m, 1H), 4.57 (m, 1H), 4.54 (s, 2H), 1.33 (d, J=6 Hz, 6H).

(LCMS ion fragment=appears as 190.1).

Example 12

(5R,7S)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate and (5S,7R)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate

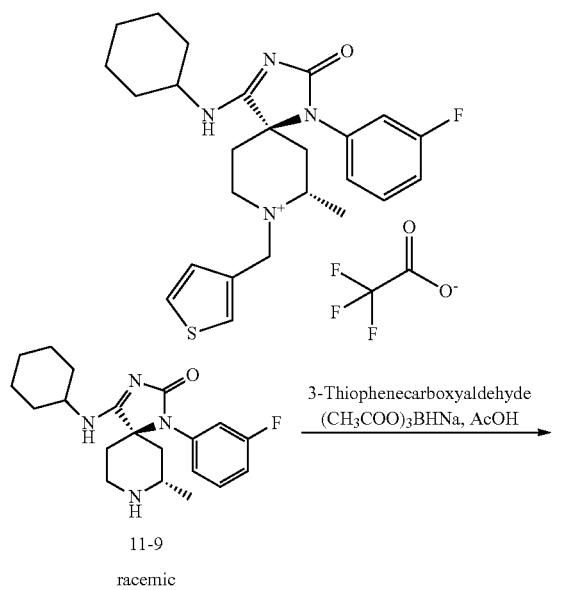

Step 1: (5R,7S)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate and (5S,7R)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate To a stirred solution of (5R,7S)-4-(cyclohexylamino)-1-(3-fluorophenyl)-7-methyl-1,3,8-triazaspiro[4.5]dec-3-en-2-one and (5S,7R)-4-(cyclohexylamino)-1-(3-fluorophenyl)-7-methyl-1,3,8-triazaspiro[4.5]dec-3-en-2-one (prepared as described for Intermediate 11-9 starting with racemic piperidinone 11-3, 50.0 mg, 0.134 mmol), 3-thiophene-carboxaldehyde (0.05 g, 0.42 mmol), and acetic acid (0.01 mL, 0.17 mmol) in 1 mL DCE was added sodium triacetoxyborohydride (90.0 mg, 0.42 mmol). The reaction mixture was stirred at ambient temperature for 16 h, washed with saturated sodium bicarbonate, water, and brine. The reaction solution was dried with $Na_2SO_4$, and concentrated in vaccuo. The crude compound was purified on a Gilson reverse phase preparatory column, to give the desired product.

LRMS (M+1)=455.16

$^1$H NMR (CD$_3$OD) δ 7.50-7.48 (m, 2H), 7.36-7.34 (m, 1H), 7.19-7.13 (m, 3H), 6.96-6.94 (d, 1H), 4.45-4.41 (d, 1H), 4.29-4.25 (d, 1H), 3.74-3.72 (m, 1H), 3.44-3.41 (m, 1H), 2.85-2.51 (m, 6H), 2.03-2.00 (d, 2H), 1.89-1.85 (d, 2H), 1.72-1.68 (d, 1H), 1.59-1.26 (m, 8H).

The compounds in Table 2 were prepared by alkylated intermediate 11-9 or racemic 11-9 (prepared as described for Intermediate 11-9 starting with racemic piperidinone 11-3), with the appropriate commercially available halide in a manner similar to that described for Example 11, or, they were prepared when intermediate 11-9 was reductively alkylated with the appropriate commercially available aldehyde as described for Example 12. The products were purified by normal or reverse phase chromatography to give the free bases or salts. In some cases the salts isolated from chromatography were converted to the free bases with an aqueous workup. They could then be converted to different salts by mixing the free base in an appropriate organic HCl solution, like ethereal HCl, and evaporating to give the product as the solid salt.

TABLE 2

| Ex | Structure | Chemical name | Mass Spec (M + H) |
|---|---|---|---|
| 13 | 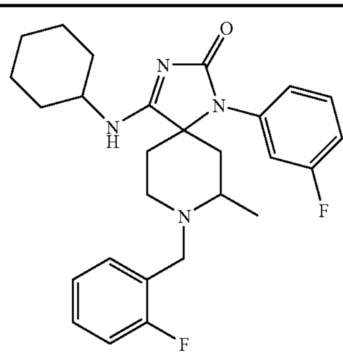 | (5R,7S)-4-(cyclohexylamino)-8-(2-fluorobenzyl)-1-(3-fluorophenyl)-7-methyl-1,3,8-triazaspiro[4.5]dec-3-en-2-one and (5S,7R)-4-(cyclohexylamino)-8-(2-fluorobenzyl)-1-(3-fluorophenyl)-7-methyl-1,3,8-triazaspiro[4.5]dec-3-en-2-one | 467.2 |

TABLE 2-continued

| Ex | Structure | Chemical name | Mass Spec (M + H) |
|---|---|---|---|
| 14 | 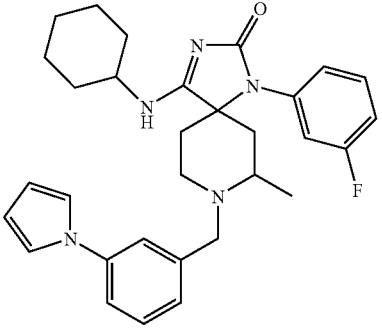 | (5R,7S)-4-(cyclohexylamino)-1-(3-fluorophenyl)-7-methyl-2-oxo-8-[3-(1H-pyrrol-1-yl)benzyl]-1,3-diaza-8-azoniaspiro[4.5]dec-3-ene trifluoro acetate and (5S,7R)-4-(cyclohexyl amino)-1-(3-fluorophenyl)-7-methyl-2-oxo-8-[3-(1H-pyrrol-1-yl)benzyl]-1,3-diaza-8-azoniaspiro[4.5]dec-3-ene trifluoroacetate | 514.3 |
| 15 | 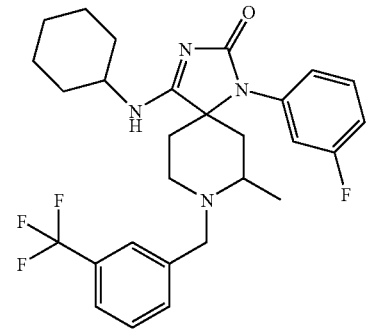 | (5R,7S)-4-(cyclohexylamino)-1-(3-fluorophenyl)-7-methyl-2-oxo-8-[3-(trifluoromethyl)benzyl]-1,3-diaza-8-azoniaspiro[4.5]dec-3-ene trifluoro acetate and (5S,7R)-4-(cyclohexyl amino)-1-(3-fluorophenyl)-7-methyl-2-oxo-8-[3-(trifluoromethyl)benzyl]-1,3-diaza-8-azoniaspiro[4.5]dec-3-ene trifluoroacetate | 517.2 |
| 16 | 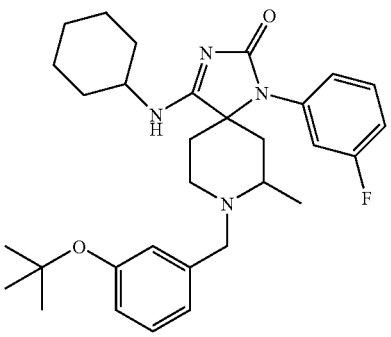 | (5R,7S)-8-(3-tert-butoxybenzyl)-4-(cyclohexylamino)-1-(3-fluorophenyl)-7-methyl-1,3,8-triazaspiro[4.5]dec-3-en-2-one and (5S,7R)-8-(3-tert-butoxybenzyl)-4-(cyclohexylamino)-1-(3-fluorophenyl)-7-methyl-1,3,8-triazaspiro[4.5]dec-3-en-2-one | 521.3 |
| 17 | 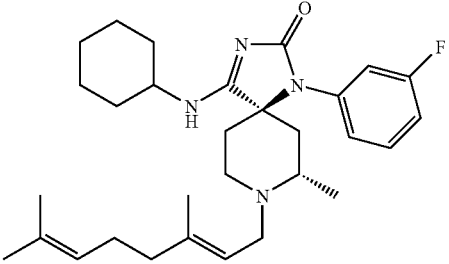 | (5R,7S)-4-(cyclohexylamino)-8-[(2E)-3,7-dimethylocta-2,6-dien-1-yl]-1-(3-fluorophenyl)-7-methyl-1,3,8-triazaspiro[4.5]dec-3-en-2-one | 495.1 |

TABLE 2-continued

| Ex | Structure | Chemical name | Mass Spec (M + H) |
|---|---|---|---|
| 18 | 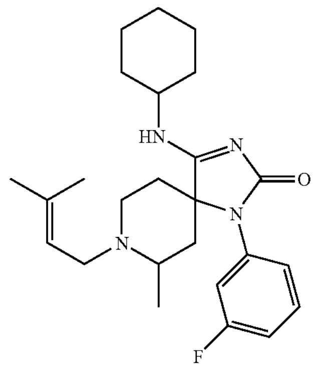 | (5R,7S)-4-(cyclohexylamino)-1-(3-fluorophenyl)-7-methyl-8-(3-methylbut-2-en-1-yl)-2-oxo-1,3-diaza-8-azoniaspiro[4.5]dec-3-ene trifluoroacetate and (5S,7R)-4-(cyclohexylamino)-1-(3-fluorophenyl)-7-methyl-8-(3-methylbut-2-en-1-yl)-2-oxo-1,3-diaza-8-azoniaspiro[4.5]dec-3-ene trifluoroacetate | 427.6 |
| 19 | 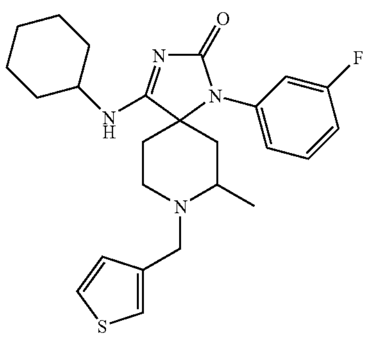 | (5R,7S)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate and (5S,7R)-4-(cyclohexylamino)-1-(3-fluorophenyl)-7-methyl-2-oxo-8-(3-thienylmethyl)-1,3-diaza-8-azoniaspiro[4.5]dec-3-ene trifluoroacetate | 455.1 |
| 20 | 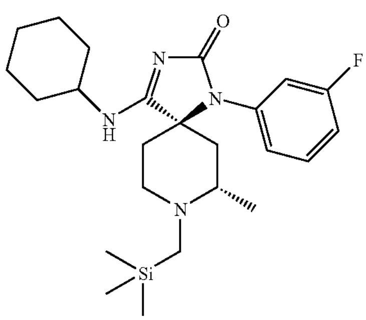 | (5R,7S)-4-(cyclohexylammonio)-1-(3-fluorophenyl)-7-methyl-2-oxo-8-[(trimethylsilyl)methyl]-1,3-diaza-8-azoniaspiro[4.5]dec-3-ene dichloride | 445.0 |
| 21 | 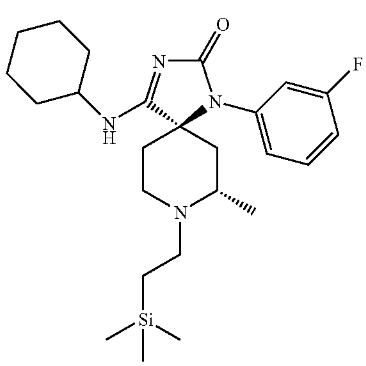 | (5R,7S)-4-(cyclohexylammonio)-1-(3-fluorophenyl)-7-methyl-2-oxo-8-[2-(trimethylsilyl)ethyl]-1,3-diaza-8-azoniaspiro[4.5]dec-3-ene dichloride | 459.0 |

The compounds in Table 3 were prepared by alkylating intermediate 11-9 or racemic 11-9 (prepared as described for Intermediate 11-9 starting with racemic piperidinone 11-3), with the appropriate custom-made halide in a manner similar to that described for Example 11, or, they were prepared when intermediate 11-9 or racemic 11-9 was reductively alkylated with the appropriate custom-made aldehyde as described for Example 12. The products were purified by normal or reverse phase chromatography to give the free bases or salts. In some cases the salts isolated from chromatography were converted to the free bases with an aqueous workup. They could then be converted to different salts by mixing the free base in an appropriate organic acid solution, like ethereal HCl, and evaporating to give the product as the solid salt.

TABLE 3

| Ex | Intermediate | Structure | Chemical name | Mass Spec (M + H) |
|----|--------------|-----------|---------------|-------------------|
| 22 | XII | 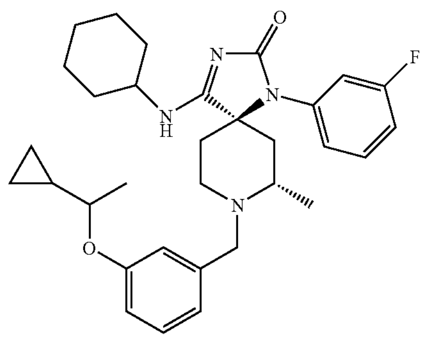 | (5R,7S)-4-(cyclohexylamino)-8-[3-(1-cyclopropylethoxy)benzyl)]-1-(3-fluorophenyl)-7-methyl-1,3,8-triazaspiro[4.5]dec-3-en-2-one | 533.7 |
| 23 | III | 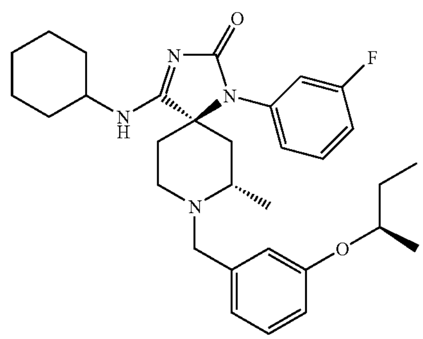 | (5R,7S)-4-(cyclohexylamino)-1-(3-fluorophenyl)-7-methyl-8-(3-{[(1R)-1-methylpropyl]oxy}benzyl)-1,3,8-triazaspiro[4.5]dec-3-en-2-one | 521.2 |
| 24 | IV | 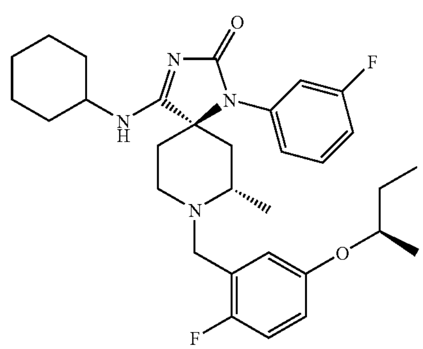 | (5R,7S)-4-(cyclohexylamino)-8-(2-fluoro-5-{[(1R)-1-methylpropyl]oxy}benzyl)-1-(3-fluorophenyl)-7-methyl-1,3,8-triazaspiro[4.5]dec-3-en-2-one | 539.3 |
| 25 | V | 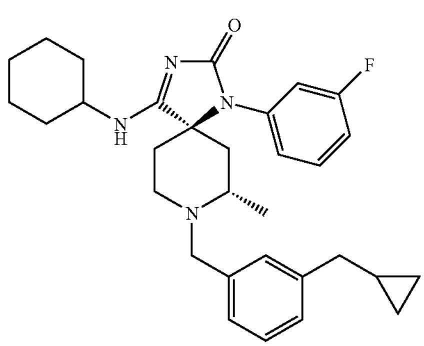 | (5R,7S)-4-(cyclohexylamino)-8-[3-(cyclopropylmethyl)benzyl]-1-(3-fluorophenyl)-7-methyl-1,3,8-triazaspiro[4.5]dec-3-en-2-one | 503.3 |

TABLE 3-continued

| Ex | Intermediate | Structure | Chemical name | Mass Spec (M + H) |
|----|--------------|-----------|---------------|-------------------|
| 26 | VI | 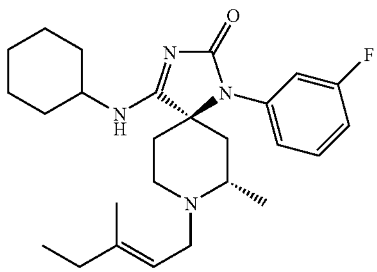 | (5R,7S)-4-(cyclohexylamino)-1-(3-fluorophenyl)-7-methyl-8-[(2E)-3-methylpent-2-en-1-yl]-1,3,8-triazaspiro[4.5]dec-3-en-2-one | 441.0 |
| 27 | XIII | 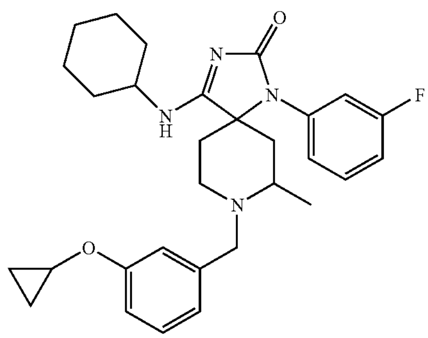 | (5R,7S)-4-(cyclohexylamino)-8-[3-(cyclopropyloxy)benzyl]-1-(3-fluorophenyl)-7-methyl-1,3,8-triazaspiro[4.5]dec-3-en-2-one and (5S,7R)-4-(cyclohexylamino)-8-[3-(cyclopropyloxy)benzyl]-1-(3-fluorophenyl)-7-methyl-1,3,8-triazaspiro[4.5]dec-3-en-2-one | 505.2 |
| 28 | VII | 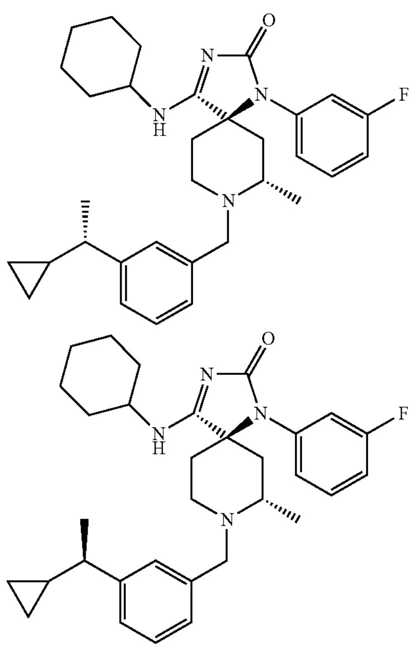 | (5R,7S)-4-(cyclohexylamino)-8-{3-[(1S)-1-cyclopropylethyl]benzyl}-1-(3-fluorophenyl)-7-methyl-2-oxo-1,3-diaza-8-azoniaspiro[4.5]dec-3-ene chloride and (5R,7S)-4-(cyclohexylamino)-8-{3-[(1R)-1-cyclopropylethyl]benzyl}-1-(3-fluorophenyl)-7-methyl-2-oxo-1,3-diaza-8-azoniaspiro[4.5]dec-3-ene chloride | 517.1 |
| 29 | VIII | 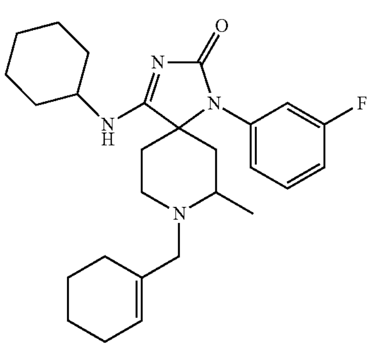 | (5R,7S)-8-(cyclohex-1-en-1-ylmethyl)-4-(cyclohexylamino)-1-(3-fluorophenyl)-7-methyl-1,3,8-triazaspiro[4.5]dec-3-en-2-one and (5S,7R)-8-(cyclohex-1-en-1-ylmethyl)-4-(cyclohexylamino)-1-(3-fluorophenyl)-7-methyl-1,3,8-triazaspiro[4.5]dec-3-en-2-one | 453.3 |

TABLE 3-continued

| Ex | Intermediate | Structure | Chemical name | Mass Spec (M + H) |
|---|---|---|---|---|
| 30 | IX | 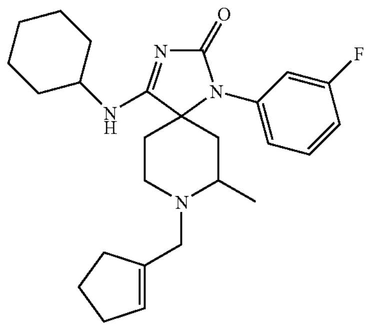 | (5R,7S)-4-(cyclohexylamino)-8-(cyclopent-1-en-1-ylmethyl)-1-(3-fluorophenyl)-7-methyl-2-oxo-1,3-diaza-8-azoniaspiro[4.5]dec-3-ene trifluoroacetate and (5S,7R)-4-(cyclohexylamino)-8-(cyclopent-1-en-1-ylmethyl)-1-(3-fluorophenyl)-7-methyl-2-oxo-1,3-diaza-8-azoniaspiro[4.5]dec-3-ene trifluoroacetate | 439.1 |
| 31 | X | 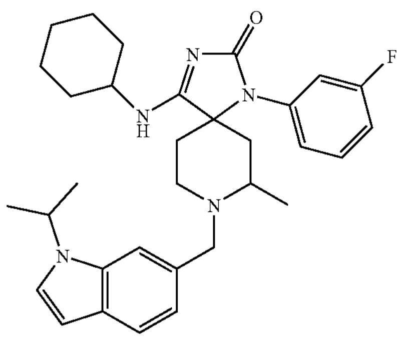 | (5R,7S)-4-(cyclohexylamino)-1-(3-fluorophenyl)-8-[(1-isopropyl-1,3,8-triazaspiro[4.5]dec-3-en-2-one and (5S,7R)-4-(cyclohexylamino)-1-(3-fluorophenyl)-8-[(1-isopropyl-1H-indol-6-yl)methyl]-7-methyl-1,3,8-triazaspiro[4.5]dec-3-en-2-one | 530.10 |
| 32 | XI | 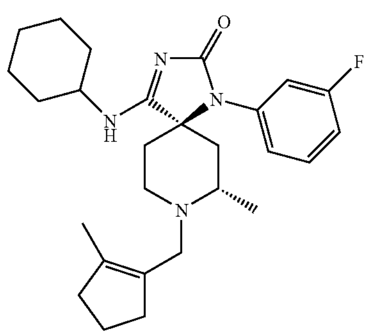 | (5R,7S)-4-(cyclohexylamino)-1-(3-fluorophenyl)-7-methyl-8-[(2-methylcyclopent-1-en-1-yl)methyl]-1,3,8-triazaspiro[4.5]dec-3-en-2-one | 453.24 |

The compounds in Table 4 were prepared in a manner similar to that described for Example 11. Intermediate 11-6 or racemic 11-6 (prepared as described for Intermediate 11-6 starting with racemic piperidinone 11-3), was treated with the appropriate amine in a manner similar to that described for Intermediate 11-8. The amine or amine salt was heated with the resulting iminohydantoin neat or with an appropriate base like N-methylmorpholine as the base/cosolvent and in some instances an additional appropriate solvent like toluene was used. The protecting group was then removed as described for Intermediate 11-9 and the piperidine nitrogen was treated in one of several ways. The piperidine nitrogen was alkylated with the appropriate alkylating agent, either commercially available or prepared as described herein, or acylated with an appropriate acid to form the amide, then reduced as described for Example 47, or reductively aminated as described for Example 12 to give material that was purified either by normal or reverse phase chromatography to give the free bases or salts. In some cases the compounds were further purified using chiral HPLC to give the final compounds. In some cases the salts isolated from chromatography were converted to the free bases with an aqueous workup. They could then be converted to different salts by mixing the free base in an appropriate organic acid solution, like ethereal HCl, and evaporating to give the product as the solid salt.

TABLE 4

| Ex # | Intermediate | Structure | Chemical name | Mass Spec (M + H) |
|---|---|---|---|---|
| 33 | III | 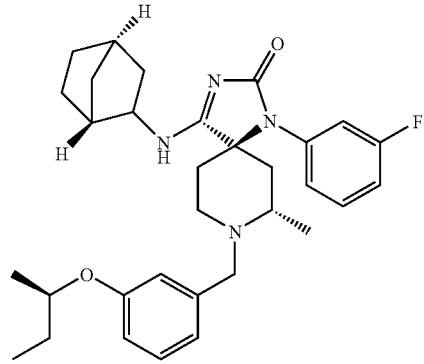 | (5R,7S)-[(1R,4R)-bicyclo[2.2.1]hept-2-ylamino]-1-(3-fluorophenyl)-7-methyl-8-(3-{[(1R)-1-methylpropyl]oxy}benzyl)-1,3,8-triazaspiro[4.5]dec-3-en-2-one and (5R,7S)-4-[(1S,4S)-bicyclo[2.2.1]hept-2-ylamino]-1-(3-fluorophenyl)-7-methyl-8-(3-{[(1R)-1-methylpropyl]oxy}benzyl)-1,3,8-triazaspiro[4.5]dec-3-en-2-one | 533.1 |
| 34 | XVII | 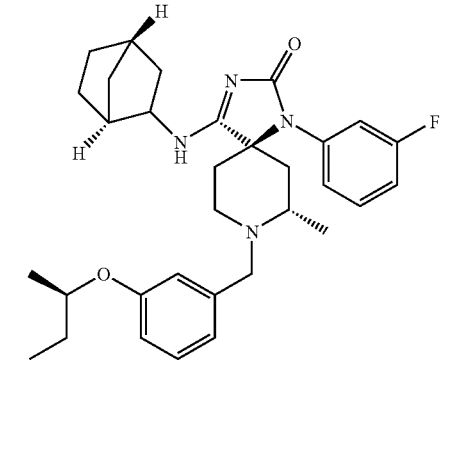 | (5R,7S)-4-(cyclobutylamino)-1-(3-fluorophenyl)-7-methyl-8-(3-{[(1S,2R)-2-methylcyclopropyl]oxy}benzyl)-2-oxo-1,3-diaza-8-azoniaspiro[4.5]dec-3-ene chloride and (5R,7S)-4-(cyclobutylamino)-1-(3-fluorophenyl)-7-methyl-8-(3-{[(1R,2S)-2-methylcyclopropyl]oxy}benzyl)-2-oxo-1,3-diaza-8-azoniaspiro[4.5]dec-3-ene chloride | 491.1 |

TABLE 4-continued

| Ex # | Intermediate | Structure | Chemical name | Mass Spec (M + H) |
|---|---|---|---|---|
| 35 | XXIII | 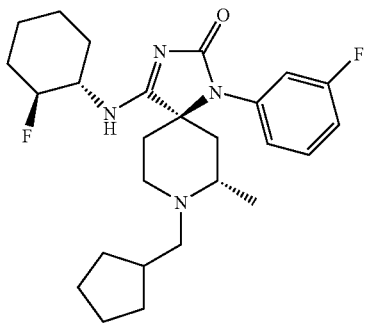 | (5R,7S)-8-(cyclopentylmethyl)-N-[(1S,2S)-2-fluorocyclohexyl]-1-(3-fluorophenyl)-7-methyl-2-oxo-1,3,8-triazaspiro[4.5]dec-3-en-4-aminium chloride and (5R,7S)-8-(cyclopentylmethyl)-N-[(1R,2R)-2-fluorocyclohexyl]-1-(3-fluorophenyl)-7-methyl-2-oxo-1,3,8-triazaspiro[4.5]dec-3-en-4-aminium chloride | 459.0 |
| 36 | Commercially available | 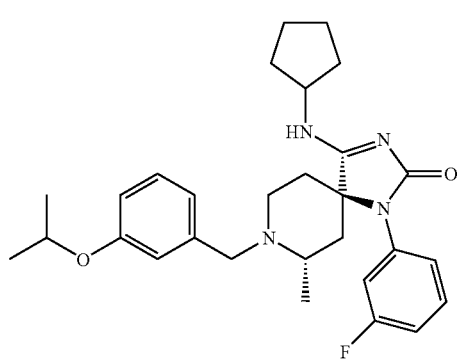 | (5R,7S)-4-(cyclopentylamino)-1-(3-fluorophenyl)-8-(3-isopropoxybenzyl)-7-methyl-2-oxo-1,3-diaza-8-azoniaspiro[4.5]dec-3-ene chloride | 530.1 |
| 37 | XVIII | 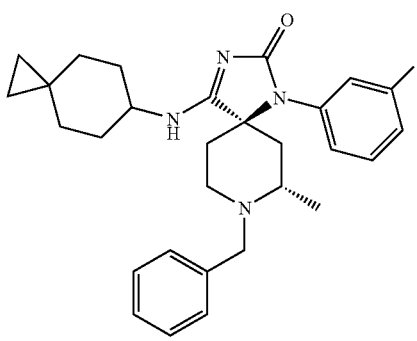 | (5R,7S)-8-benzyl-1-(3-fluorophenyl)-7-methyl-4-(spiro[2.5]oct-6-ylamino)-1,3,8-triazaspiro[4.5]dec-3-en-2-one | 475.6 |

TABLE 4-continued

| Ex # | Intermediate | Structure | Chemical name | Mass Spec (M + H) |
|------|--------------|-----------|---------------|-------------------|
| 38 | XIX | | (5R,7S)-1-(3-fluorophenyl)-8-(3-isopropoxybenzyl)-7-methyl-2-oxo-N-[(5S,6R)-6-phenylspiro[2.4]hept-5-yl]-1,3,8-triazaspiro[4.5]dec-3-en-4-aminium chloride and (5R,7S)-1-(3-fluorophenyl)-8-(3-isopropoxybenzyl)-7-methyl-2-oxo-N-[(5R,6S)-6-phenylspiro[2.4]hept-5-yl]-1,3,8-triazaspiro[4.5]dec-3-en-4-aminium chloride | 596.8 |
| 39 | XXI | 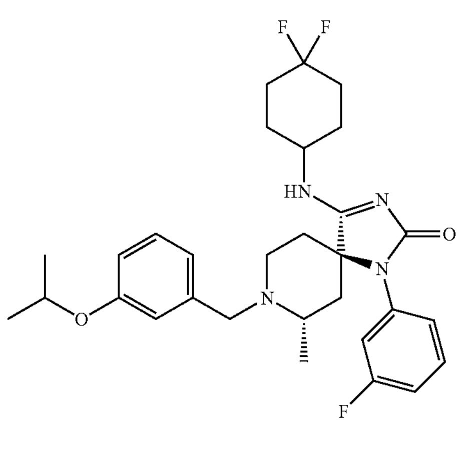 | (5R,7S)-4-[(4,4-difluorocyclohexyl)amino]-1-(3-fluorophenyl)-8-(3-isopropoxybenzyl)-7-methyl-2-oxo-1,3-diaza-8-azoniaspiro[4.5]dec-3-ene chloride | 544.6 |

TABLE 4-continued

| Ex # | Intermediate | Structure | Chemical name | Mass Spec (M + H) |
|---|---|---|---|---|
| 40 | XXI | 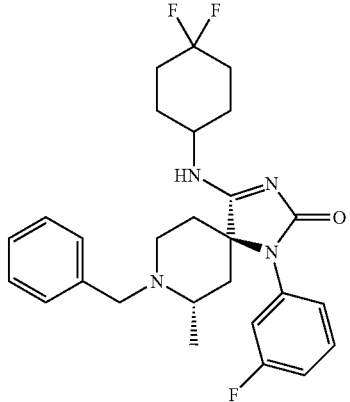 | (5R,7S)-8-benzyl-4-[(4,4-difluorocyclohexyl)amino]-1-(3-fluorophenyl)-7-methyl-2-oxo-1,3-diaza-8-azoniaspiro[4.5]dec-3-ene chloride and (5S,7R)-8-benzyl-difluorocyclohexyl)amino]-1-(3-fluorophenyl)-7-methyl-2-oxo-1,3-diaza-8-azoniaspiro[4.5]dec-3-ene chloride | 486.6 |
| 41 | XX | 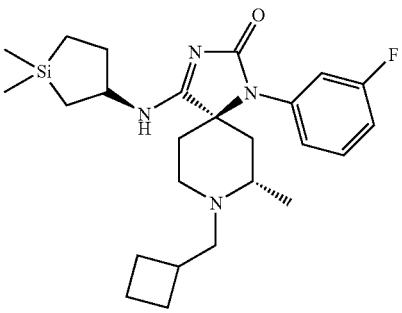 | (5R,7S)-8-(cyclobutylmethyl)-4-{[(3R)-1,1-dimethylsilolan-3-yl]ammonio}-1-(3-fluorophenyl)-7-methyl-2-oxo-1,3-diaza-8-azoniaspiro[4.5]dec-3-ene dichloride and (5R,7S)-8-(cyclobutylmethyl)-yl]ammonio}-1-(3-fluorophenyl)-7-methyl-2-oxo-1,3-diaza-8-azoniaspiro[4.5]dec-3-ene dichloride | 457.1 |

TABLE 4-continued

| Ex # | Intermediate | Structure | Chemical name | Mass Spec (M + H) |
|---|---|---|---|---|
| 42 | Commercially available | | (5R,7S)-N-[(1R)-1,2-dimethylpropyl]-1-(3-fluorophenyl)-7-methyl-8-(3-methylbut-2-en-1-yl)-2-oxo-1,3,8-triazaspiro[4.5]dec-3-en-4-aminium trifluoroacetate and (5R,7S)-N-[(1S)-1,2-dimethylpropyl]-1-(3-fluorophenyl)-7-methyl-8-(3-methylbut-2-en-1-yl)-2-oxo-1,3,8-triazaspiro[4.5]dec-3-en-4-aminium trifluoroacetate | 415 |

Example 43

(5R,7S)-8-(cyclobutylmethyl)-4-{[(1R,2R)-2-fluorocyclohexyl]ammonio}-1-(3-fluorophenyl)-7-methyl-2-oxo-1,3-diaza-8-azoniaspiro[4.5]dec-3-ene dichloride and (5R,7S)-8-(cyclobutylmethyl)-4-{[(1S,2S)-2-fluorocyclohexyl]ammonio}-1-(3-fluorophenyl)-7-methyl-2-oxo-1,3-diaza-8-azoniaspiro[4.5]dec-3-ene dichloride

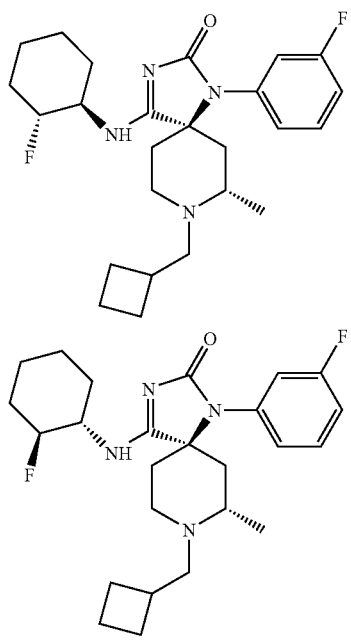

Step 1: Benzyl (5R,7S)-4-{[(1R,2R)-2-fluorocyclohexyl]amino}-1-(3-fluorophenyl)-7-methyl-2-oxo-1,3,8-triazaspiro[4.5]dec-3-en-8-carboxylate and benzyl (5R,7S)-4-{[(1S,2S)-2-fluorocyclohexyl]amino}-1-(3-fluorophenyl)-7-methyl-2-oxo-1,3,8-triazaspiro[4.5]dec-3-en-8-carboxylate

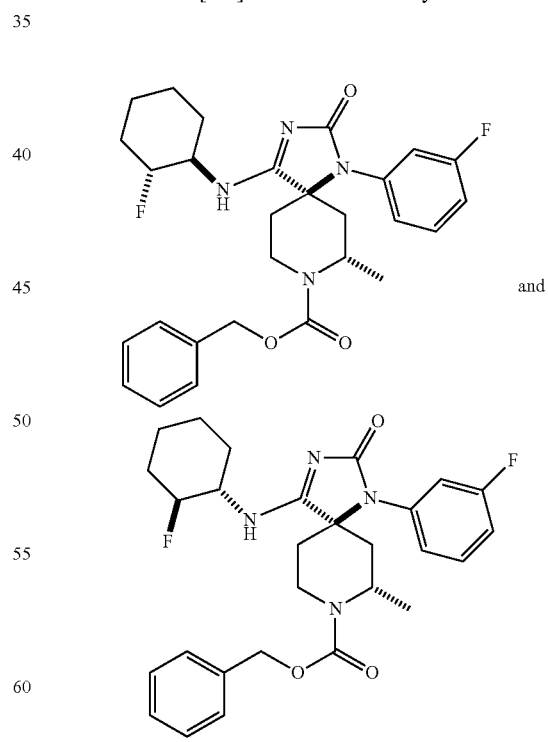

A solution containing 1.60 g (3.90 mmol) of benzyl (5R,7S)-1-(3-fluorophenyl)-4-imino-7-methyl-2-oxo-1,3,8-triazaspiro[4.5]decane-8-carboxylate (Intermediate 11-6) in 6 mL of N-methylmorpholine was treated with 3.09 g (15.6 mmol) of trans-2-fluorocyclohexanaminium bromide (Intermediate XXIII) and the resulting mixture was heated to 120° C. for 48 h in a sealed tube. The reaction was cooled, quenched with 25 mL of 1N HCl and extracted three times with 100 mL of a 9:1 mixture of DCM and MeOH. The combined organic extracts were washed with 50 mL of 1N HCl and 50 mL of brine. The organic phase was dried over MgSO₄, filtered and concentrated. Column chromatography (90:10:1) DCM/MeOH/TEA afforded the desired compound as a sticky tan solid.

LCMS (M+H)=511.4

Step 2: (5R,7S)-4-{[(1R,2R)-2-fluorocyclohexyl]amino}-1-(3-fluorophenyl)-7-methyl-1,3,8-triazaspiro[4.5]dec-3-en-2-one and (5R,7S)-4-{[(1S,2S)-2-fluorocyclohexyl]amino}-1-(3-fluorophenyl)-7-methyl-1,3,8-triazaspiro[4.5]dec-3-en-2-one

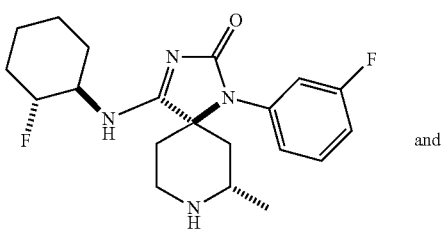

and

Benzyl (5R,7S)-4-{[(1R,2R)-2-fluorocyclohexyl]amino}-1-(3-fluorophenyl)-7-methyl-2-oxo-1,3,8-triazaspiro[4.5]dec-3-en-8-carboxylate and benzyl (5R,7S)-4-{[(1S,2S)-2-fluorocyclohexyl]amino}-1-(3-fluorophenyl)-7-methyl-2-oxo-1,3,8-triazaspiro[4.5]dec-3-en-8-carboxylate (450 mg, 0.88 mmol) was dissolved in 250 mL of MeOH. The solution was degassed and 619 mg of 20% Pd(OH)₂ was added. The reaction was flushed with hydrogen and kept under a hydrogen balloon at rt for 2 h. The flask was evacuated of hydrogen and filtered through Celite. Evaporation of the solvent afforded the desired product as a white solid.

LCMS (M+H)=377.3

Step 3: (5R,7S)-8-(cyclobutylmethyl)-4-{[(1R,2R)-2-fluorocyclohexyl]amino}-1-(3-fluorophenyl)-7-methyl-1,3,8-triazaspiro[4.5]dec-3-en-2-one

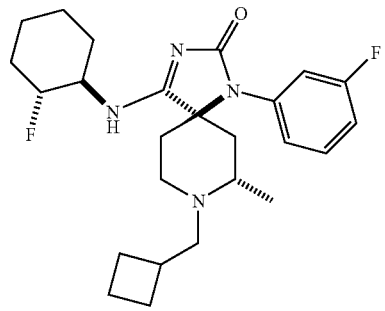

To a solution containing 55 mg (0.15 mmol) of (5R,7S)-4-{[(1R,2R)-2-fluorocyclohexyl]amino}-1-(3-fluorophenyl)-7-methyl-1,3,8-triazaspiro[4.5]dec-3-en-2-one and (5R,7S)-4-{[(1S,2S)-2-fluorocyclohexyl]amino}-1-(3-fluorophenyl)-7-methyl-1,3,8-triazaspiro[4.5]dec-3-en-2-one in DMF (1.5 mL) was added powdered K₂CO₃ (81 mg, 0.58 mmol) and bromomethylcyclobutane (22 mg, 0.15 mmol). The solution was heated to 60° C. overnight. The reaction was diluted with water (1.5 mL) and extracted three times with EtOAc. The combined organics were dried over MgSO₄, filtered and concentrated then chromatographed using 100% EtOAc to give the desired product which was further purified on a Waters automated system affixed with a Chiralpak AD 5 cm×50 cm cartridge eluting at 80 mL/min with isocratic 20% ethyl alcohol in hexanes with no modifier. The second peak was the product. The salt could be formed as described for the examples in Table 5.

¹H NMR (400 MHz, CDCl₃) δ 9.34 (d, J=7.2 Hz, 1H), 7.35 (m, 1H), 7.04 (m, 3H), 4.42 (ddd, J=4.8, 10.4, 50 Hz, 1H), 4.03 (m, 1H), 2.99 (m, 1H), 2.84 (dd, J=7.5, 12.6 Hz, 1H), 2.54 (m, 2H), 2.23 (m, 4H), 2.1 (m, 4H), 1.9-1.6 (m, 8H), 1.4-1.2 (m, 4H), 1.11 (d, J=6.3 Hz, 3H).

LCMS (M+H)=445.4

Step 4: (5R,7S)-8-(cyclobutylmethyl)-4-{[(1S,2S)-2-fluorocyclohexyl]amino}-1-(3-fluorophenyl)-7-methyl-1,3,8-triazaspiro[4.5]dec-3-en-2-one

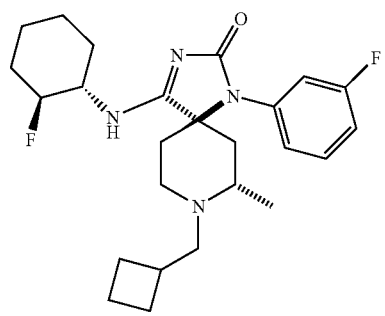

(5R,7S)-8-(cyclobutylmethyl)-4-{[(1S,2S)-2-fluorocyclohexyl]amino}-1-(3-fluorophenyl)-7-methyl-1,3,8-triazaspiro[4.5]dec-3-en-2-one could also be isolated as the first peak from the above chromatography and its salt (5R,7S)-8-(cyclobutylmethyl)-4-{[(1S,2S)-2-fluorocyclohexyl]ammonio}-1-(3-fluorophenyl)-7-methyl-2-oxo-1,3-diaza-8-azoniaspiro[4.5]dec-3-ene dichloride could be prepared as described for the examples in Table 5.

LCMS (M+H)=445.08

The compounds in Table 5 were prepared in a manner similar to that described for Example 11. Intermediate 11-3S underwent the Strecker reaction with the appropriate aniline. The resulting Strecker product was taken through the cyclization and iminohydantoin displacement reactions as described for Example 11. The protecting group was then removed as described for Example 11 and the piperidine nitrogen was treated in one of several ways. The piperidine nitrogen was alkylated with the appropriate alkylating agent, either commercially available or prepared as described herein, or acylated with an appropriate acid to form the amide, then reduced as described for Example 47, or reductively aminated as described for Example 12 to give material that was purified either by normal or reverse phase chromatography to give the free bases or salts. In some cases the compounds were further purified using chiral HPLC to give the final compounds. In some cases the salts isolated from chromatography were converted to the free bases with an aqueous workup. They could then be converted to different salts by mixing the free base in an appropriate organic acid solution, like ethereal HCl, and evaporating to give the product as the solid salt.

Example 46

(5R,7S)-4-(cyclohexylamino)-1-(3-fluorophenyl)-8-(3-isopropoxybenzyl)-7-methyl-1,3,8-triazaspiro[4,5]dec-3-ene-2-thione and (5S,7R)-4-(cyclohexylamino)-1-(3-fluorophenyl)-8-(3-isopropoxybenzyl)-7-methyl-1,3,8-triazaspiro[4,5]dec-3-ene-2-thione

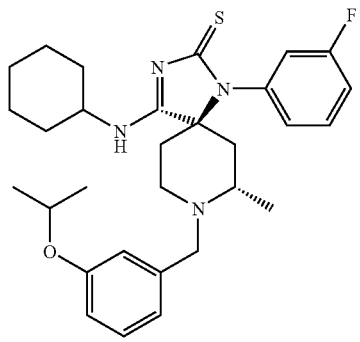

3-Fluoroaniline hydrochloride (4.80 g, 0.033 moles) was added slowly to a suspension of 1-(3-isopropylbenzyl)-2-methylpiperidin-4-one (Intermediate II, 8.10 g, 0.031 moles),

TABLE 5

| Ex # | Aniline | Structure | Chemical name | Mass Spec (M + H) |
|---|---|---|---|---|
| 44 | 3-Chloro | 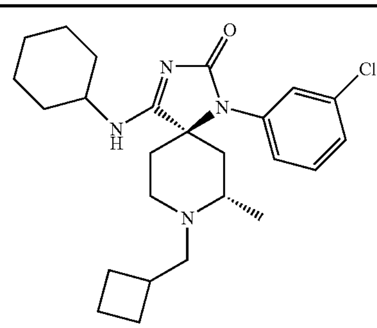 | (5R,7S)-1-(3-chlorophenyl)-8-(cyclobutylmethyl)-N-cyclohexyl-7-methyl-2-oxo-1,3,8-triazaspiro[4.5]dec-3-en-4-aminium chloride | 443.2 |
| 45 | 3-Bromo | | (5R,7S)-1-(3-bromophenyl)-8-(cyclobutylmethyl)-N-cyclohexyl-7-methyl-2-oxo-1,3,8-triazaspiro[4.5]dec-3-en-4-aminium chloride | 487.1 | cyclohexyl isocyanide (3.62 g, 4.11 mL, 0.033 moles), and potassium thiocyanate (3.16 g, 0.033 moles) in methanol (500 mL) at 0° C. The reaction was warmed to rt and additional methanol was added to completely dissolve the starting materials. The reaction was heated to 70° C. and monitored via LCMS for 16 hrs. The reaction was concentrated to give the desired product as a crude oil. The material was purified on silica with 0-50% EtOAc (+1.5% MeOH containing 0.1% NH$_4$OH) in hexanes. The cis isomer eluted first, followed by the desired trans isomer second.

$^1$H NMR (400 MHz, CDCl3) δ 8.1 (d, J=8.1 Hz, 1H), 7.41 (dd, J=8.1, 6.3 Hz, 1H) 7.25 (m, 1H), 7.12 (dt, J=1.8, 8.3 Hz, 1H) 6.96 (d, 3=7.9 Hz, 1H), 6.90 (bd, 1H), 6.84 (bd, 1H), 6.77 (m, 2H), 6.56 (pentet, J=6.1 Hz, 1H), 4.15 (m, 1H), 4.10 (d, J=12.8 Hz, 1H), 2.90 (d, J=12.8 Hz, 1H), 2.83 (m, 1H), 2.53 (m, 1H), 2.18 (d, J=7.5, 14.2 Hz, 1H), 2.10 (m, 2H), 2.0 (m, 1H), 1.9 (m, 2H), 1.8 (bd, 1H), 1.75-1.6 (m, 5H), 1.4 (m, 1H), 1.33 (d, J=6 Hz, 6H), 1.27 (d, J=6.3 Hz, 3H), 1.20 (m, 1H), 1.05 (m, 1H) ppm.

LCMS=523.5 (m+1)

In an alternative preparation the piperidinone is dissolved in 10 volumes of 10% water/methanol and treated with the isonitrile, thiocyanate and aniline. The solution is heated to 60° C. and a solution of 1 equivalent benzenesulfonic acid in methanol is added via syringe pump over 2-3 hrs.

Example 47

Alternative synthesis of (5R,7S)-4-(cyclohexylamino)-1-(3-fluorophenyl)-8-(3-isopropoxybenzyl)-7-methyl-1,3,8-triazaspiro[4.5]dec-3-en-2-one dihydrochloride (Example 11 HCl salt)

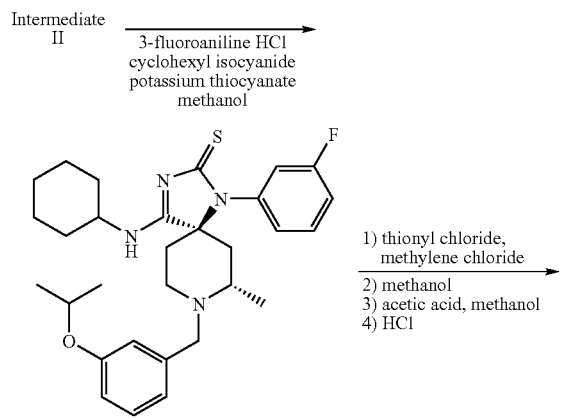

Example 46

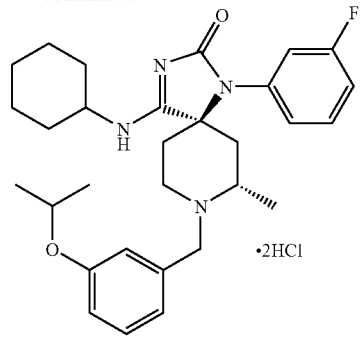

Example 47

(5R,7S)-4-(cyclohexylamino)-1-(3-fluorophenyl)-8-(3-isopropoxybenzyl)-7-methyl-1,3,8-triazaspiro[4.5]dec-3-en-2-one dihydrochloride

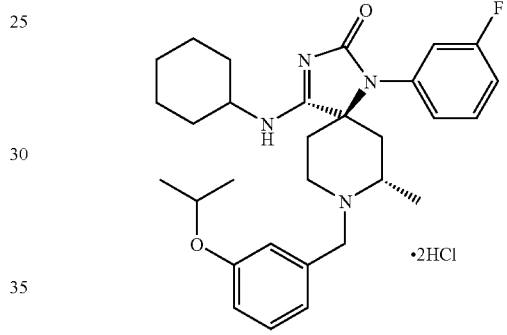

Thionyl chloride (16 mL, 0.22 moles) was added to a solution of 4-(cyclohexylamino)-1-(3-fluorophenyl)-8-(3-isopropoxybenzyl)-7-methyl-1,3,8-triazaspiro[4,5]dec-3-ene-2-thione (Example 46) (7.9 g, 0.015 mole) in chloroform (100 mL). The reaction was heated to reflux for 1 h (at which time an aliquot quenched into MeOH showed no starting material remaining) and then carefully evaporated. The resulting oil was dissolved in ~100 mL CHCl$_3$, placed in an ice-cooled jacketed addition funnel and added dropwise to 250 mL of cold (0° C.) MeOH. The temperature throughout the addition was maintained <10° C. The reaction was stirred for 1 hr at 0° C. at which time LCMS showed no sm or chloride remaining. The reaction was then evaporated to give a brown foam. The foam was dissolved in MeOH (~200 mL) and treated with glacial acetic acid (50 mL), and the reaction was heated to 40° C. Most of the starting material was gone after a short period of time. LCMS after 1 hr of heating showed ~5% sm or other impurity remaining. The reaction was evaporated. The small amount of remaining starting material was consumed upon evaporation. A small portion of the crude material was extracted from CHCl$_3$/aqueous bicarbonate, the organic was dried over Na$_2$SO$_4$ and evaporated to give neutral racemic product for characterization.

$^1$H NMR (400 MHz, CDCl$_3$) δ 8.35 (d, J=7.5 Hz, 1H), 7.33 (dd, J=8.1, 14.6 Hz, 1H), 7.24 (m, 1H), 7.0 (m, 3H), 6.8 (m, 3H), 4.55 (pentet, J=6 Hz, 1H), 4.10 (d, J=12.8 Hz, 1H), 3.96 (m, 1H), 2.93 (d, J=12.5 Hz, 1H), 2.82 (m, 1H), 2.55 (m, 1H), 2.24 (dd, J=7.1, 14.4 Hz, 1H), 2.1 (m, 3H), 1.95-1.6 (m, 7H), 1.4 (m, 1H), 1.34 (d, J=6 Hz, 6H), 1.28 (d, J=6.2 Hz, 3H), 1.35-1.2 (m, 1H), 1.2 (m, 1H), 1.1 (m, 1H).

LCMS ion fragment=507.11

The remaining crude was chromatographed (Biotage Flash, 0-100% EtOAc followed by 5% (2 M NH₃/MeOH)/CHCl₃). Fractions containing the desired product were isolated, then the material was resolved using a Chiralpak AD 110×50 cm column eluted with 20/80 IPA/hexane until the first peak (desired) eluted, then with 50:50 IPA/Hexane to flush off the second undesired isomer. The desired material was dissolved in high quality acetonitrile, cooled to 0° C. and 2.0 equivalents of HCl in diethyl ether were added. The solution was then reduced to a powdery solid on the rotovap. The residue is suspended in acetonitrile and evaporated two times to give the desired bis-salt.

¹H NMR (400 MHz, CDCl₃) δ 8.35 10.9 (bs, 1H), 10.83 (bd, J=8.2 Hz, 1H), 7.5 (m, 1H), 7.43 (m, 1H), 7.3 (bd, J=8.6 Hz, 1H), 7.23 (m, 1H), 7.18 (m, 1H), 6.88 (m, 3H), 4.59 (pentet, J=6 Hz, 1H), 4.5 (bd, J=14.5 Hz, 1H), 4.4 (m, 1H), 3.70 (m, 1H), 3.48 (m, 1H), 3.8-3.65 (m, 2H), 3.05 (m, 1H), 2.92 (bd, J=15 Hz, 1H), 2.67 (bd, J=14.8 Hz, 1H), 2.25 (m, 1H), 2.1-2.0 (m, 3H), 1.7 (m, 2H), 1.64 (d, J=6 Hz, 3H), 1.6-1.4 (m, 5H), 1.33 (d, J=6 Hz, 3H), 1.31 (d, J=6.2 Hz, 3H), 1.29 (m, 1H), 1.18 (m, 1H) ppm.

Example 48

8-{[(5R,7S)-4-(cyclohexylamino)-1-(3-fluorophenyl)-7-methyl-2-oxo-1,3-diaza-8-azoniaspiro[4.5]dec-3-en-8-yl]methyl}-2,2-dimethyl-1,2-dihydroquinolinium dichloride

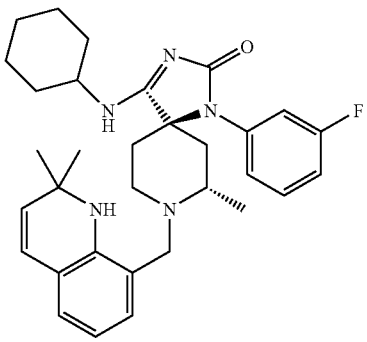

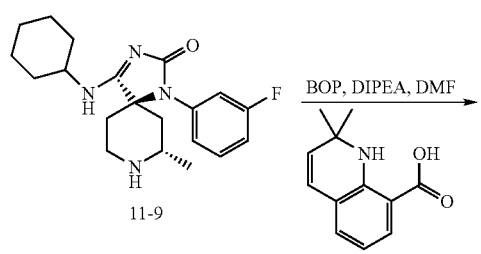

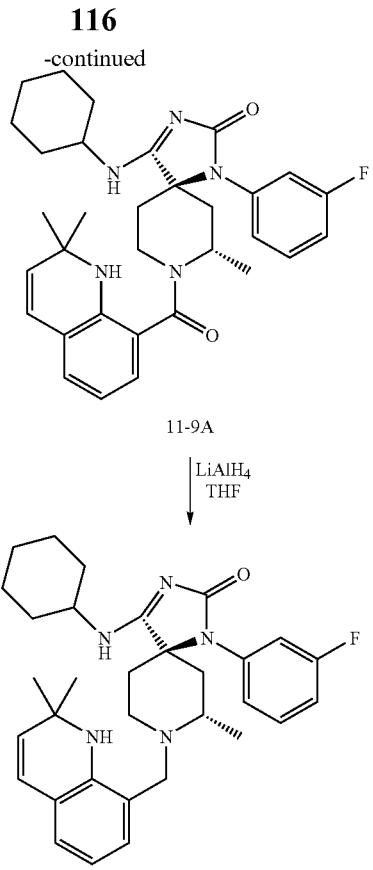

Example 48

Step 1: methyl 2-[(1,1-dimethylprop-2-yn-1-yl)amino]benzoate

To a solution of methyl anthranilate (5.54 g, 36.6 mmol), triethylamine (3.48 g, 34.5 mmol), cuprous chloride (0.21 g, 2.15 mmol), copper powder (0.163 g, 2.56 mmol) in H₂O (4 mL) and THF (14 mL) was added 3-chloro-3-methyl-1-butyne (2.21 g, 21.6 mmol). After heating to 65° C. for 4 h the reaction was cooled, diluted with water and extracted using diethyl ether (three times). The combined organic layers were washed with water, dried using MgSO₄ and concentrated under vacuum. Purification by silica gel chromatography (5% EtOAc/hexanes-10% EtOAc/hexanes) afforded the desired product.

LRMS (M+1)=218.2

Step 2: methyl 2,2-dimethyl-1,2-dihydroquinoline-8-carboxylate

To a solution of methyl 2-[(1,1-dimethylprop-2-yn-1-yl)amino]benzoate (1.5 g, 6.90 mmol) in toluene (30 mL) was added cuprous chloride (0.683 g, 6.90 mmol). After stirring at 100° C. overnight the reaction was concentrated under vacuum. Purification by silica gel chromatography (5% EtOAc/hexanes) afforded the desired product.

Step 3: 2,2-dimethyl-1,2-dihydroquinoline-8-carboxylic acid

To a solution of methyl 2,2-dimethyl-1,2-dihydroquinoline-8-carboxylate (0.188 g, 0.865 mmol) in THF (5 mL) and H₂O (5 mL) was added a 1N aqueous solution of sodium hydroxide (3.46 mL, 3.46 mmol). After stirring at 60° C. overnight the reaction mixture was acidified to pH 2 using 1N aqueous HCl, extracted with ethyl acetate (three times), dried over MgSO$_4$ and concentrated under vacuum to afford the desired compound that was used without further purification.

$^1$H NMR (CDCl$_3$) δ 7.73 (d, J=8.2 Hz, 1H), 6.98 (d, J=7.1 Hz, 1H), 6.46 (t, J=7.6 Hz, 1H), 6.24 (d, J=9.7 Hz, 1H), 1.39 (s, 6H).

LRMS (M+1)=204.0

Step 4: (5R,7S)-4-(cyclohexylamino)-8-[(2,2-dimethyl-1,2-dihydroquinolin-8-yl)carbonyl]-1-(3-fluorophenyl)-7-methyl-1,3,8-triazaspiro[4.5]dec-3-en-2-one To a solution of 11-9 (0.309 g, 0.861 mmol) in DMF (10 mL) was added: 2,2-dimethyl-1,2-dihydroquinoline-8-carboxylic acid (0.175 g, 0.861 mmol), diisopropyethylamine (0.334 g, 2.58 mmol) and BOP reagent (0.381 g, 0.861 mmol). After stirring at 50° C. overnight the reaction mixture was diluted with water and extracted using chloroform (three times). The combined organic layer were dried over MgSO$_4$ and concentrated under vacuum. Purification by silica gel chromatography (4% methanol/chloroform/1% triethylamine) afforded the desired product.

LRMS (M+1)=544.1

Step 5: 8-{[(5R,7S)-4-(cyclohexylamino)-1-(3-fluorophenyl)-7-methyl-2-oxo-1,3-diaza-8-azoniaspiro [4.5]dec-3-en-8-yl]methyl}-2,2-dimethyl-1,2-dihydroquinolinium dichloride To a solution of (5R,7S)-4-(cyclohexylamino)-8-[(2,2-dimethyl-1,2-dihydroquinolin-8-yl)carbonyl]-1-(3-fluorophenyl)-7-methyl-1,3,8-triazaspiro[4.5]dec-3-en-2-one (0.468 g, 0.861 mmol) in THF (20 mL) was added-lithium aluminum hydride (1.0 M in THF, 4.30 mL, 4.30 mmol). After stirring at rt for 15 min the reaction was quenched sequentially with H$_2$O (2 mL), 1N NaOH (2 mL) and H$_2$O (6 mL) and then extracted with methylene chloride (three times). The organic layers were dried over MgSO$_4$ and concentrated under vacuum. Purification by reverse phase HPLC afforded the desired compound. The free base was obtained after aqueous workup with aqueous base and an organic solvent like chloroform and the HCl salt was prepare by mixing the free base with ethereal HCl and evaporating to give the product as a solid.

$^1$H NMR (CDCl$_3$): δ 7.38 (d, J=8.0 Hz, 1H), 7.09 (t, J=8.3 Hz, 1H), 7.04 (d, J=7.9 Hz, 1H), 6.98 (d, J=9.5 Hz, 1H), 6.82 (d, J=7.4 Hz, 1H), 6.73 (d, J=7.4 Hz, 1H), 6.49 (t, J=7.4 Hz, 1H), 6.27 (d, J=8.0 Hz, 1H), 5.87 (d, J=8.0 Hz, 1H), 5.21 (s, 1H), 4.05 (d, J=12 Hz, 1H), 3.93 (m, 1H), 2.72 (m, 1H), 2.63 (d, J=12 Hz, 1H), 2.86 (m, 1H), 2.17-1.11 (m, 15H), 1.35 (s, 3H), 1.29 (s, 3H), 1.21 (d, J=6.0 Hz, 3H).

LRMS (M+1)=530.1

Example 49 was prepared in a manner similar to that described for Example 48, using intermediate XIV (2,2-dimethyl-1,2,3,4-tetrahydroquinoline-8-carboxylic acid) described above in the amide formation step.

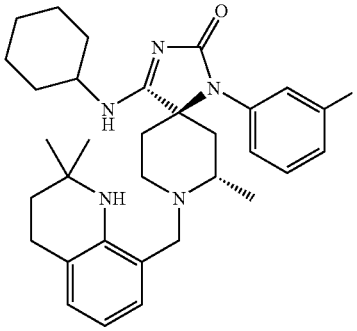

| Ex | Intermediate | Structure | Chemical name | Mass Spec (M + H) |
|---|---|---|---|---|
| 49 | XIV | 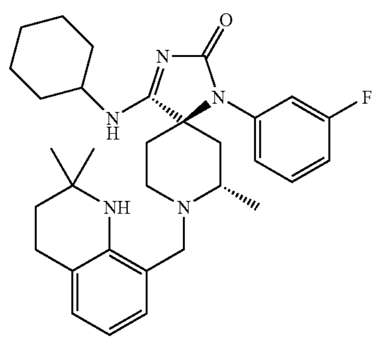 | 8-{[(5R,7S)-4-(cyclohexylamino)-1-(3-fluorophenyl)-7-methyl-2-oxo-1,3-diaza-8-oniaspiro[4.5]dec-3-en-8-yl]methyl}-2,2-dimethyl-1,2,3,4-tetrahydroquinolinium dichloride | 532.1 |

Example 50

(5R,7R)-4-(cyclohexylamino)-1-(3-fluorophenyl)-8-(3-isopropoxybenzyl)-7-vinyl-1,3,8-triazaspiro[4.5] dec-3-en-2-one

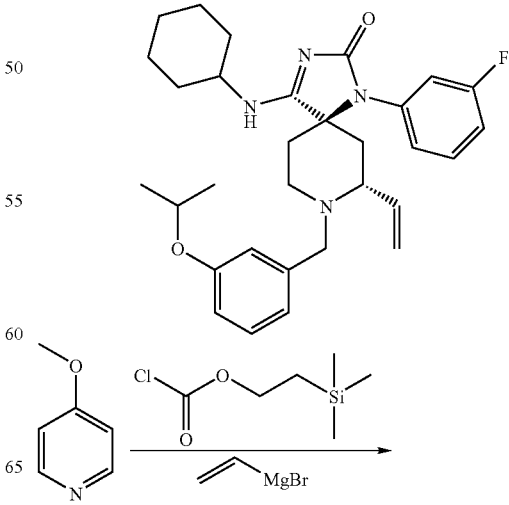

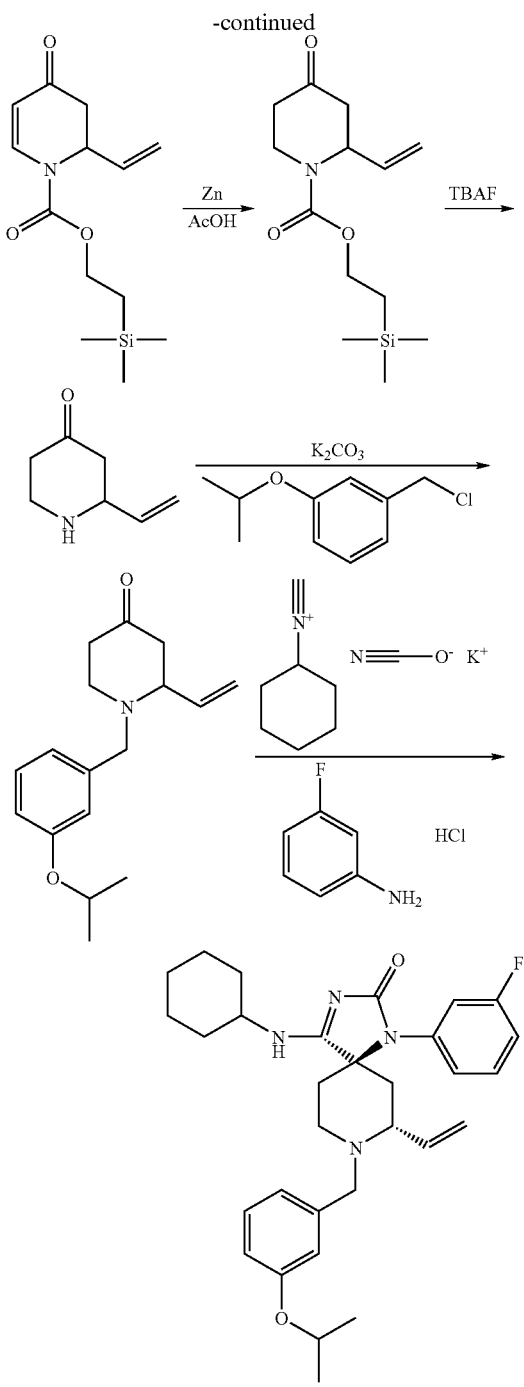

Step 1: 2-(trimethylsilyl)ethyl 4-oxo-2-vinyl-3,4-dihydropyridine-1(2H)-carboxylate 4-Methoxypyridine (17.7 ml, 174 mmol) was dissolved in tetrahydrofuran (500 ml) and cooled to −30° C. Vinylmagnesium bromide (174 ml, 174 mmol) was added dropwise followed by the addition of 2-(trimethylsilyl)ethyl chloridocarbonate (31.5 g, 174 mmol). The solution was stirred for 30 min at −30° C. and quenched with 1N HCl. The resulting solution was extracted three times with diethyl ether. The combined organic fractions were combined, dried with $Na_2SO_4$, and concentrated. The residue was purified by column chromatography on silica gel Biotage 65i, eluting with 30% ethyl acetate/hexanes to give a yellow liquid.

Step 2: 2-(trimethylsilyl)ethyl 4-oxo-2-vinylpiperidine-1-carboxylate 2-(trimethylsilyl)ethyl 4-oxo-2-vinyl-3,4-dihydropyridine-1(2H)-carboxylate (29.1 g, 109 mmol) in acetic acid (500 ml) was added zinc dust (42.7 g, 652 mmol). The solution stirred at room temperature for 2 hrs and was filtered through a pad of celite. The solvent was evaporated under reduced pressure and the product was purified by column chromatography on silica gel Biotage 65i, eluting with 20% ethyl acetate/hexanes.

Step 3: 2-vinylpiperidin-4-one 2-(trimethylsilyl)ethyl 4-oxo-2-vinylpiperidine-1-carboxylate (24.1 g, 89.0 mmol) was dissolved in tetrahydrofuran (90 ml) at 0° C. and added TBAF (268 ml, 268 mmol) dropwise. The solution stirred at 0° C. for 30 min then at rt for an additional three hrs. The solution was quenched with 1N HCl and extracted five times with EtOAc. The organic fractions were combined, dried with $Na_2SO_4$, and concentrated. The crude product was not purified.

Step 4: 1-(3-isopropoxybenzyl)-2-vinylpiperidin-4-one 2-vinylpiperidin-4-one (4.85 g, 38.7 mmol) in acetonitrile (40 ml) was added 1-(chloromethyl)-3-isopropoxybenzene (7.16 g, 38.7 mmol) and finely ground $K_2CO_3$ (16.1 g, 116 mmol). The mixture was stirred at 60° C. for 12 hrs. The solution was filtered, and the solvent was evaporated under reduced pressure. The residue was purified by column chromatography on silica gel Biotage 65i, eluting with 15% ethyl acetate/hexanes.

Step 5: (5R,7R)-4-(cyclohexylamino)-1-(3-fluorophenyl)-8-(3-isopropoxybenzyl)-7-vinyl-1,3,8-triazaspiro[4.5]dec-3-en-2-one 1-(3-isopropoxybenzyl)-2-vinylpiperidin-4-one (7.00 g, 25.6 mmol) in methanol (14 ml) was added cyclohexyl isocyanide (3.17 ml, 25.6 mmol) then potassium cyanate (2.08 g, 25.6 mmol) in water (5 ml) was added. 3-Fluoroaniline hydrochloride (3.78 g, 25.6 mmol) was then added at 0° C. The mixture was stirred at rt for 12 hrs. The reaction was incomplete and another half equivalent of cyclohexyl isocyanide (1.59 ml, 12.8 mmol), potassium cyanate (1.04 g, 12.8 mmol), and 3-fluoroaniline hydrochloride (1.89 g, 12.8 mmol) was added. The mixture stirred for an additional twelve hours. The solution was concentrated and purified on silica gel 7% methanol/chloroform with 0.1% triethylamine. The impure product was purified a second time by flash chromatography on silica gel starting with 50% ethyl acetate/hexanes to 100% ethyl acetate. The diastereomers were resolved on a Chiral AD column 10% ethanol/hexanes with 0.3% diethylamine 250 ml/min at 250 nm.

$^1$H NMR (CDCl$_3$): δ 8.13 (d, J=8.0 Hz, 1H), 7.38-7.32 (m, 1H), 7.26-7.20 (m, 1H), 7.05-6.96 (m, 3H), 6.81-6.75 (m, 3H), 5.87-5.78 (m, 1H), 5.23-5.16 (m, 2H), 4.57-4.51 (m, 1H), 4.06 (d, J=13 Hz, 1H), 3.99-3.95 (m, 1H), 2.96-2.74 (m, 3H), 2.28-2.22 (m, 1H), 2.13-2.03 (m, 3H), 1.98-1.88 (m, 2H), 1.85-1.79 (m, 2H), 1.76-1.65 (m, 2H), 1.42-1.09 (m, 11H).
LRMS=519

The compounds in table 6 were prepared in a manner similar to that described for Example 50 using the appropriate Grignard reagent in the piperidinone formation and using the appropriate benzyl halide in the alkylation step. The products were purified by normal or reverse phase chromatography to give the free bases or salts. The diastereomers were resolved via chiral chromatography. In some cases the salts isolated from chromatography were converted to the free bases with an aqueous workup. They could then be converted to different salts by mixing the free base in an appropriate organic acid solution, like ethereal HCl, and evaporating to give the product as the solid salt.

TABLE 6

| Ex # | Structure | Chemical name | Mass Spec (M + H) |
|---|---|---|---|
| 51 | 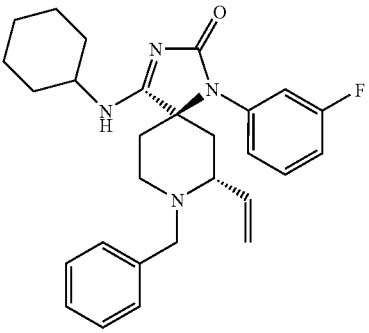 | (5R,7R)-8-benzyl-4-(cyclohexylamino)-1-(3-fluorophenyl)-7-vinyl-1,3,8-triazaspiro[4.5]dec-3-en-2-one | 461 |
| 52 | 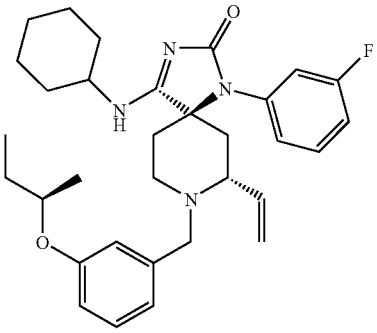 | (5R,7R)-4-(cyclohexylamino)-1-(3-fluorophenyl)-8-(3-{[(1R)-1-methylpropyl]oxy}benzyl)-7-vinyl-1,3,8-triazaspiro[4.5]dec-3-en-2-one | 533 |
| 53 | 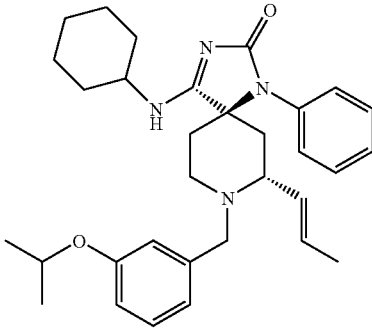 | (5R,7R)-4-(cyclohexylamino)-1-(3-fluorophenyl)-8-(3-isopropoxybenzyl)-7-[(1E)-prop-1-en-1-yl]-1,3,8-triazaspiro[4.5]dec-3-en-2-one | 532.7 |
| 54 | 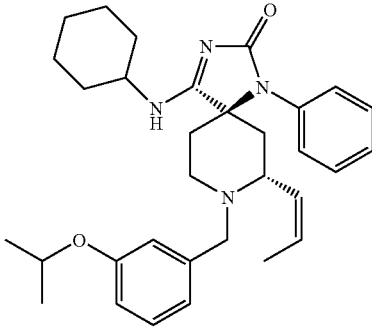 | (5R,7R)-4-(cyclohexylamino)-1-(3-fluorophenyl)-8-(3-isopropoxybenzyl)-7-[(1Z)-prop-1-en-1-yl]-1,3,8-triazaspiro[4.5]dec-3-en-2-one | 532.1 |

Example 55

(5R,7S)-1-(3-fluorophenyl)-7-methyl-4-(methylammonio)-8-[(2'-methylbiphenyl-3-yl)methyl]-2-oxo-1,3-diaza-8-azoniaspiro[4.5]dec-3-ene dichloride

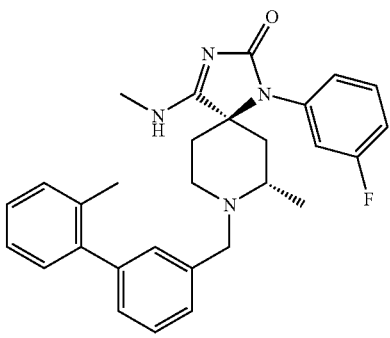

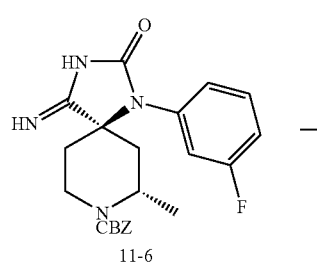

11-6

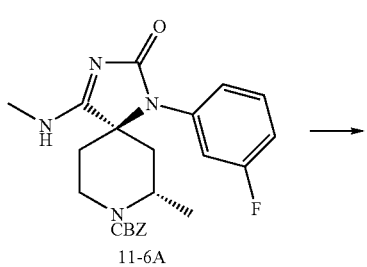

11-6A

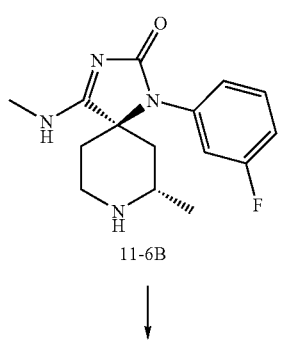

11-6B

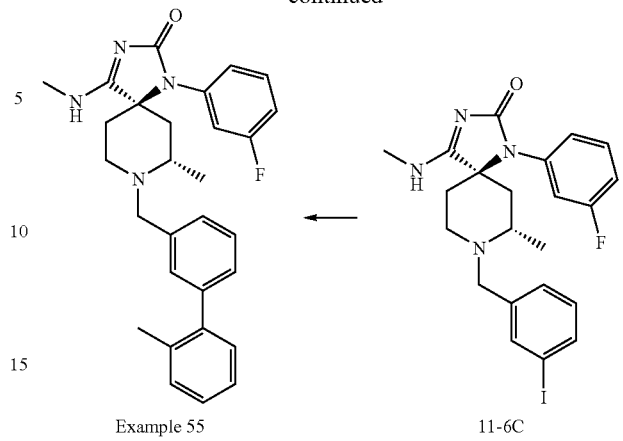

Example 55          11-6C

Step 1: Benzyl (5R,7S)-1-(3-fluorophenyl)-7-methyl-4-(methylamino)-2-oxo-1,3,8-triazaspiro[4.5]dec-3-ene-8-carboxylate To a flask containing benzyl (5R,7S)-4-amino-1-(3-fluorophenyl)-7-methyl-2-oxo-1,3,8-triazaspiro[4.5]dec-3-ene-8-carboxylate (343 mg, 0.86 mmol; Intermediate 11-6) was added methylamine (2.0 M THF, 4.3 mL, 8.6 mmol). The vessel was sealed and placed in a 70° C. oil bath and stirred overnight. The reaction was diluted with aqueous NaHCO₃ and extracted with EtOAc (three times). The combined organic layers were washed with brine, isolated and subsequently dried over Na₂SO₄. Evaporation of solvent and further drying under vacuum gave crude product that was used in the next step.

LCMS [M+H]=411.2

Step 2: (5R,7S)-1-(3-fluorophenyl)-7-methyl-4-(methylamino)-1,3,8-triazaspiro[4.5]dec-3-en-2-one (11-6A)

The product from step 1 above, benzyl (5R,7S)-1-(3-fluorophenyl)-7-methyl-4-(methylamino)-2-oxo-1,3,8-triazaspiro[4.5]dec-3-ene-8-carboxylate (370 mg, 0.86 mmol) was dissolved in 8 mL MeOH. The solvent was degassed with a nitrogen flow for 10 min and Pd(OH)₂ (30 mg, 20% wt. Pd) added. The mixture was purged with a hydrogen balloon for 10 min and then maintained under atmospheric hydrogen at rt overnight with stirring. The reaction was then filtered over Celite, the cake rinsed with EtOAc and the filtrate concentrated to dryness under reduced pressure to give after drying under vacuum the product as a white solid.

LCMS [M+H]=291.2

Step 3: (5R,7S)-1-(3-fluorophenyl)-8-(3-iodobenzyl)-7-methyl-4-(methylamino)-1,3,8-triazaspiro[4.5]dec-3-en-2-one (5R,7S)-1-(3-fluorophenyl)-7-methyl-4-(methylamino)-1,3,8-triazaspiro[4.5]dec-3-en-2-one (250 mg, 0.86 mmol) from step 2 above was dissolved in DMSO (8.0 mL). The flask was charged with K₂CO₃ (594 mg, 4.30 mmol) and 3-iodo-benzylbromide (255 mg, 0.86 mmol). The mixture was then sealed with a septum and placed in 50° C. oil bath and allowed to stir overnight. The mixture was diluted with water and extracted with EtOAc (three times). The combined organic layers were washed with aqueous LiCl (three times), followed by brine and then dried over Na₂SO₄. Solvent removal under reduced pressure gave crude product. Purification over silica via automated flash chromatography (0 to 20% MeOH/CH₂Cl₂ over 20 min.) gave after solvent removal the product as a white solid: LCMS [M+H]=507.3

Step 4: (5R,7S)-1-(3-fluorophenyl)-7-methyl-4-(methylammonio)-8-[(2'-methylbiphenyl-3-yl)methyl]-2-oxo-1,3-diaza-8-azoniaspiro[4.5]dec-3-ene dichloride (Example 54)

A Biotage microwave vial was charged with intermediate (5R,7S)-1-(3-fluorophenyl)-8-(3-iodobenzyl)-7-methyl-4-(methylamino)-1,3,8-triazaspiro[4.5]dec-3-en-2-one (60 mg, 0.118 mmol) from step 3 above, PdCl₂dppf (4.3 mg, 0.01 mmol) and 2-tolylboronic acid (21 mg, 0.15 mmol). The vial was sealed and put under a nitrogen atmosphere. To the solids was added aqueous 1.5M K₂CO₃ (0.24 mL, 0.35 mmol) and degassed THF (0.7 mL). The mixture was briefly vortexed and heated in an Optimizer microwave for 5 min. at 120° C. The reaction enclosure was removed and the reaction diluted with EtOAc and water. The organic layer was washed with brine, dried over Na₂SO₄ and the solvent removed under reduce pressure. Purification over silica via automated flash chromatography (0 to 10% MeOH/CH₂Cl₂) afforded, after solvent removal under reduced pressure, the product as a white solid. The salt was prepared by mixing the free base with ethereal HCl and evaporating to give the product as a solid.
LCMS [M+H]=471.2

Example 56

(5R,7S)-8-(cyclobutylmethyl)-N-cyclohexyl-1-[4'-(isopropylsulfonyl)biphenyl-2-yl]-7-methyl-2-oxo-1,3,8-triazaspiro[4.5]dec-3-en-4-aminium chloride and (5S,7R)-8-(cyclobutylmethyl)-N-cyclohexyl-1-[4'-(isopropylsulfonyl)biphenyl-2-yl]-7-methyl-2-oxo-1,3,8-triazaspiro[4.5]dec-3-en-4-aminium chloride

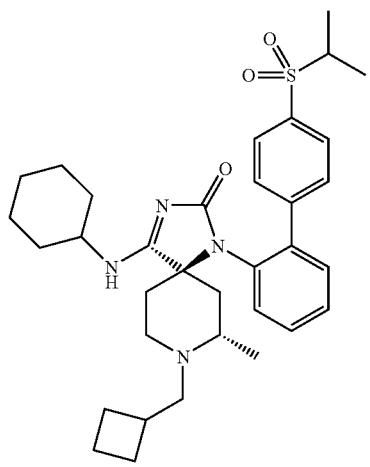

Step 1: 4'-(isopropylsulfonyl)biphenyl-2-amine

To a solution of 2-bromoaniline (1.51 g, 8.78 mmol) in a mixture of benzene (58 mL), H₂O (23 mL) and ethanol (3 mL) was added 4-(isopropylsulfonylphenyl)boronic acid (3.00 g, 13.2 mmol) followed by tetrakis(triphenylphoshine) palladium(0) (1.01 g, 0.88 mmol). After stirring 85° C. for 48 h the reaction mixture was poured into H₂O (500 mL), extracted with chloroform (three times), dried over MgSO₄ and concentrated under vacuum. Purification by silica gel chromatography (20% EtOAc/hexanes—40% EtOAc/hexanes) afforded the desired product.
LRMS (M+1)=276.0

Step 2: benzyl 4-cyano-4-{[4'-(isopropylsulfonyl)biphenyl-2-yl]amino}-2-methylpiperidine-1-carboxylate To a solution of benzyl 2-methyl-4-oxopiperidine-1-carboxylate (1.97 g, 7.95 mmol) and 4'-(isopropylsulfonyl)biphenyl-2-amine (2.19 g, 7.95 mmol) in acetic acid (25 mL) was added trimethylsilyl cyanide (0.79 g, 7.95 mmol). After stirring the reaction at rt overnight the reaction was poured into an icy solution of ammonium hydroxide (30 mL). The solution was extracted with chloroform (three times), dried over MgSO₄ and concentrated under vacuum. Purification by silica gel chromatography afforded the desired product. To enhance the cis/trans product ratio the isolated material was dissolve in methanol (20 mL) and trimethylsilyl cyanide (3.18 g, 23.9 mmol) was added. After stirring the reaction at 70° C. overnight the reaction was concentrated under vacuum. Purification by silica gel chromatography afforded the desired product.
LRMS (M+1)=532.1

Step 3: benzyl (5R,7S)-4-amino-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-amino-1-[4'-(isopropylsulfonyl)biphenyl-2-yl]-7-methyl-2-oxo-1,3,8-triazaspiro[4.5]dec-3-ene-8-carboxylate To a solution of benzyl 4-cyano-4-{[4'-(isopropylsulfonyl)biphenyl-2-yl]amino}-2-methylpiperidine-1-carboxylate (4.23 g, 7.96 mmol) in methylene chloride (75 mL) was added trichloroacetyl isocyanate (1.95 g, 10.34 mmol). After stirring the reaction mixture for 4 h at 65° C. the reaction was cooled and a solution of diisopropylamine (1.34 g, 10.34 mmol) in H₂O (10 mL) and methanol (15 mL) was added. After stirring at 65° C. for 2 h the reaction mixture was cooled and washed with brine (once), dried over MgSO₄ and concentrated under vacuum. Purification by silica gel chromatography (5% methanol/chloroform/1% triethylamine-15% methanol/chloroform/1 triethylamine) afforded the desired product
LRMS (M+1)=575.0

Step 4: benzyl (5R,7S)-4-[(tert-butoxycarbonyl)amino]-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-[(tert-butoxycarbonyl)amino]-1-[4'-(isopropylsulfonyl)biphenyl-2-yl]-7-methyl-2-oxo-1,3,8-triazaspiro[4.5]dec-3-ene-8-carboxylate To a solution of benzyl (5R,7S)-4-amino-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-amino-1-[4'-(isopropylsulfonyl)biphenyl-2-yl]-7-methyl-2-oxo-1,3,8-triazaspiro[4.5]dec-3-ene-8-carboxylate (2.09 g, 3.64 mmol) in THF (50 mL) was added BOC-anhydride (0.952 g, 4.36 mmol). After stirring at 70° overnight the reaction was concentrated under vacuum. Purification by silica gel chromatography (4% methanol/chloroform/1% triethylamine) afforded the desired product.
LRMS (M+1)=675.1

Step 5: benzyl (5R,7S)-4-(cyclohexylamino)-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-(cyclohexylamino)-1-[4'-(isopropylsulfonyl)biphenyl-2-yl]-7-methyl-2-oxo-1,3,8-triazaspiro[4.5]dec-3-ene-8-carboxylate To a solution of benzyl (5R,7S)-4-[(tert-butoxycarbonyl)amino]-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-[(tert-butoxycarbonyl)amino]-1-[4'-(isopropylsulfonyl)biphenyl-2-yl]-7-methyl-2-oxo-1,3,8-triazaspiro[4.5]dec-3-ene-8-carboxylate (1.97 g, 2.92 mmol) in toluene (20 ml) was added cyclohexylamine (2.03 g, 20.4 mmol). After stirring at 110° C. overnight the reaction mixture was diluted with chloroform, washed with 1N aqueous HCl (three times), dried over MgSO$_4$ and concentrated under vacuum to afford the desired product.

LRMS (M+1)=657.4

Step 6: (5R,7S)-4-(cyclohexylamino)-1-[4'-(isopropylsulfonyl)biphenyl-2-yl]-7-methyl-1,3,8-triazaspiro[4.5]dec-3-en-2-one and (5S,7R)-4-(cyclohexylamino)-1-[4'-(isopropylsulfonyl)biphenyl-2-yl]-7-methyl-1,3,8-triazaspiro[4.5]dec-3-en-2-one To a solution of benzyl (5R,7S)-4-(cyclohexylamino)-1-[4'-(isopropylsulfonyl)biphenyl-2-yl]-7-methyl-2-oxo-1,3,8-triazaspiro[4.5]dec-3-ene-8-carboxylate and benzyl (5S,7R)-4-(cyclohexylamino)-1-[4'-(isopropylsulfonyl)biphenyl-2-yl]-7-methyl-2-oxo-1,3,8-triazaspiro[4.5]dec-3-ene-8-carboxylate (1.90 g, 2.92 mmol) in methanol (50 mL) was added a catalytic amount of 10% palladium on carbon. After stirring for 1 h under and atmosphere of hydrogen at ambient pressure and temperature the reaction mixture was filtered through a pad of celite and concentrated under vacuum to afford the desired product that was subsequently used without further purification.

LRMS (M+1)=523.2

Step 7: (5S,7R)-8-(cyclobutylmethyl)-4-(cyclohexylamino)-1-[4'-(isopropylsulfonyl)biphenyl-2-yl]-7-methyl-1,3,8-triazaspiro[4.5]dec-3-en-2-one and (5S,7R)-8-(cyclobutylmethyl)-4-(cyclohexylamino)-1-[4'-(isopropylsulfonyl)biphenyl-2-yl]-7-methyl-1,3,8-triazaspiro[4.5]dec-3-en-2-one To a solution of (5R,7S)-4-(cyclohexylamino)-1-[4'-(isopropylsulfonyl)biphenyl-2-yl]-7-methyl-1,3,8-triazaspiro[4.5]dec-3-en-2-one and (5S,7R)-4-(cyclohexylamino)-1-[4'-(isopropylsulfonyl)biphenyl-2-yl]-7-methyl-1,3,8-triazaspiro[4.5]dec-3-en-2-one (0.2 g, 0.38 mmol) in DMF (1.5 mL) was added potassium carbonate (0.21 g, 1.53 mmol) followed by (bromomethyl)cyclobutane (0.057 g, 0.38 mmol). After stirring the at 70° C. overnight the reaction mixture was filtered and purified by reverse phase HPLC to afford the desired product. The free base of the product was formed by aqueous workup with aqueous base and an organic solvent like chloroform and the HCl salt was prepared by mixing the free base with ethereal HCl and evaporating to give the salt.

LRMS (M+1)=591.3

$^1$H NMR (CDCl$_3$) δ 7.87 (t, J=8.7 Hz, 2H), 7.74 (dd, J=6.5, 8.2 Hz, 2H), 7.49 (m, 4H), 3.91 (m, 1H), 3.21 (m, 1H), 2.75 (m, 2H), 2.51-0.95 (m, 24H), 1.30 (d, J=6.8 Hz, 6H), 1.05 (d, J=6.2 Hz, 3H).

The following examples in Table 7 were prepared using a procedure similar to that described for Example 2, starting with the 1-benzyl-2-methylpiperidin-4-one, (Intermediate I), except that tetrabutylammonium isocyanate was used in place of KOCN. In some instances, the racemic mixture was resolved via chiral HPLC to give the final enantiomerically pure product.

TABLE 7

| Ex # | Structure | Chemical name | Mass Spec (M + H)$^+$ |
|---|---|---|---|
| 57 | 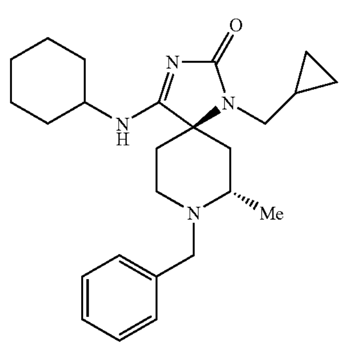 | (5R,7S)-8-benzyl-4-(cyclohexylamino)-1-(cyclopropylmethyl)-7-methyl-2-oxo-1,3-diaza-8-azoniaspiro[4.5]dec-3-ene trifluoroacetate | 409 |

TABLE 7-continued

| Ex # | Structure | Chemical name | Mass Spec (M + H)+ |
|---|---|---|---|
| 58 | 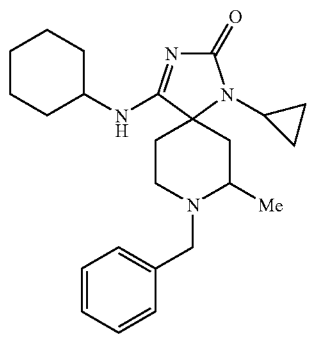 | (5R,7S)-(5S,7R)-8-benzyl-4-(cyclohexylamino)-1-cyclopropyl-7-methyl-2-oxo-1,3-diaza-8-azoniaspiro[4.5]dec-3-ene trifluoroacetate | 395 |
| 59 | 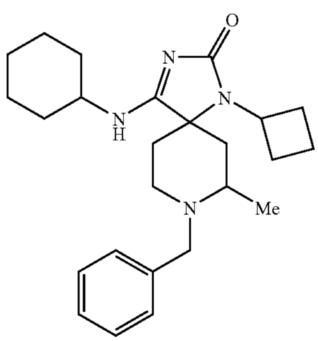 | (5R,7S)-(5S,7R)-8-benzyl-1-cyclobutyl-4-(cyclohexylamino)-7-methyl-2-oxo-1,3-diaza-8-azoniaspiro[4.5]dec-3-ene trifluoroacetate | 409 |
| 60 | 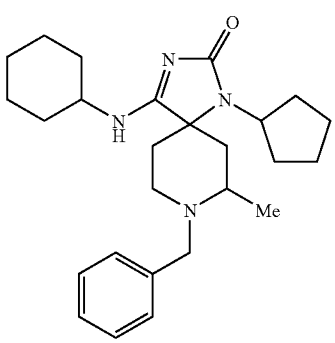 | (5R,7S)-(5S,7R)-8-benzyl-4-(cyclohexylamino)-1-cyclopentyl-7-methyl-2-oxo-1,3-diaza-8-azoniaspiro[4.5]dec-3-ene trifluoroacetate | 423 |
| 61 | 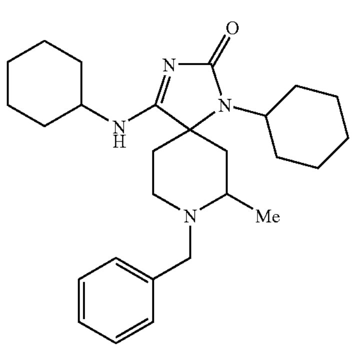 | (5R,7S)-(5S,7R)-8-benzyl-1-cyclohexyl-4-(cyclohexylamino)-7-methyl-2-oxo-1,3-diaza-8-azoniaspiro[4.5]dec-3-ene trifluoroacetate | 437 |

TABLE 7-continued

| Ex # | Structure | Chemical name | Mass Spec (M + H)+ |
|---|---|---|---|
| 62 | 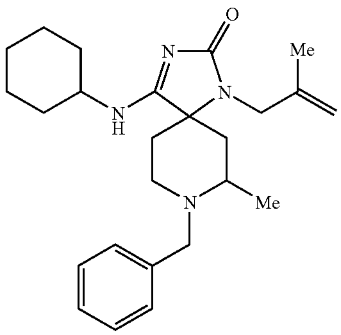 | (5R,7S)-(5S,7R)-8-benzyl-4-(cyclohexylamino)-7-methyl-1-(2-methylprop-2-en-1-yl)-2-oxo-1,3-diaza-8-azoniaspiro[4.5]dec-3-ene trifluoroacetate | 409 |
| 63 | 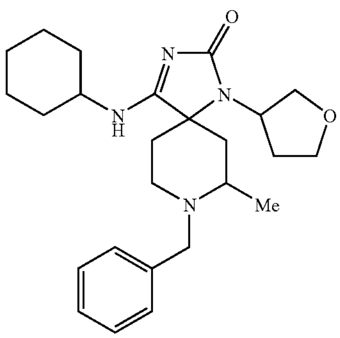 | (5R,7S)-(5S,7R)-8-benzyl-4-(cyclohexylamino)-7-methyl-2-oxo-1-(tetrahydrofuran-3-yl)-1,3-diaza-8-azoniaspiro[4.5]dec-3-ene trifluoroacetate | 425 |

Example 64

(5R,7S)-1-(3-fluorophenyl)-8-(3-isopropoxybenzyl)-7-methyl-4-{[(3S)-1-(methylsulfonyl)pyrrolidin-3-yl]amino}-2-oxo-1,3-diaza-8-azoniaspiro[4.5]dec-3-ene trifluoroacetate and (5S,7R)-1-(3-fluorophenyl)-8-(3-isopropoxybenzyl)-7-methyl-4-{[(3S)-1-(methylsulfonyl)pyrrolidin-3-yl]amino}-2-oxo-1,3-diaza-8-azoniaspiro[4.5]dec-3-ene trifluoroacetate

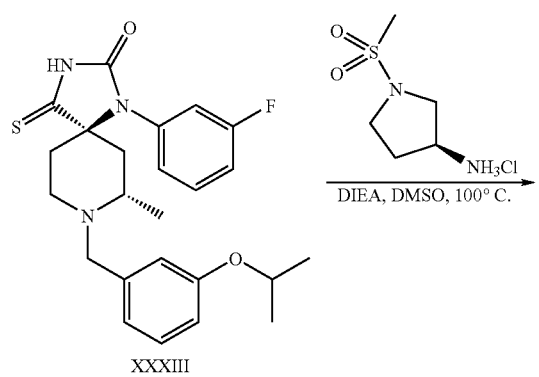

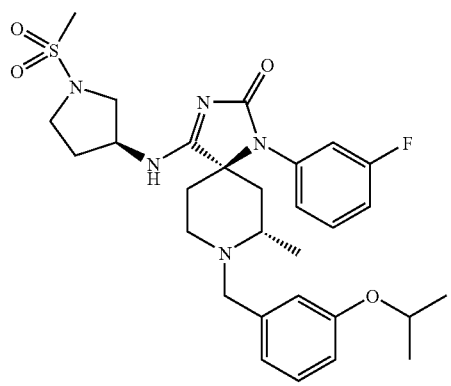

Example 64

The amine salt Intermediate XXII (167.3 mg, 0.834 mmol, 10 eq. Amine synthesis was described above), DMSO (0.45 mL), DIEA (150 μL, 0.86 mmol, 10 eq.), and the thiohydantoin (Intermediate XXXIII, 37.8 mg, 0.0856 mmol, 1.0 eq.) were placed into a vial with a stir bar. The reaction was stirred and heated in a 100° C. aluminum block for 3 h, and was then cooled to rt and submitted directly for reverse phase preparative HPLC (acetonitrile:water), to provide the desired analogue as the trifluoroacetate salt.

¹H NMR (CD₃OD, 400 MHz) δ: 7.35-7.21 (m, 2H), 7.20-7.05 (m, 3H), 7.00 (d, J=6.9 Hz, 1H), 6.79 (s, 1H), 6.75 (s, 1H), 6.74 (s, 1H), 4.61 (septet, J=6.1 Hz, 1H), 4.28 (d, J=13.2 Hz, 1H), 4.45-4.40 (br s, 1H), 4.18 (d, J=13.2 Hz, 1H), 3.70-3.55 (m, 2H), 3.50-3.35 (m, 2H), 2.95-2.90 (m, 5H), 2.75-2.50 (m, 4H), 2.50-2.25 (m, 3H), 2.25-2.05 (m, 1H), 1.53 (br s, 3H), 1.32 (d, J=5.9 Hz, 6H).

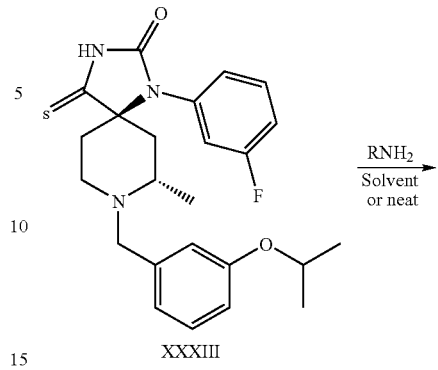

XXXIII

EI-MS m/z: 572 (M+H)⁺.

Examples 65-67 described in Table 8 are prepared in a manner similar to the procedure of Example 64 as shown in the scheme below. Intermediate XXXIII and the corresponding amine/or amine salt (commercially available or the preparation described above) are dissolved in DMSO or DMF. The resulting mixture is heated at 80° C.-100° C. until the reaction is complete. The desired invention compounds are purified by preparative HPLC. In some cases chiral HPLC was used to isolate the products.

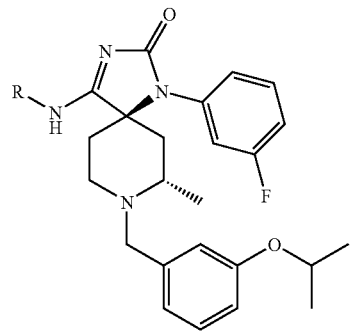

TABLE 8

| Ex # | Intermediate | Structure | Chemical Name | Mass Spec (M + H)⁺ |
|---|---|---|---|---|
| 65 | XXV | (structure) | (5R,7S)-4-[(3,3-difluorocyclohexyl)amino]-1-(3-fluorophenyl)-8-(3-isopropoxybenzyl)-7-methyl-2-oxo-1,3-diaza-8-azoniaspiro[4.5]dec-3-ene trifluoroacetate | 543 |

TABLE 8-continued

| Ex # | Intermediate | Structure | Chemical Name | Mass Spec (M + H)+ |
|---|---|---|---|---|
| 66 | XXV | 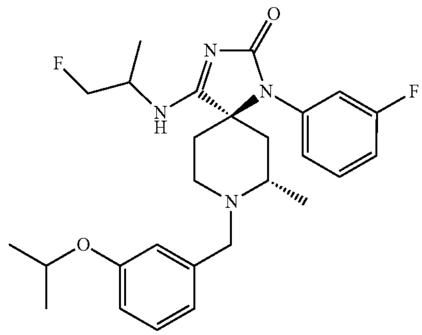 | (5R,7S)-(5S,7R)-4-[(2-fluoro-1-methylethyl)amino]-1-(3-fluorophenyl)-8-(3-isopropoxybenzyl)-7-methyl-1,3,8-triazaspiro[4.5]dec-3-en-2-one | 485 |
| 67 | Commercially available | 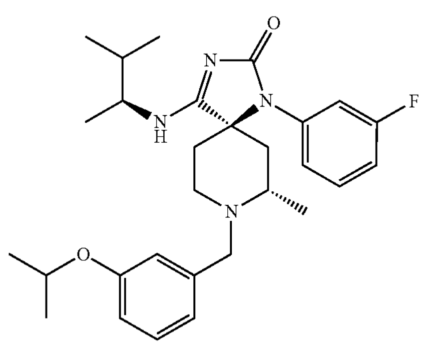 | (5R,7S)-(5S,7R)-4-{[(1S)-1,2-dimethylpropyl]amino)-1-(3-fluorophenyl)-8-(3-isopropoxybenzyl)-7-methyl-1,3,8-triazaspiro[4.5]dec-3-en-2-one | 495 |

Examples 68-78 described in Table 9 are prepared by the procedure as shown below. In some cases the benzyl 2-methyl-4-oxopiperidine-1-carboxylate used to prepare XXXII was resolved (see Example 11, Step 3, prep of 11-3S). XXXII and the corresponding amine I or amine salt (commercial available or the preparation described above) are dissolved in DMSO or DMF. The resulting mixture is heated at 80° C.-100° C. until the reaction is complete. The desired invention compounds are purified by preparative HPLC. In some cases chiral HPLC was used to isolate the products.

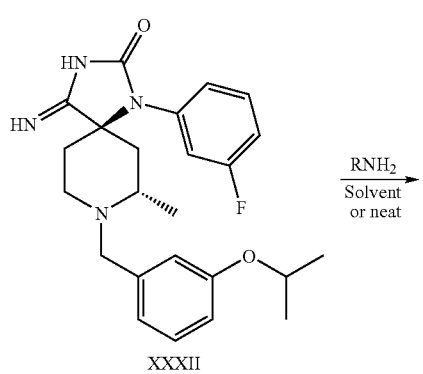

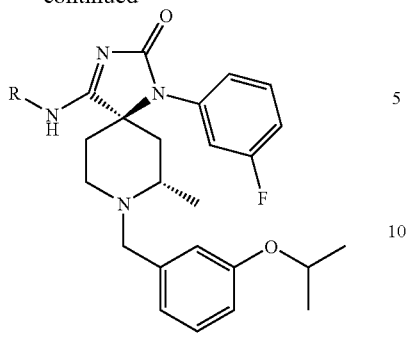

TABLE 9

| Ex # | Intermediate | Structure | Chemical Name | Mass Spec (M + H)+ |
|---|---|---|---|---|
| 68 | XXIII | | (5R,7S)-4-{[(1R,2R)-2-fluorocyclohexyl]amino}-1-(3-fluorophenyl)-8-(3-isopropoxybenzyl)-7-methyl-2-oxo-1,3-diaza-8-azoniaspiro[4.5]dec-3-ene trifluoroacetate and (5R,7S)-4-{[(1S,2S)-2-fluorocyclohexyl]amino}-1-(3-fluorophenyl)-8-(3-isopropoxybenzyl)-7-methyl-2-oxo-1,3-diaza-8-azoniaspiro[4.5]dec-3-ene trifluoroacetate | 525 |
| 69 | XXIII | 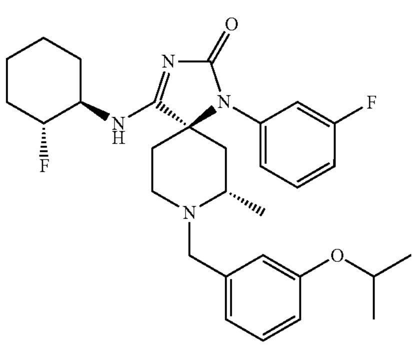 | (5R,7S)-4-{[(1R,2R)-2-fluorocyclohexyl]amino}-1-(3-fluorophenyl)-8-(3-isopropoxybenzyl)-7-methyl-1,3,8-triazaspiro[4.5]dec-3-en-2-one | 525.6 |

TABLE 9-continued

| Ex # | Intermediate | Structure | Chemical Name | Mass Spec (M + H)+ |
|---|---|---|---|---|
| 70 | XXIII | 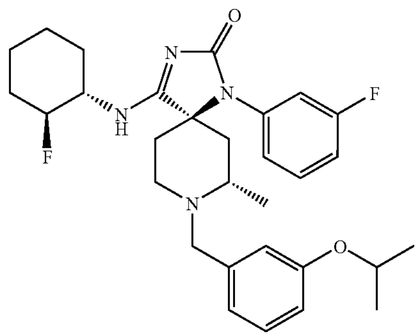 | (5R,7S)-4-{[(1S,2S)-2-fluorocyclohexyl]amino}-1-(3-fluorophenyl)-8-(3-isopropoxybenzyl)-7-methyl-1,3,8-triazaspiro[4.5]dec-3-en-2-one | 525.6 |
| 71 | XXVI | 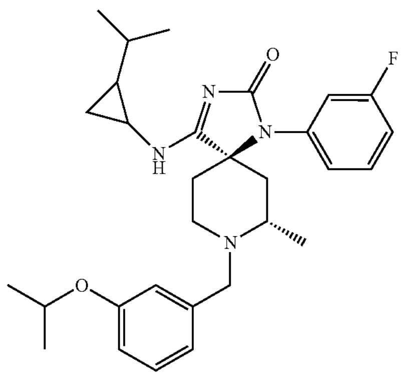 | (5R,7S)-1-(3-fluorophenyl)-8-(3-isopropoxybenzyl)-4-[(2-isopropylcyclopropyl)amino]-7-methyl-1,3,8-triazaspiro[4.5]dec-3-en-2-one | 507 |
| 72 | XXVII | | (5R,7S)-4-{[(1R,2R)-2-fluorocyclopentyl]amino}-1-(3-fluorophenyl)-8-(3-isopropoxybenzyl)-7-methyl-1,3,8-triazaspiro[4.5]dec-3-en-2-one and (5R,7S)-4-{[(1S,2S)-2-fluorocyclopentyl]amino}-1-(3-fluorophenyl)-8-(3-isopropoxybenzyl)-7-methyl-1,3,8-triazaspiro[4.5]dec-3-en-2-one | 511 |

TABLE 9-continued

| Ex # | Intermediate | Structure | Chemical Name | Mass Spec (M + H)+ |
|---|---|---|---|---|
| 73 | XXVIII | 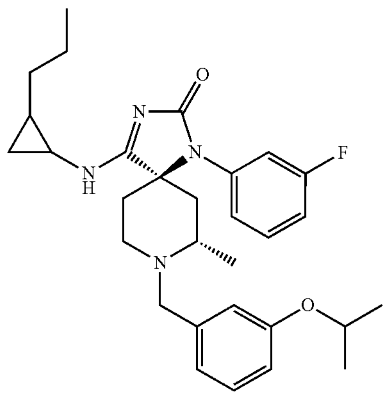 | (5R,7S)-1-(3-fluorophenyl)-8-(3-isopropoxybenzyl)-4-[(2-isopropylcyclopropyl)amino]7-methyl-1,3,8-triazaspiro[4.5]dec-3-en-2-one | 507 |
| 74 | XXIX | 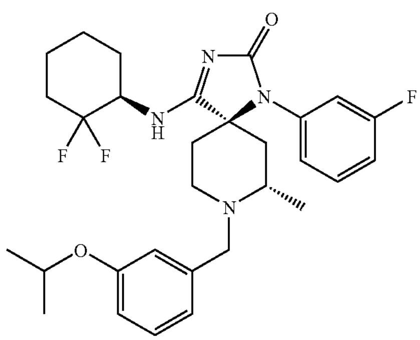 | (5R,7S)-4-{[(1R)-2,2-difluorocyclohexyl]amino}-1-(3-fluorophenyl)-8-(3-isopropoxybenzyl)-7-methyl-1,3,8-triazaspiro[4.5]dec-3-en-2-one | 543 |
| 75 | XXIX | 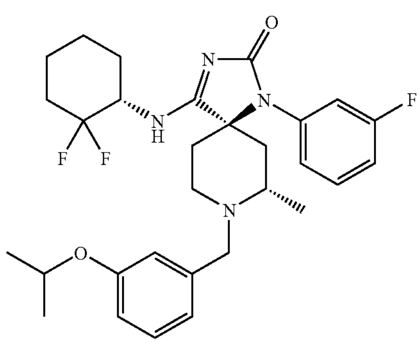 | (5R,7S)-4-{[(1S)-2,2-difluorocyclohexyl]amino}-1-(3-fluorophenyl)-8-(3-isopropoxybenzyl)-7-methyl-1,3,8-triazaspiro[4.5]dec-3-en-2-one | 543 |
| 76 | XXX | 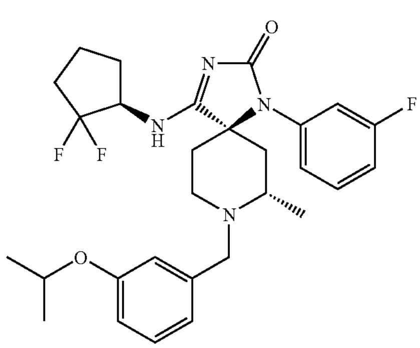 | (5R,7S)-4-{[(1R)-2,2-difluorocyclopentyl]amino}-1-(3-fluorophenyl)-8-(3-isopropoxybenzyl)-7-methyl-1,3,8-triazaspiro[4.5]dec-3-en-2-one | 529 |

TABLE 9-continued

| Ex # | Intermediate | Structure | Chemical Name | Mass Spec (M + H)+ |
|---|---|---|---|---|
| 77 | XXX | 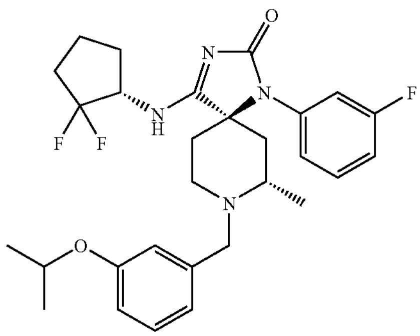 | (5R,7S)-4-{[(1S)-2,2-difluorocyclopentyl]amino}-1-(3-fluorophenyl)-8-(3-isopropoxybenzyl)-7-methyl-1,3,8-triazaspiro[4.5]dec-3-en-2-one | 529 |
| 78 | XXXI | 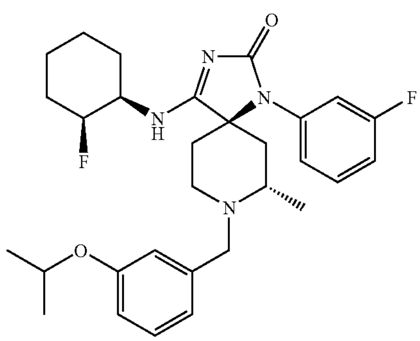 | (5R,7S)-4-{[(1R,2S)-2-fluorocyclohexyl]amino}-1-(3-fluorophenyl)-8-(3-isopropoxybenzyl)-7-methyl-1,3,8-triazaspiro[4.5]dec-3-en-2-one and (5R,7S)-4-{[(1S,2R)-2-fluorocyclohexyl]amino}-1-(3-fluorophenyl)-8-(3-isopropoxybenzyl)-7-methyl-1,3,8-triazaspiro[4.5]dec-3-en-2-one | 525 |

The example in Table 10 was prepared from the appropriate commercially available or custom-made amine and the thiohydantoin Intermediate XV above, using methods similar to that described for Example 64. The amine or amine salt was heated with the thiohydantoin neat or with an appropriate base like N-methylmorpholine as the base/cosolvent and in some instances an additional appropriate solvent like toluene was used.

TABLE 10

| Ex # | Intermediate | Structure | Chemical name | Mass Spec (M + H) |
|---|---|---|---|---|
| 79 | Commercially available | 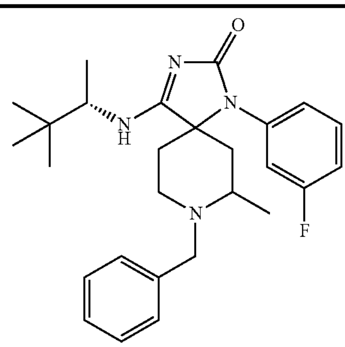 | (5R,7S)-8-benzyl-1-(3-fluorophenyl)-7-methyl-4-{[(1S)-1,2,2-trimethylpropyl]amino}-1,3,8-triazaspiro[4.5]dec-3-en-2-one and (5S,7R)-8-benzyl-1-(3-fluorophenyl)-7-methyl-4-{[(1S)-1,2,2-trimethylpropyl]amino}-1,3,8-triazaspiro[4.5]dec-3-en-2-one | 451.3 |

Example 80

(5R,7S)-4-(cyclohexylimino)-1-(3-fluorophenyl)-8-(3-isopropoxybenzyl)-3,7-dimethyl-1,3,8-triazaspiro[4.5]decan-2-one

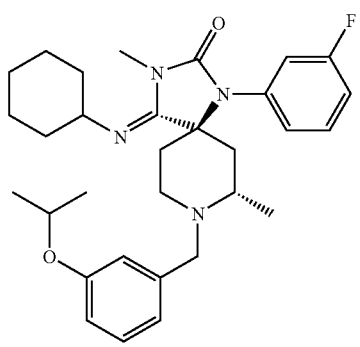

(5R,7S)-4-(cyclohexylamino)-1-(3-fluorophenyl)-8-(3-isopropoxybenzyl)-7-methyl-1,3,8-triazaspiro[4.5]dec-3-en-2-one (11-10, 0.5 g, 0.1 mmoles) was dissolved in THF (2 mL) in an oven-dried flask and the solution was cooled under nitrogen to −78° C. in a dry ice/acetone bath. To the cooled reaction was added a 1 M solution of Lithium bis(trimethylsilyl)amide in THF (0.3 mL, 0.3 mmoles) dropwise, and the solution was warmed to −20° C. for 10 min. The solution was cooled to −50° C. and iodomethane (0.014 g, 0.1 mmole) was added and the reaction stirred for 30 min at −50° C. The reaction was then allowed to warm to rt. A drop of acetic acid was added and the volume was reduced. The residue was partitioned between saturated aqueous sodium bicarbonate (5 mL) and methylene chloride (5 mL). The organic layer was dried over sodium sulfate, filtered and reduced to a residue which was chromatographed on silica gel eluting with a gradient elution of 100% methylene chloride going to 30% methylene chloride/methanol/10% NH$_4$OH solution over 20 min. The desired fractions were combined and the solvents removed to give the product.

(major conformer) $^1$H NMR (600 MHz, CD$_2$Cl$_2$) 7.38 (dd, J=8, 14.8 Hz, 1H), 7.13 (m, 2H), 7.0 (m, 2H), 6.75 (m, 3H), 4.5 (m, 1H), 4.14 (m, 1H), 3.93 (d, J=13.7, 1H), 2.94(s, 3H), 2.75 (d, J=13.7, 1H), 2.54 (m, 1H), 2.4 (m, 1H), 2.22 (m, 1H), 2.1 (m, 2H), 2.0-1.6 (m, 7H), 1.4 (m, 4H), 1.3 (m, 1H), 1.29 (d, J=5 Hz, 6H), 1.05 (m, 3H).

(minor conformer) $^1$H NMR (600 MHz, CD$_2$Cl$_2$) 7.38 (dd, J=8, 14.8 Hz, 1H), 7.13 (m, 2H), 7.0 (m, 2H), 6.75 (m, 3H), 4.5 (m, 1H), 4.0 (m, 1H), 3.86 (d, J=13.4, 1H), 2.58 (d, J=13.4, 1H), 2.46 (m, 1H), 2.1 (m, 3H), 1.9-1.6 (m, 8H), 1.4 (m, 5H), 1.33 (d, J=6 Hz, 3H), 1.26 (d, J=6 Hz, 6H), 1.1 (m, 3H). LCMS ion fragment=507.11

The following abbreviations are used throughout the text:

| | |
|---|---|
| Me: | methyl |
| Et: | ethyl |
| t-Bu: | tert-butyl |
| Ar: | aryl |
| Ph: | phenyl |
| Bn: | benzyl |
| Ac: | acetyl |
| TMSCN: | trimethylsilyl cyanide |
| DMSO: | dimethylsulfoxide |
| EDTA: | ethylene diamine tetraacetic acid |
| Boc: | tert-butyloxy carbonyl |
| CHAPS: | 3-[(3-cholamidopropyl)dimethylammonio]-2-hydroxy-1-propanesulfonate |
| BSA: | bovine serum albumin |
| TFA: | trifluoracetic acid |
| DME: | dimethoxyethane |
| DPPA: | diphenylphosphorlyazide |
| DIEA: | diisopropylethylamine |
| TBAF: | tetrabutylammonium fluoride |
| TEA: | triethylamine |
| DCE: | dichloroethane |
| DCM: | dichloromethane |
| TPP: | triphenyl phosphine |
| OTs: | toluene sulfonate |
| BOP: | benzotriazolyl-N-oxy-tris(dimethylamino) phosphonium hexaflurophosphate |
| DIPEA: | diisopropylethylamine |
| DMF: | dimethylformamide |
| DIAD: | diisopropylazodicarboxylate |
| MTBE: | methyltertbutylether |
| LAH: | lithium aluminum hydride |
| DIBAL: | diisobutylaluminum hydride |
| rt: | room temperature |
| aq: | aqueous |
| HPLC: | high performance liquid chromatography |
| MS: | mass spectrometry |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

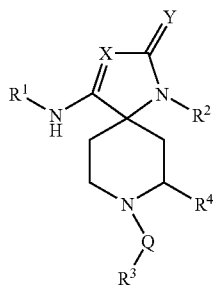

or its tautomer (I')

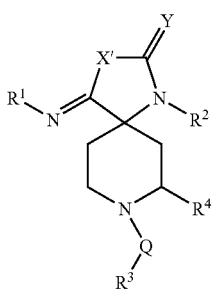

wherein
X is N;
X' is NH;
Y is selected from the group consisting of
(1) O, and
(2) S;
$R^1$ is selected from the group consisting of
(1) —$C_{1-10}$ alkyl, and
(2) —$C_{3-12}$ cycloalkyl, wherein one or two of the ring carbon atoms is optionally replaced by a —Si($C_{1-6}$ alkyl)$_2$— group,
wherein said alkyl and said cycloalkyl $R^1$ moiety is optionally substituted with one or more
(a) halo, and
(b) —$C_{1-10}$ alkyl;
$R^2$ is selected from the group consisting of phenyl or thienyl,
wherein said phenyl or thienyl $R^2$ moiety is optionally substituted with one or more
(a) halo, and
(b) —$C_{0-6}$ alkyl-aryl, wherein said aryl is optionally substituted with one or more —$SO_2Cl_{1-3}$ alkyl;
Q is —$C_{1-6}$ alkylene, wherein said alkylene is optionally substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) aryl, and
(h) heteroaryl;
$R^3$ is selected from the group consisting of phenyl or —$C_{3-12}$ cycloalkyl,
wherein said phenyl or cycloalkyl, $R^3$ moiety is optionally substituted with one or more
(a) halo,
(b) —$C_{2-10}$ alkenyl,
(c) —$C_{3-12}$ cycloalkyl,
(d) —O—C_12 cycloalkyl,
(e) —O—$C_{1-10}$ alkyl,
(f) —O—$C_{3-12}$ heterocyclic, wherein said heterocyclic group has from 4 to 8 ring atoms, wherein one ring atom is a heteroatom selected from the group consisting of nitrogen, sulfur and oxygen, and
(g) heteroaryl;

$R^4$ is —$C_{2-4}$ alkenyl;

and pharmaceutically acceptable salts thereof, and individual enantiomers and diastereomers thereof.

2. A compound of claim 1 of formula (I) or (I'), wherein Y is O.

3. A compound of claim 1, wherein $R^1$ is selected from the group consisting of optionally substituted $C_{1-6}$ alkyl or $C_{3-6}$ cycloalkyl.

4. A compound of claim 1, wherein $R^2$ is phenyl, wherein the phenyl is optionally substituted with one or more
(i) halo, and
(ii) phenyl optionally substituted with —$SO_2C_{1-3}$ alkyl.

5. A compound of claim 1, wherein Q is $C_{1-3}$ alkylene and $R^3$ is phenyl, wherein the phenyl is optionally substituted with one or more
(A) halo, and
(B) —$OC_{1-10}$ alkyl.

6. A compound of claim 5, wherein Q is —$CH_2$—.

7. A compound of claim 1, wherein $R^4$ is $C_{2-3}$ alkenyl.

8. A compound of claim 1, which is a compound of formula (II)

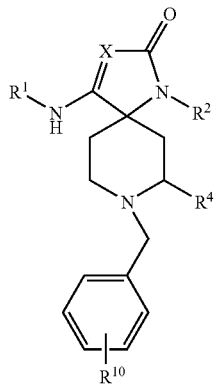

or its tautomer (II')

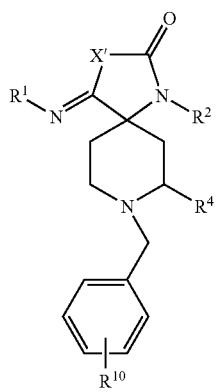
(II')

wherein X, X', $R^1$, $R^2$, and $R^4$ are as defined in claim 1, and $R^{10}$ is selected from the group consisting of
(1) halo,
(2) —$C_{2-10}$ alkenyl, and
(3) —$OC_{1-10}$ alkyl,
and pharmaceutically acceptable salts thereof, and individual enantiomers and diastereomers thereof.

9. A compound of claim 8, wherein $R^2$ is phenyl which is optionally substituted with one or more
(i) halo,
(ii) phenyl, optionally substituted with —$SO_2C_{1-3}$ alkyl.

10. A compound of claim 8, wherein $R^4$ is —$C_{2-3}$ alkenyl.

11. A compound of claim 1 which is a compound of formula (III)

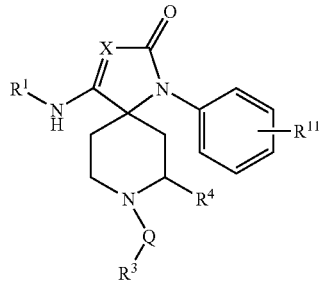
(III)

or its tautomer (III')

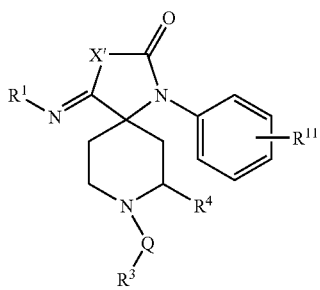
(III')

wherein X, X', Q, $R^1$, $R^3$, and $R^4$ are as defined in claim 1, and $R^{11}$ is selected from the group consisting of
(1) halo, and
(2) optionally substituted phenyl;
and pharmaceutically acceptable salts thereof, and individual enantiomers and diastereomers thereof.

12. A compound of claim 11, wherein Q is $C_{1-3}$ alkylene, and $R^3$ is phenyl, wherein the phenyl is optionally substituted with one or more
(A) halo, and
(B) —$OC_{1-10}$ alkyl.

13. A compound of claim 11, wherein $R^4$ is $C_{2-3}$ alkyl.

14. A compound of claim 1, or a pharmaceutically acceptable salt thereof, or an individual enantiomer thereof, wherein the compound of formula (I) and (I') is a compound of formula (IB)

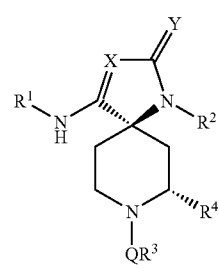
(IB)

and its tautomer (IB'):

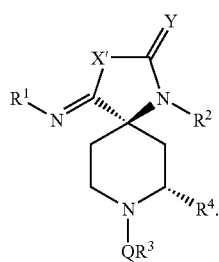
(IB')

15. A compound which is selected from the group consisting of

| Ex # | Structure | Chemical name |
|---|---|---|
| 51 | 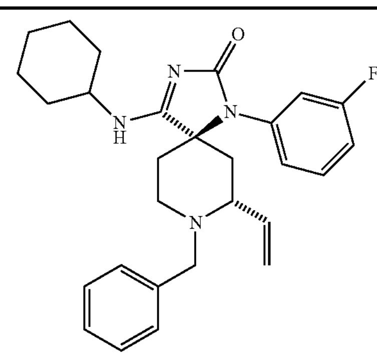 | (5R,7R)-8-benzyl-4-(cyclohexyl-amino)-1-(3-fluorophenyl)-7-vinyl-1,3,8-triaza-spiro[4.5]dec-3-en-2-one, |

| Ex # | Structure | Chemical name |
|---|---|---|
| 52 | 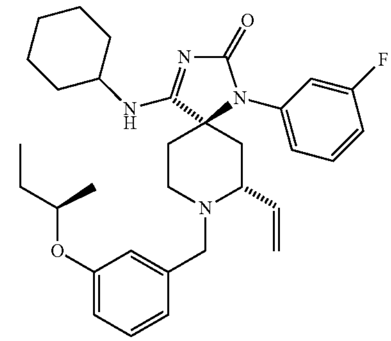 | (5R,7R)-4-(cyclohexyl-amino)-1-(3-fluorophenyl)-8-(3-{[(1R)-1-methyl-pro-pyl]oxy}benzyl)-7-vinyl-1,3,8-triaza-spiro[4.5]dec-3-en-2-one, |
| 53 | 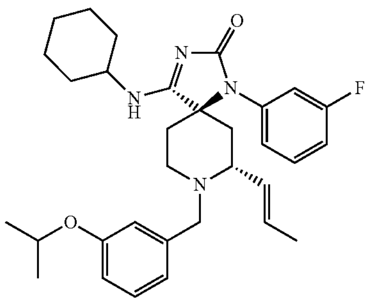 | (5R,7R)-4-(cyclohexyl-amino)-1-(3-fluorophenyl)-8-(3-isopro-poxybenzyl)-7-[(1E)-prop-1-en-1-yl]-1,3,8-triaza-spiro[4.5]dec-3-en-2-one, and |
| 54 | | (5R,7R)-4-(cyclohexyl-amino)-1-(3-fluorophenyl)-8-(3-isopro-poxybenzyl)-7-[(1Z)-prop-1-en-1-yl]-1,3,8-triaza-spiro[4.5]dec-3-en-2-one, | or a pharmaceutically acceptable salt thereof.

16. A pharmaceutically acceptable salt of a compound of claim 15, wherein the salt is selected from the group consisting of sulfate, phosphate, citrate, malate, mandelate, hippurate, trifluoroacetate and hydrochloric acid salts.

17. A pharmaceutical composition comprising a compound of claim 1, or a pharmaceutically acceptable salt thereof, and a pharmaceutically acceptable carrier.

\* \* \* \* \*